(12) United States Patent
Cheve et al.

(10) Patent No.: US 9,493,455 B2
(45) Date of Patent: Nov. 15, 2016

(54) AZAINDOLE DERIVATIVES AS INHIBITORS OF PROTEIN KINASES

(71) Applicant: ORIBASE PHARMA, Montpellier (FR)

(72) Inventors: Gwénaël Cheve, Lunel (FR); Bénédicte Dayde-Cazals, Montpellier (FR); Bénédicte Fauvel, Montpellier (FR); Cédric Bories, Montpellier (FR); Abdelaziz Yasri, Castelnau le Lez (FR)

(73) Assignee: ORIBASE PHARMA, Montpellier (FR)

( * ) Notice: Subject to any disclaimer, the term of this patent is extended or adjusted under 35 U.S.C. 154(b) by 0 days.

(21) Appl. No.: 14/655,613

(22) PCT Filed: Dec. 30, 2013

(86) PCT No.: PCT/EP2013/078140
§ 371 (c)(1),
(2) Date: Jun. 25, 2015

(87) PCT Pub. No.: WO2014/102378
PCT Pub. Date: Jul. 3, 2014

(65) Prior Publication Data
US 2015/0353540 A1    Dec. 10, 2015

Related U.S. Application Data

(60) Provisional application No. 61/746,785, filed on Dec. 28, 2012.

(30) Foreign Application Priority Data

Dec. 28, 2012   (FR) ...................... 12 62934

(51) Int. Cl.
| | | |
|---|---|---|
| C07D 401/02 | (2006.01) | |
| C07D 401/10 | (2006.01) | |
| A61K 31/437 | (2006.01) | |
| A61K 31/4353 | (2006.01) | |
| C07D 471/04 | (2006.01) | |
| C12Q 1/48 | (2006.01) | |
| G01N 33/574 | (2006.01) | |
| A61K 31/4375 | (2006.01) | |

(52) U.S. Cl.
CPC ......... *C07D 471/04* (2013.01); *A61K 31/4375* (2013.01); *C12Q 1/485* (2013.01); *G01N 33/57484* (2013.01); *G01N 2333/91215* (2013.01); *G01N 2500/04* (2013.01); *G01N 2500/10* (2013.01); *G01N 2500/20* (2013.01); *G01N 2800/52* (2013.01)

(58) Field of Classification Search
CPC .............. C07D 401/02; C07D 401/10; A61K 31/437; A61K 31/4353
USPC .......................................... 546/121; 514/300
See application file for complete search history.

(56) References Cited

U.S. PATENT DOCUMENTS

2015/0353539 A1* 12/2015 Cheve .................. C07D 471/04
514/253.04

FOREIGN PATENT DOCUMENTS

| WO | WO 2007/017143 A1 | 2/2007 |
|---|---|---|
| WO | WO 2008/028617 A1 | 3/2008 |
| WO | WO 2008/144253 A1 | 11/2008 |
| WO | WO 2009/012283 A1 | 1/2009 |
| WO | WO 2009/111278 A2 | 9/2009 |
| WO | 2010092489 * | 8/2010 |
| WO | WO 2010/092489 A1 | 8/2010 |

OTHER PUBLICATIONS

Brunton et al., "Src and focal adhesion kinase as therapeutic targets in cancer," Current Opinion in Pharmacology, vol. 8, 2008 (Available online Jul. 22, 2008), pp. 427-432.
Cébe-Suarez et al., "The role of VEGF receptors in angiogenesis; complex partnerships," Cellular and Molecular Life Sciences, vol. 63, 2006 (Online First Feb. 7, 2006), pp. 601-615.
Chico et al., "Targeting protein kinases in central nervous system disorders," Nature Reviews Drug Discovery, vol. 8, No. 11, Nov. 2009 (available in PMC Feb. 19, 2010), pp. 1-39.
Cook et al., "Angiogenesis Inhibitors—Current Strategies and Future Prospects," CA: A Cancer Journal for Clinicians, vol. 60, No. 4, 2010 (available in PMC Jul. 1, 2011), pp. 1-35.
Fox et al., "Angiogenesis: pathological, prognostic, and growth-factor pathways and their link to trial design and anticancer drugs," The Lancet Oncology, vol. 2, May 2001, pp. 278-289.
Hofmeister et al., "Anti-cancer therapies targeting the tumor stroma," Cancer Immunology, Immunotherapy, vol. 57, 2008 (Published online Jul. 27, 2007), pp. 1-17.
International Search Report (Form PCT/ISA/210) for International Application No. PCT/EP2013/078138, dated Feb. 26, 2014.
International Search Report (Form PCT/ISA/210) for International Application No. PCT/EP2013/078139, dated Feb. 26, 2014.
Khazak et al., "Selective Raf Inhibition in Cancer Therapy," Expert Opinion on Therapeutic Targets, vol. 11, No. 12, Dec. 2007 (available in PMC Aug. 3, 2009), pp. 1-35.

(Continued)

*Primary Examiner* — Niloofar Rahmani
(74) *Attorney, Agent, or Firm* — Birch, Stewart, Kolasch & Birch, LLP

(57) ABSTRACT

The present invention relates to compounds of the following formula (I) and/or the pharmaceutically acceptable addition salts, solvates, enantiomers, diastereoisomers thereof, as well as mixtures thereof. The subject matter of the present invention thus also includes the preparation of compounds of formula (I), their uses, in particular in the inhibition of protein kinases which are implicated for example in numerous diseases such as cancers or immune system disorders.

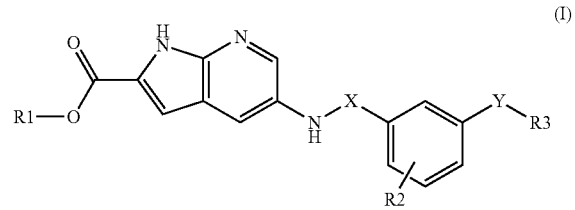

18 Claims, 16 Drawing Sheets

(56) References Cited

OTHER PUBLICATIONS

Kontzias et al., "Kinase inhibitors in the treatment of immune-mediated disease," F1000 Medicine Reports, vol. 4, No. 5, Mar. 1, 2012, pp. 1-8.
Mouaddib et al., "Synthesis of Indolo[3,2-c]quinoline and Pyrido[3',2':4,5][3,2-c]quinoline Derivatives," Synthesis, No. 4, 2000, pp. 549-556.
Pennell et al., "Combined Inhibition of the VEGFR and EGFR Signaling Pathways in the Treatment of NSCLC," The Oncologist, vol. 14, 2009 (first published online Apr. 8, 2009), pp. 399-411.
Potapova et al., "Contribution of individual targets to the antitumor efficacy of the multitargeted receptor tyrosine kinase inhibitor SU11248," Molecular Cancer Therapeutics, vol. 5, No. 5, May 2006, pp. 1280-1289.
Raman et al., "Role of chemokines in tumor growth," Cancer Letters, vol. 256, 2007, pp. 137-165.
Sun et al., "Antioxidative and thrombolytic TMP nitrone for treatment of ischemic stroke," Bioorganic and Medicinal Chemistry, vol. 16, No. 19, 2008 (Available online Aug. 31, 2008), pp. 8868-8874.
Wang et al., "Substituent Diversity-Directed Synthesis of Indole Derivatives," Journal of Combinatorial Chemistry, vol. 11, No. 4, 2009 (Published on Web May 26, 2009), pp. 556-575.
Yeatman, "A Renaissance for SRC," Nature Reviews Cancer, vol. 4, Jun. 2004, pp. 470-480.
International Search Report issued in PCT/EP2013/078140, mailed on Feb. 26, 2014.

\* cited by examiner

AZAINDOLE DERIVATIVES AS INHIBITORS OF PROTEIN KINASES

CROSS REFERENCE TO RELATED APPLICATIONS

This application is the National Phase of PCT International Application No. PCT/EP2013/078140, filed on Dec. 30, 2013, which claims priority under 35 U.S.C. 119(e) to U.S. Provisional Application No. 61/746,785, filed on Dec. 28, 2012 and under 35 U.S.C. 119(a) to Patent Application No. 1262934, filed in France on Dec. 28, 2012, all of which are hereby expressly incorporated by reference into the present application.

INTRODUCTION

The present invention relates to compounds that are inhibitors of protein kinases, the method of preparation thereof and the therapeutic applications thereof.

Dysfunction/deregulation of protein kinases (PK) is the cause of a large number of pathologies including oncological, immunological, neurological, metabolic and infectious diseases. This has generated considerable interest in the development of small molecules and biological kinase inhibitors for the treatment of these disorders.

Numerous PK are particularly deregulated during the process of tumorigenesis. Consequently protein kinases are attractive targets for anticancer drugs, including small molecule inhibitors that usually act to block the binding of ATP or substrate to the catalytic domain of the tyrosine kinase and monoclonal antibodies that specifically target receptor tyrosine kinases (RTK) and their ligands. In solid malignancies, it is unusual for a single kinase abnormality to be the sole cause of disease and it is unlikely that tumors are dependent on only one abnormally activated signaling pathway. Instead multiple signaling pathways are dysregulated. Furthermore, even single molecular abnormalities may have multiple downstream effects. Multi targeted therapy using a single molecule (MTKI="Multi-Targeted Kinase Inhibitors") which targets several signaling pathways simultaneously, is more effective than single targeted therapy. Single targeted therapies have shown activity for only a few indications and most solid tumors show deregulation of multiple signaling pathways. For example, the combination of a vascular endothelial growth factor receptor (VEGFR) inhibitor and platelet derived growth factor receptor (PDGFR) inhibitor results in a cumulative antitumor efficacy (Potapova et al., Mol Cancer Ther 5, 1280-1289, 2006).

Tumors are not built up solely of tumor cells. An important part consists of connective tissue or stroma, made up of stromal cells and extracellular matrix, which is produced by these cells. Examples of stromal cells are fibroblasts, endothelial cells and macrophages. Stromal cells also play an important role in the carcinogenesis, where they are characterized by upregulation or induction of growth factors and their receptors, adhesion molecules, cytokines, chemokines and proteolytic enzymes (Hofmeister et al., Immunotherapy 57, 1-17, 2007; Raman et al., Cancer Letters 256, 137-165, 2007; Fox et al., The Lancet Oncology 2, 278-289, 2001).

The receptor associated tyrosine kinase VEGFR on endothelial and tumor cells play a central role in the promotion of cancer by their involvement in angiogenesis (Cébe-Suarez et al., Cell Mol Life Sci 63, 601-615, 2006). In addition, the growth factors TGF-β, PDGF and FGF2 secreted by cancer cells transform normal fibroblasts into tumor associated fibroblasts, which make their receptors a suitable target for inhibition by kinase inhibitors (Raman et al., 2007).

Moreover, increasing evidence suggests a link between the EGF receptor (EGFR) and HER2 pathways and VEGF-dependent angiogenesis and preclinical studies have shown both direct and indirect angiogenic effects of EGFR signaling (Pennell and Lynch, The Oncologist 14, 399-411, 2009). Upregulation of tumor pro-angiogenic factors and EGFR-independent tumor-induced angiogenesis have been suggested as a potential mechanism by which tumor cells might overcome EGFR inhibition.

The major signaling pathways regulated by EGFR activation are the PI3K, MAPK and Stat pathways that lead to increased cell proliferation, angiogenesis, inhibition of apoptosis and cell cycle progression. EGFR is overexpressed in a wide variety of solid tumors, such as lung, breast, colorectal and cancers of the head and neck (Cook and Figg, CA Cancer J Clin 60, 222-243 2010). Furthermore, higher expression of EGFR has been shown to be associated with metastasis, decreased survival and poor prognosis.

c-Src, a membrane-associated non receptor tyrosine kinase, is involved in a number of important signal transduction pathways and has pleiotropic effects on cellular function. c-Src integrates and regulates signaling from multiple transmembrane receptor-associated tyrosine kinases, such as the EGFR, PDGFR, IGF1R, VEGFR, HER2. Together, these actions modulate cell survival, proliferation, differentiation, angiogenesis, cell motility, adhesion, and invasion (Brunton and Frame, Curr Opin Pharmacol 8, 427-432, 2008). Overexpression of the protein c-Src as well as the increase in its activity were observed in several types of cancers including colorectal, gastrointestinal (hepatic, pancreatic, gastric and oesophageal), breast, ovarian and lung (Yeatman, Nat Rev Cancer 4, 470-480, 2004).

The activation in EGFR or KRAS in cancers leads to a greatly enhanced level of Ras-dependent Raf activation. Hence, elimination of Raf function is predicted to be an effective treatment for the numerous cancers initiated with EGFR and KRAS lesions (Khazak et al., Expert Opin. Ther. Targets 11, 1587-1609, 2007).

Besides activation of Raf signaling in tumors, a number of studies implicate the activation of the Ras-Raf-MAPK signaling pathway as a critical step in vasculogenesis and angiogenesis. Such activation is induced by growth factor receptors such as VEGFR2, FGFR2 and thus inhibition of Raf activation represents a legitimate target for modulation of tumor angiogenesis and vascularization.

Although VEGFR, PDGFR, EGFR, c-Src and Raf are important targets on both tumor cells and tumor stroma cells, other kinases such as FGFR only function in stromal cells and other oncogenes often only function in tumor cells.

Protein kinases are fundamental components of diverse signaling pathways, including immune cells. Their essential functions have made them effective therapeutic targets. Initially, the expectation was that a high degree of selectivity would be critical; however, with time, the use of "multikinase" inhibitors has expanded. Moreover, the spectrum of diseases in which kinase inhibitors are used has also expanded to include not only malignancies but also immune-mediated diseases/inflammatory diseases. The first step in signaling by multi-chain immune recognition receptors is mediated initially by Src family protein tyrosine kinases. MTKI targeting kinases involved in immune function are potential drugs for autoimmune diseases such as rheumatoid arthritis, psoriasis and inflammatory bowel diseases (Kontzias et al., F1000 Medicine Reports 4, 2012)

Protein kinases mentioned previously are also key components of many other physiological and pathological mechanisms such as neurodegeneration and neuroprotection (Chico et al., Nature Reviews Drug Discovery 8, 892-909, 2009), atherosclerosis, osteoporosis and bone resorption, macular degeneration, pathologic fibrosis, Cystogenesis (human autosomal dominant polycystic kidney disease . . . ).

In WO2010/092489 and related patents/patent applications, we identified several compounds which exhibited interesting properties for such applications. However, we have discovered that some of these compounds could be enhanced in their properties by selectively working on particular regions of their structures. However, the mechanism of action of these structures on kinases was not precisely elucidated at the time of WO2010/092489's filing and thus it was unexpectedly that we found the high activities of the structures disclosed in the present application.

The subject matter of the present invention is to offer novel multi-targeted kinase inhibitors, having an original backbone, which can be used therapeutically in the treatment of pathologies associated with deregulation of protein kinases including tumorigenesis, human immune disorders, inflammatory diseases, thrombotic diseases, neurodegenerative diseases, bone diseases, macular degeneration, fibrosis, cystogenesis.

The inhibitors of the present invention can be used in particular for the treatment of numerous cancers and more particularly in the case of liquid tumors such hematological cancers (leukemias) or solid tumors including but not limited to squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, breast cancer, melanoma, colorectal cancer, endometrial carcinoma, salivary gland carcinoma, renal cancer, prostate cancer, vulval cancer, thyroid cancer, sarcomas, astrocytomas, and various types of hyperproliferative diseases.

SUMMARY OF THE INVENTION

The present invention relates to compounds of the following formula (I):

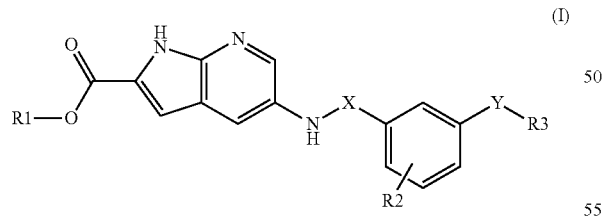

(I)

characterized in that,

R1 is a $C_1$-$C_6$ alkyl, preferably methyl, ethyl or n-propyl, alternatively, R1 is a hydrogen atom, X is $CH_2$ or C=O, R2 is hydrogen, a $C_1$-$C_6$ alkyl or a halogen, Y is chosen from a group consisting of HNC(O), HNC(S), $HNSO_2$, $HNC(O)CH_2$, HNC(O)NH, HNC(S)NH, C(O)NH, $C(O)NHCH_2$, $CH_2NHC(O)$ and $CH_2NHC(S)$, R3 is chosen from a group consisting of:
  a phenyl group mono or polysubstituted with:
    a hydroxyl,
    a halogen,
    a $C_1$-$C_6$ alkyl-amine, preferably a secondary $C_1$-$C_6$ alkyl-amine,
    a $C_1$-$C_6$ alkoxy,
    a $C_1$-$C_6$ trifluoroalkoxy, preferably a trifluoromethoxy,
    a $C_1$-$C_6$ alkyl, preferably a methyl, isopropyl,
    a $C_1$-$C_6$ trifluoroalkyl, preferably a trifluoromethyl,
    a heteroaryl fragment optionally substituted with a $C_1$-$C_6$ alkyl, a $C_1$-$C_6$ trifluoroalkyl, a halogen and/or a hydroxyl, wherein said heteroaryl fragment is chosen from a group consisting of dihydrobenzofuran, indol, benzodioxol, benzotriazol, pyridine and a thiazol preferably monosubstituted by a methyl,
    imidazol to the condition that Y is HNC(S), $HNSO_2$, $HNC(O)CH_2$, HNC(O)NH, HNC(S)NH, C(O)N-$HCH_2$, $CH_2NHC(O)$, $CH_2NHC(S)$ or C(O)NH wherein NH is directly linked to R3, preferably to the condition that Y is HNC(S), $HNSO_2$, HNC(O)$CH_2$, HNC(O)NH, HNC(S)NH, C(O)NH$CH_2$, $CH_2NHC(O)$ or $CH_2NHC(S)$, more preferably to the condition that Y is HNC(S),
  a heteroaryl group preferably chosen from a group consisting of dihydrobenzofuran, indol, benzodioxol, benzotriazol, pyridine, optionally substituted with a $C_1$-$C_6$ alkyl, a $C_1$-$C_6$ trifluoroalkyl, a halogen and/or a hydroxyl,
  non aromatic monosubstituted cyclic group, preferably a cyclic $C_3$-$C_{10}$ alkyl, monosubstituted with a hydroxyl, a halogen, a $C_1$-$C_6$ alkyl-amine, a $C_1$-$C_6$ alkoxy, a $C_1$-$C_6$ trifluoroalkoxy, a $C_1$-$C_6$ alkyl, a $C_1$-$C_6$ trifluoroalkyl and
  a fragment is chosen from a group consisting of:

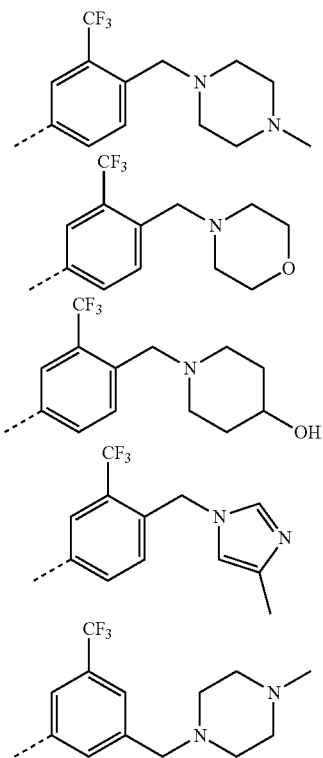

-continued

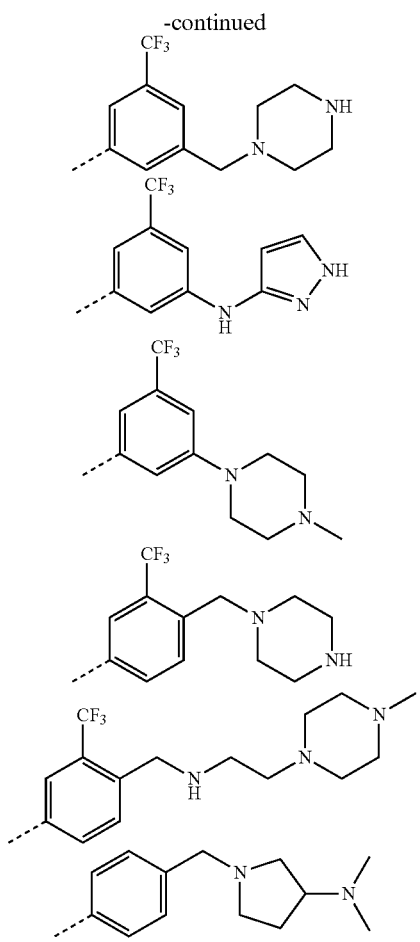

and/or the pharmaceutically acceptable addition salts, solvates, enantiomers, diastereoisomers thereof, as well as mixtures thereof.

Another aspect of the present invention concerns a method of preparation of the compounds as defined herein, characterized in that it comprises at least one of the following steps:
- a) in the case of X being CO, the NH—CO bond is formed by means of peptide coupling techniques with an aromatic carboxylic acid substituted with an $NO_2$ group, preferably by the use of a carbodiimide or an uronium coupling agent, or if X is $CH_2$, the NH—$CH_2$ bond is formed by a reductive amination with an aromatic aldehyde substituted with an $NO_2$ group, preferably in the presence of a boron hydride,
- b) reduction of the $NO_2$ group into $NH_2$, preferably by hydrogenation, such as a catalytic hydrogenation for example in the presence of palladium on charcoal under a hydrogen atmosphere.

Another aspect of the present invention concerns a method of preparation of the compounds as defined herein, characterized in that the method comprises one of the following steps, preferably after steps (a) and/or (b) of the above method:
- $c_1$) formation of a urea in the case of Y being HNC(O)NH, by reacting the compound obtained after step b) with an isocyanate,
- c2) formation of a thiourea in the case of Y being HNC(S)NH, by reacting the compound obtained after step b) with an isothiocyanate,
- $c_3$) formation of a sulfonamide in the case of Y being $HNSO_2$, by reacting the compound obtained after step b) with a halogen sulfonyl, such as sulfonyl chloride,
- $c_4$) formation of an amide in the case of Y being HNCO or HNC(O)$CH_2$, by reacting the compound obtained after step b) with a carboxylic acid using peptide coupling techniques or an acyl chloride, or
- $c_5$) formation of a thioamide in the case of Y being HNCS, by reacting the compound obtained after step c4) with the Lawesson's reagent.

Yet the present invention also relates to a compound as defined herein characterized in that it is a drug.

The present invention also relates to a compound as defined herein used as inhibitor of protein kinases in diseases such as cancers more particularly liquid tumors such as hematological cancers such as leukemias, chronic or acute myeloproliferative disorders or solid tumors such as squamous cell cancer, small-cell lung cancer, non-small cell lung cancer, gastrointestinal cancers, pancreatic cancer, glial cell tumors such as glioblastoma and neurofibromatosis, cervical cancer, ovarian cancer, liver cancer, bladder cancer, breast cancer, melanoma, colorectal cancer, endometrial carcinoma, salivary gland carcinoma, renal cancer, prostate cancer, vulval cancer, thyroid cancer, sarcomas and/or astrocytomas and other kinases related diseases preferably immune disorders, inflammatory diseases, thrombotic diseases, neurodegenerative diseases, bone diseases, macular degeneration, fibrosis, cystogenesis, hyperproliferative diseases.

The present invention also concerns a pharmaceutical composition, characterized in that it contains, as active principle, a compound as defined herein and a pharmaceutical acceptable excipient.

DEFINITIONS

In general, the following definitions are used:

The expression "peptide coupling" in the present invention means the reaction which enables to form an amide —NH—C(O)—. However the techniques used in this reaction are common in peptide syntheses, i.e. by activating a carboxylic acid in order to enable an amine to react onto it. Therefore, although no peptide is formed in the present invention, the coupling reactions are derived from peptide synthesis, and directly applicable to the subject matter of the present invention.

The coupling reactions may be carried out by employing a condensing reagent such as N,N'-dicyclohexylcarbodiimide (DCC) or 1-ethyl-3-(3'-dimethylaminopropyl) carbodiimide hydrochloride (EDC), i.e. water-soluble carbodiimide, O-(1H-benzotriazol-1-yl)-N,N,N',N'-tetramethyluronium tetrafluoroborate (TBTU), benzotriazol-1-yl-oxytris(dimethylamino)phosphonium hexafluorophosphate (BOP), O-(7-azabenzotriazol-1-yl)-1,2,3-tetramethyluronium hexafluorophosphate (HATU), O-benzotriazol-1-yl-N,N,N',N'-tetramethyluronium hexafluorophosphate (HBTU), O-benzotriazol-1-yl-tetramethyltetrafluoroborate (TBTU), N-hydroxy-5-norbornene-2,3-dicarbodiimide, or any other coupling agent in a solvent such as ether, acetone, chloroform, dichloromethane, ethyl acetate, DMF, tetrahydrofuran (THF), acetonitrile, dimethylsulfoxide (DMSO), N-methyl pyrrolidinone (NMP), under ice-cooling or at room temperature, preferably in the presence of an acylation catalyst such as dimethylaminopyridine (DMAP), pyridine, N-hydroxybenzotriazole (HOBt), 1-hydroxy-7-azabenzotriazole (HOAt), N-hydroxysuccinimide and the like.

The expression "alkyl group" in the present invention means a linear or branched saturated aliphatic group with 1 to 6 carbon atoms, if it is not specified. Examples of alkyl groups covered by the scope of the present invention are methyl, ethyl, propyl, butyl, tert-butyl, isopropyl groups, etc.

The expression "cycloalkyl group" in the present invention means a cyclic alkyl group with 3 to 10 carbon atoms. Examples of cycloalkyl groups covered by the scope of the present invention are cyclopropyl, cyclobutyl, cyclopentyl, cyclohexyl, methylcyclohexyl, etc.

The expression "aryl group" in the present invention means a cyclic (mono- or polycyclic) aromatic group comprising between 5 and 10 carbon atoms. Examples of aryl groups covered by the scope of the present invention are phenyl, naphthyl, etc.

The expression "heteroaryl group" in the present invention means a cyclic (mono- or polycyclic) aromatic group comprising between 5 and 10 carbon atoms and between 1 and 3 heteroatoms, such as nitrogen, oxygen or sulphur. Examples of heteroaryl groups covered by the scope of the present invention are pyridine, thiophene, thiazole, imidazole, pyrazole, pyrrole, quinoline, indole, pyridazine, quinoxaline, dihydrobenzofuran etc.

The expression "non aromatic monosubstituted cyclic group" in the present invention means cycloalkyl groups and/or heterocyclic groups.

The expression "heterocyclic group" in the present invention means a saturated cyclic group comprising between 5 and 10 carbon atoms, preferably 2 to 10, and between 1 and 3 heteroatoms, such as nitrogen, oxygen and sulphur. Examples of heterocyclic groups covered by the scope of the present invention are morpholines, tetrahydrofurans, etc.

The expression "halogen atom" in the present invention means: fluorine, chlorine, bromine or iodine atoms.

The expression "alkoxy group" in the present invention means an alkyl group bound to an oxygen. Examples of alkoxy groups covered by the scope of the present invention are methoxy, ethoxy groups etc.

The expression "aryloxy group" in the present invention means an aryl group bound to an oxygen atom. Examples of aryloxy groups covered by the scope of the present invention are phenyloxy, etc.

The expression "sulphonamide group" in the present invention means:

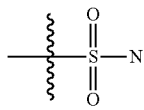

The expression "N-methyl sulphonamide group" in the present invention means:

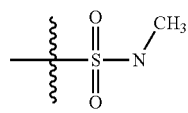 [SMILES: *S(=O)(=O)NC]

The expression "methanesulphonamide group" in the present invention means:

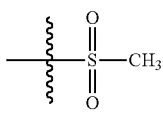 [SMILES: *S(C)(=O)=O]

The expression "aralkyl group" in the present invention means an alkyl group substituted with an aryl group:

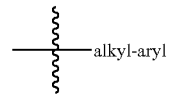

The expression "$C_1$-$C_6$ alkyl amine group" in the present invention means a $C_1$-$C_6$ alkyl group substituted with an amine group:

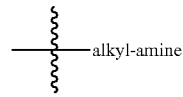

The expression "secondary $C_1$-$C_6$ alkyl amine group" means a secondary amine, i.e. which can be substituted by two $C_1$-$C_6$ alkyl groups.

The expression "hydroxyl group" in the present invention means: OH

The expression "alkoxyalkyl group" in the present invention means an alkyl group, preferably a substituted with an alkoxy group:

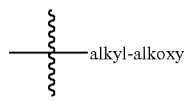

The expression "sulphanyl group" in the present invention means:

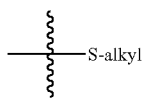

The expression "ureido" in the present invention is used as a general term for a urea or thiourea.

The expression "substituted phenyl" in the present invention means a phenyl mono- or poly-substituted with:
a halogen atom,
a nitro group —($NO_2$),
a cyano group (CN),
a methylthiazyl group,

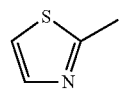

an alkoxy group,
an aryloxy group,
an alkyl group,
a sulphonamide group,
an N-methyl sulphonamide group,
a methanesulphonamide group,
a heteroaryl group,
a hydroxyl group,
a tertiary amine group,
a group —CONHalkyl,
a group —NHCOalkyl, The term "pyridyl" in the present invention means a radical derived from pyridine:

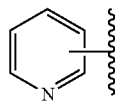

The term "thiophenyl" in the present invention means a radical derived from thiophene:

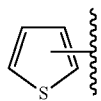

The term "thiazyl" in the present invention means a radical derived from thiazole:

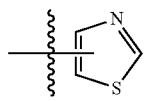

The term "imidazyl" in the present invention means a radical derived from imidazole:

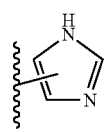

The term "pyrazyl" in the present invention means a radical derived from pyrazole:

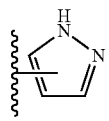

The term "quinoxaline" in the present invention means:

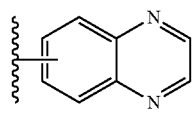

The term "dihydrobenzofuranyl" in the present invention means radical derived from dihydrobenzofuran:

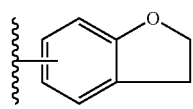

The term "pyrryl" in the present invention means radical derived from pyrrole:

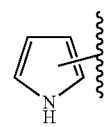

The term "indyl" in the present invention means a radical derived from indole:

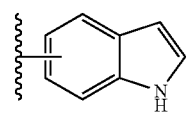

The term "pyridazinyl" in the present invention means radical derived from pyridazine:

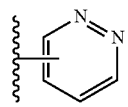

The term "N-morpholyl" in the present invention means radical derived from morpholine:

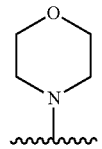 [SMILES: *N1CCOCC1]

The term "benzimidazyl" in the present invention means radical derived from benzimidazole:

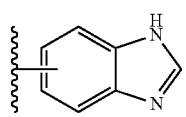

The term "pyrimidinyl" in the present invention means radical derived from pyrimidine:

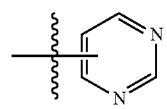

The expression "1H-pyrrolo[2,3-b]pyridyl" in the present invention means a radical derived from 1H-pyrrolo[2,3-b]pyridine:

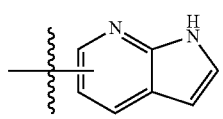

The expression "pharmaceutical composition" in the present invention means any composition comprising an effective dose of a compound of the invention and at least one pharmaceutically acceptable excipient. Said excipients are selected, depending on the pharmaceutical form and the desired method of administration, from the usual excipients known by a person skilled in the art.

The expression "pharmaceutically acceptable addition salts" in the present invention means all the pharmaceutically acceptable salts of the compounds according to the invention are included within the scope of the invention, in particular the salts of weak acids and of weak bases, for example the hydrochloride salt, hydrobromide salt, trifluoacetate salt etc.

The expression "mixtures of enantiomers" in the present invention means any mixture of enantiomers. The mixtures can be racemic, i.e. 50/50% of each enantiomer in weight (w/w), or non-racemic, i.e. enriched in one or the other of the enantiomer so that the ratios w/w are between 50/50% and 75/25%, between 75/25% and 90/10% or above 95% of one enantiomer in comparison with the other.

The expression "mixtures of diastereoisomers" in the present invention means any mixture of diastereoisomers in any proportions.

The expression "treatment" is intended to be directed towards all types of animals, preferably mammals, more preferably humans. In the case of a treatment of an animal which is not human kind, it will be referred to a veterinary treatment.

DETAILED DESCRIPTION OF THE PREFERRED EMBODIMENTS

Products

According to one embodiment, the compound (I) of the present invention is characterized in that,
R3 is chosen from a group consisting of:
  a phenyl group mono or polysubstituted with:
    a hydroxyl,
    a halogen,
    a $C_1$-$C_6$ alkyl-amine, preferably a secondary $C_1$-$C_6$ alkyl-amine,
    a $C_1$-$C_6$ alkoxy,
    a $C_1$-$C_6$ trifluoroalkoxy, preferably a trifluoromethoxy,
    a $C_1$-$C_6$ alkyl, preferably a methyl, isopropyl,
    a $C_1$-$C_6$ trifluoroalkyl, preferably a trifluoromethyl,
    a heteroaryl fragment optionally substituted with a $C_1$-$C_6$ alkyl, a $C_1$-$C_6$ trifluoroalkyl, a halogen and/or a hydroxyl, wherein said heteroaryl fragment is chosen from a group consisting of dihydrobenzofuran, indol, benzodioxol, benzotriazol, pyridine or a thiazol preferably monosubstituted by a methyl, and/or,
    imidazol to the condition that Y is HNC(S),
  a heteroaryl group preferably chosen from a group consisting of dihydrobenzofuran, indol, benzodioxol, benzotriazol, pyridine optionally substituted with a $C_1$-$C_6$ alkyl, a $C_1$-$C_6$ trifluoroalkyl, a halogen and/or a hydroxyl,
  non aromatic monosubstituted cyclic group, preferably a cyclic $C_3$-$C_{10}$ alkyl, monosubstituted with a hydroxyl, a halogen, a $C_1$-$C_6$ alkyl-amine, a $C_1$-$C_6$ alkoxy, a $C_1$-$C_6$ trifluoroalkoxy, a $C_1$-$C_6$ alkyl, a $C_1$-$C_6$ trifluoroalkyl, and
  a fragment is chosen from a group consisting of:

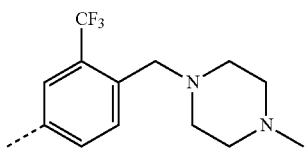

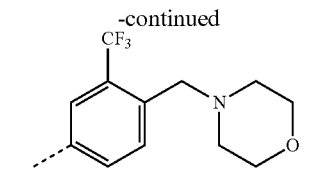

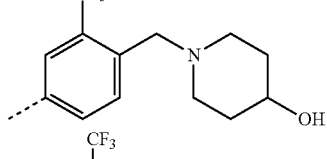

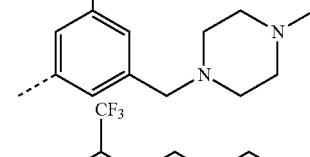

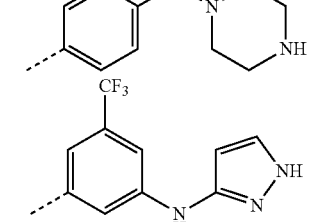

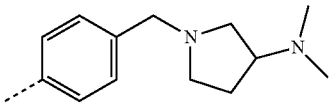

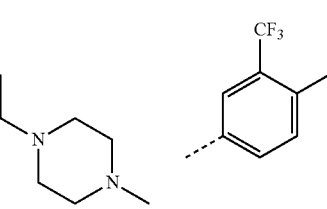

Advantageously, the compound (I) of the present invention is characterized in that,
X is $CH_2$,
R2 is an $C_1$-$C_6$ alkyl or a halogen,
and R1, Y and R3 are as defined above.

According to one embodiment, the compound (I) of the present invention is characterized in that,
X is $CH_2$,
R2 is an $C_1$-$C_6$ alkyl or a halogen, and
R3 is chosen from a group consisting of:
  a phenyl group mono or polysubstituted with:
    a hydroxyl,
    a halogen,
    a $C_1$-$C_6$ alkyl-amine, preferably a secondary $C_1$-$C_6$ alkyl-amine,
    a $C_1$-$C_6$ alkoxy,
    a $C_1$-$C_6$ trifluoroalkoxy, preferably a trifluoromethoxy,
    a $C_1$-$C_6$ alkyl, preferably a methyl, isopropyl,
    a $C_1$-$C_6$ trifluoroalkyl, preferably a trifluoromethyl,
    a heteroaryl fragment optionally substituted with a $C_1$-$C_6$ alkyl, a $C_1$-$C_6$ trifluoroalkyl, a halogen and/or a hydroxyl, wherein said heteroaryl fragment is chosen from a group consisting of dihydrobenzofuran, indol, benzodioxol, benzotriazol, pyridine or a thiazol preferably monosubstituted by a methyl,
    imidazol to the condition that Y is HNC(S), a heteroaryl preferably chosen from a group consisting of dihydrobenzofuran, indol, benzodioxol, benzotriazol, pyridine optionally substituted with a $C_1$-$C_6$ alkyl, a $C_1$-$C_6$ trifluoroalkyl, a halogen and/or a hydroxyl, more preferably a thiazol optionally monosubstituted by a methyl, non aromatic monosubstituted cyclic group, preferably a cyclic $C_3$-$C_{10}$ alkyl, monosubstituted with a hydroxyl, a halogen, a $C_1$-$C_6$ alkyl-amine, a $C_1$-$C_6$ alkoxy, a $C_1$-$C_6$ trifluoroalkoxy, a $C_1$-$C_6$ alkyl, a $C_1$-$C_6$ trifluoroalkyl, and a fragment is chosen from a group consisting of:

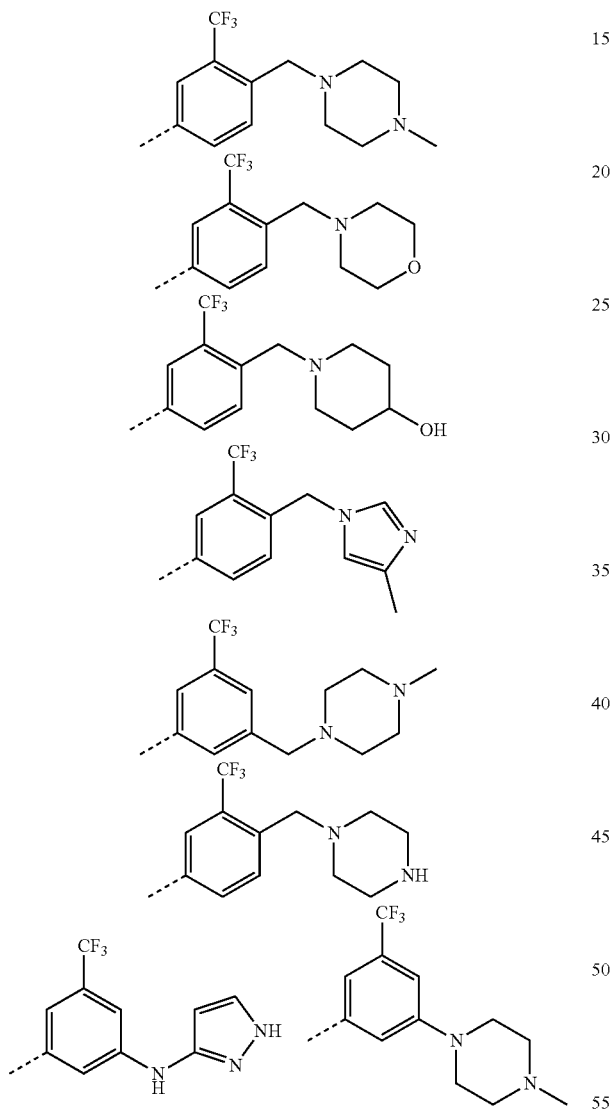

and R1 and Y are as defined above.

Advantageously, the compound (I) of the present invention is characterized in that, R1 is $C_1$-$C_6$ alkyl, preferably methyl or n-propyl, alternatively R1 is hydrogen, X is $CH_2$, R2 is a methyl, a fluorine or a chloride atom, preferably a methyl or a chloride atom, Y is chosen from a group consisting of HNC(O), HNC(O)$CH_2$, HNC(O)NH, HNC(S)NH, C(O)NH, C(O)NHCH_2, and $CH_2$NHC(O), R3 is chosen from a group consisting of:

a phenyl group mono substituted with a $C_1$-$C_6$ trifluoroalkyl group, a $C_1$-$C_6$ trifluoroalkoxy group, a $C_1$-$C_6$ alkyl group, a halogen, or a thiazol group optionally monosubstituted by a $CF_3$ and/or a methyl group, a phenyl group polysubstituted with a $C_1$-$C_6$ trifluoroalkyl, a $C_1$-$C_6$ alkyl-amine, and/or a hydroxyl group, a pyridine group, optionally substituted with a $C_1$-$C_6$ alkyl or a $C_1$-$C_6$ trifluoroalkyl, preferably methyl and/or a trifluoromethyl, non aromatic cyclic group chosen between a cyclic $C_3$-$C_{10}$alkyl, monosubstituted with a $C_1$-$C_6$ alkyl and/or a $C_1$-$C_6$ trifluoroalkyl, and a fragment chosen from a group consisting of:

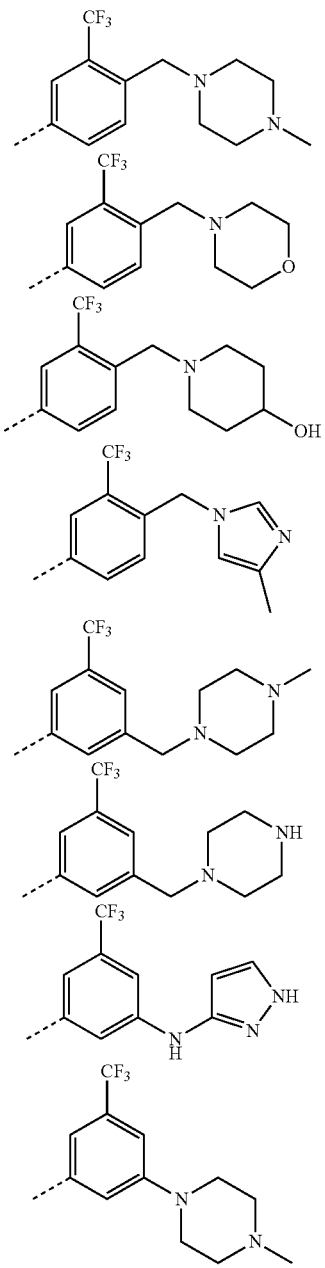

-continued

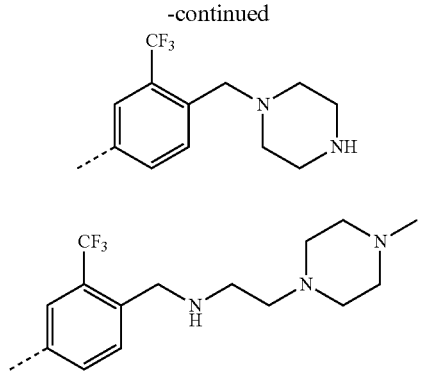

Even more advantageously, the compound (I) is characterized in that,

R1 is a $C_1$-$C_6$ alkyl group, preferably methyl, ethyl or n-propyl, alternatively, R1 is a hydrogen atom, X is a $CH_2$, R2 is methyl, Y is HNC*(O), wherein C* is linked to R3 and R3 is chosen from a group consisting of:

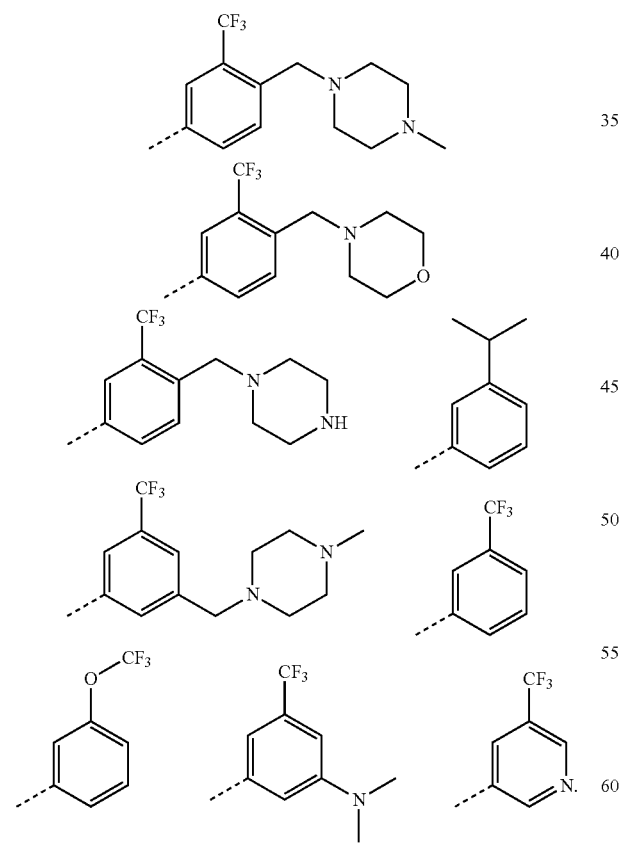

According to a preferred embodiment of the invention, the compound of formula (I) is specifically defined by the compound of formula (II):

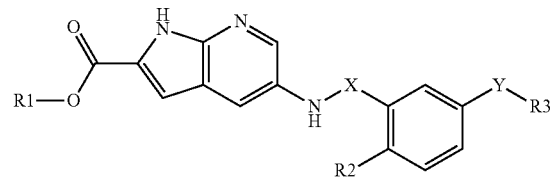

characterized in that,

R1 is a $C_1$-$C_6$ alkyl, alternatively, R1 is a hydrogen atom,

X is $CH_2$ or C=O,

R2 is hydrogen, a $C_1$-$C_6$ alkyl or a halogen,

Y is chosen from a group consisting of HNC(O), HNC(S), $HNSO_2$, $HNC(O)CH_2$, HNC(O)NH, HNC(S)NH, C(O)NH, $C(O)NHCH_2$, $CH_2NHC(O)$ and $CH_2NHC(S)$, R3 is chosen from a group consisting of:
  a phenyl group mono or polysubstituted with:
    a hydroxyl,
    a halogen,
    a $C_1$-$C_6$ alkyl-amine, preferably a secondary $C_1$-$C_6$ alkyl-amine,
    $C_1$-$C_6$ alkoxy,
    a $C_1$-$C_6$ trifluoroalkoxy, preferably a trifluoromethoxy,
    a $C_1$-$C_6$ alkyl, preferably a methyl, isopropyl,
    a $C_1$-$C_6$ trifluoroalkyl, preferably a trifluoromethyl,
    a heteroaryl fragment optionally substituted with a $C_1$-$C_6$ alkyl, a $C_1$-$C_6$ trifluoroalkyl, a halogen and/or a hydroxyl, wherein said heteroaryl fragment is chosen from a group consisting of dihydrobenzofuran, indol, benzodioxol, benzotriazol, pyridine or a thiazol preferably monosubstituted by a methyl, and/or
    imidazol to the condition that Y is HNC(S),
  a heteroaryl preferably chosen from a group consisting of dihydrobenzofuran, indol, benzodioxol, benzotriazol, pyridine optionally substituted with a $C_1$-$C_6$ alkyl, a $C_1$-$C_6$ trifluoroalkyl, a halogen and/or a hydroxyl, more preferably a thiazol optionally monosubstituted by a methyl,
  non aromatic monosubstituted cyclic group, preferably a cyclic $C_3$-$C_{10}$ alkyl, monosubstituted with a hydroxyl, a halogen, a $C_1$-$C_6$ alkyl-amine, a $C_1$-$C_6$ alkoxy, a $C_1$-$C_6$ trifluoroalkoxy, a $C_1$-$C_6$ alkyl, a $C_1$-$C_6$ trifluoroalkyl, and
  a fragment is chosen from a group consisting of:

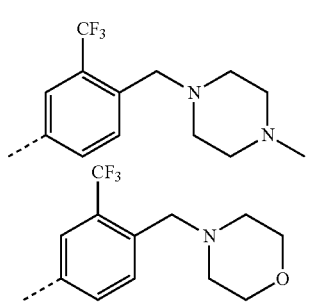

-continued

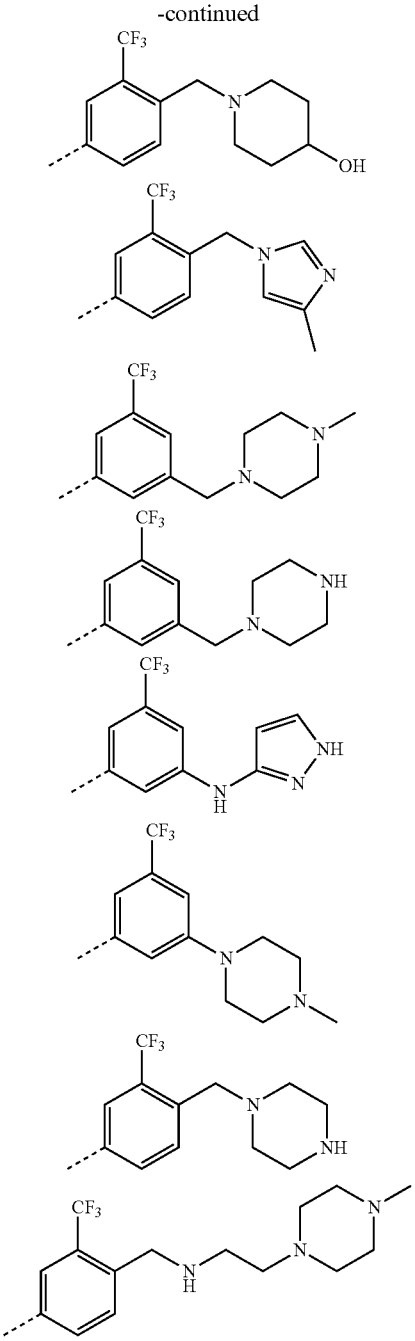

and/or the pharmaceutically acceptable addition salts, enantiomers, diastereoisomers thereof, as well as mixtures thereof.

According to a preferred embodiment of the invention, the compound of formula (II):

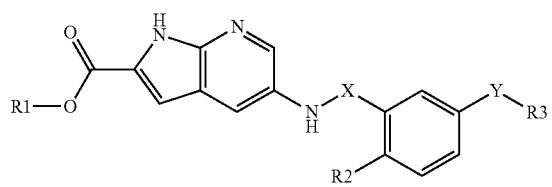

(II)

is characterized in that,
R1 is a methyl,
alternatively, R1 is a hydrogen atom,
X is a CH$_2$,
R2 is methyl,
Y is HNC*(O), wherein C* is linked to R3 and
R3 is chosen from a group consisting of:

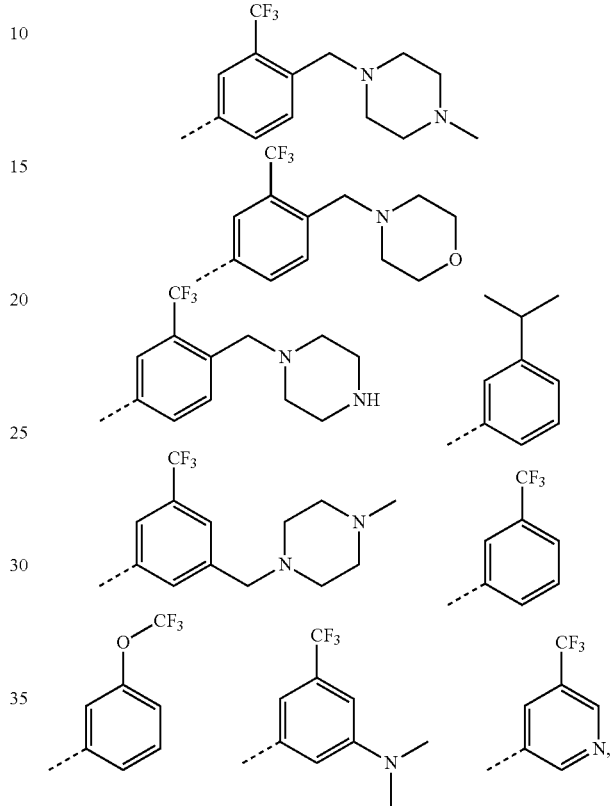

preferably R3 is:

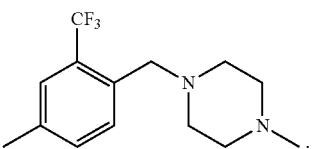

In another embodiment of the present invention, all the specific embodiments detailed above can also be characterized in that X instead of being CH$_2$ is C=O.

All the compounds of formula (I) or (II) disclosed here can be the pharmaceutically acceptable addition salts, enantiomers, diastereoisomers thereof, as well as mixtures thereof.

All the compounds according to the invention can be in solvated form and in non-solvated form.

Product Synthesis

The present invention also relates to the preparation methods of the here-above compounds starting from 5-amino-1H-pyrrolo[2,3-b]pyridine-2-carboxylic acid methyl ester.

In a first embodiment, the method according to the invention is represented in scheme 1. The general synthesis of the key intermediate amine compounds is indeed represented in Scheme 1:

Scheme 1

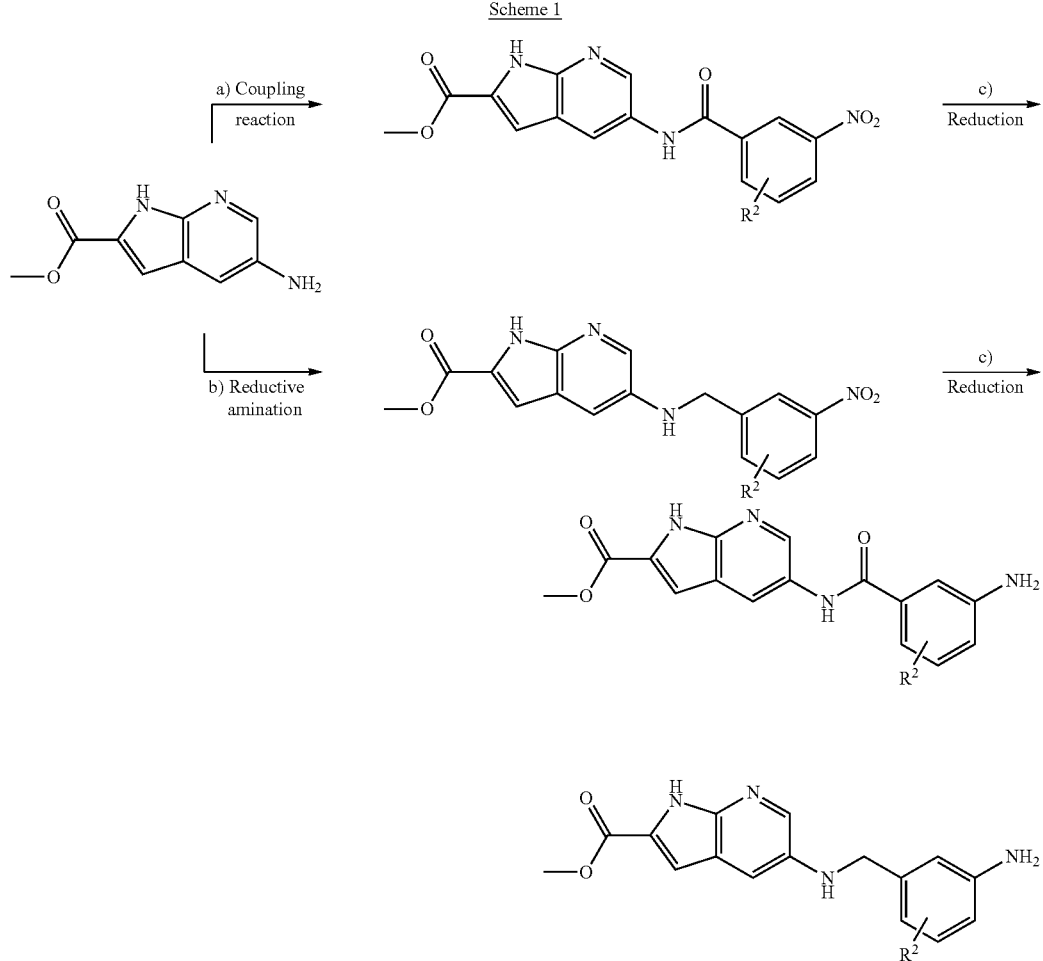

a) The method comprises at least one activating agent such as 2-(7-aza-1H-benzotriazol-1-yl)-N,N,N',N'-tetramethyluronium hexafluorophosphate (HATU) in the presence of a base such as diisopropylethylamine (DIEA), a carbodiimide such as dicyclohexylcarbodiimide (DCC).
These coupling reactions are well known by the skilled person in the art.

b) reductive amination of the 5-amino-1H-pyrrolo[2,3-b]pyridine-2-carboxylic acid methyl ester with various aromatic aldehydes in the presence of boron hydride to give corresponding benzylic amines (Wang, Dong Mei et al *Journal of Combinatorial Chemistry*, 2009, 11(4), 556-575)

c) catalytic hydrogenation of the resulting nitro compounds, in the presence of palladium on charcoal under hydrogen atmosphere (Seela, F., Gumbiowski, R. *Heterocycles*, 1989, 29 (4), 795-805).

Preferably the method comprises one or several of the following more specific steps a) b) c) in Scheme 2:

Scheme 2

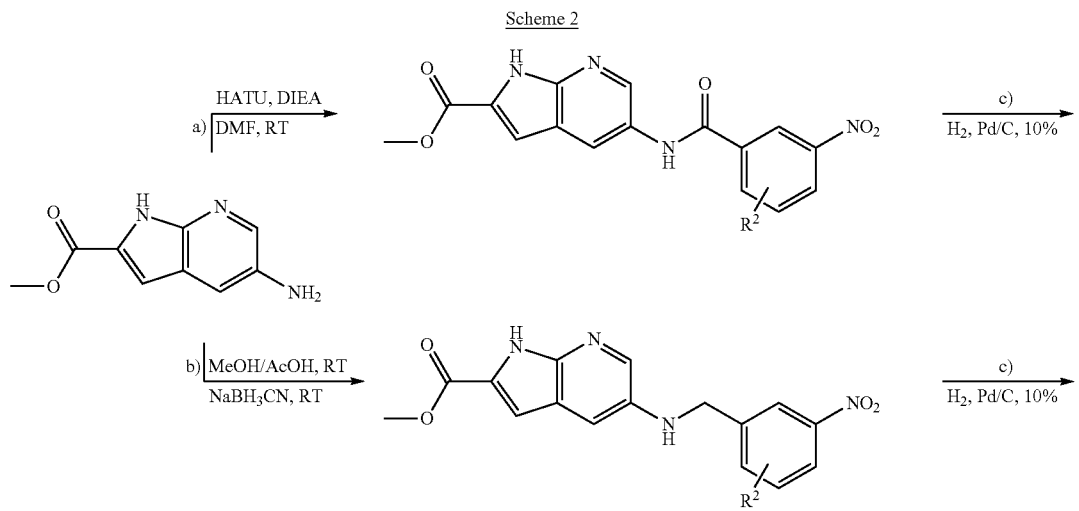

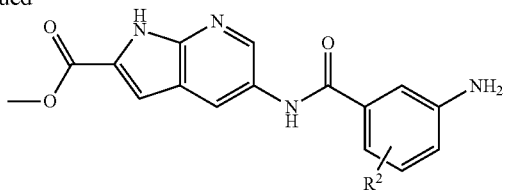

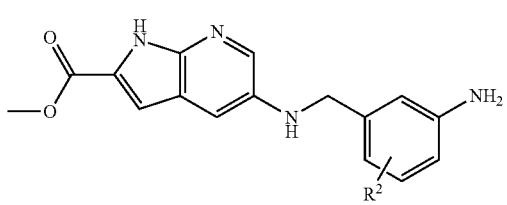

wherein R2 is as previously defined.

The preferred method comprises at least one of the following steps:
a) peptide coupling by means of 2-(7-aza-1H-benzotri-azol-1-yl)-N,N,N',N'-tetramethyluronium hexafluorophosphate (HATU) and diisopropylethylamine (DIEA),
b) reductive amination of the 5-amino-1H-pyrrolo[2,3-b]pyridine-2-carboxylic acid methyl ester with various aromatic aldehydes in the presence of boron hydride to give corresponding benzylic amines (Wang, Dong Mei et al *Journal of Combinatorial Chemistry*, 2009, 11(4), 556-575),
c) catalytic hydrogenation of the resulting nitro compounds, in the presence of palladium on charcoal under hydrogen atmosphere (Seela, F., Gumbiowski, R. *Heterocycles*, 1989, 29 (4), 795-805).

The skilled person in the art will naturally apply all other well-known synthesis techniques to obtain these types of compounds.

In another embodiment, the method is represented by scheme 3.

Concerning the method to synthesize the urea or thiourea compounds disclosed here-above, a method amongst other is represented in Scheme 3:

Scheme 3 wherein R2, R3 and X are as defined above, and Y is O or S.

The preferred method to synthesize the urea or thiourea compounds thus comprises at least a step of:
d) reaction of the key intermediate amine compound with various isocyanates or thioisocyanates.

The skilled person in the art will naturally apply all other well-known synthesis techniques to obtain these types of (thio)urea compounds.

In another embodiment, the method is represented by scheme 4.

Concerning the method to synthesize the sulfonamide compounds, a method amongst other is represented in Scheme 4:

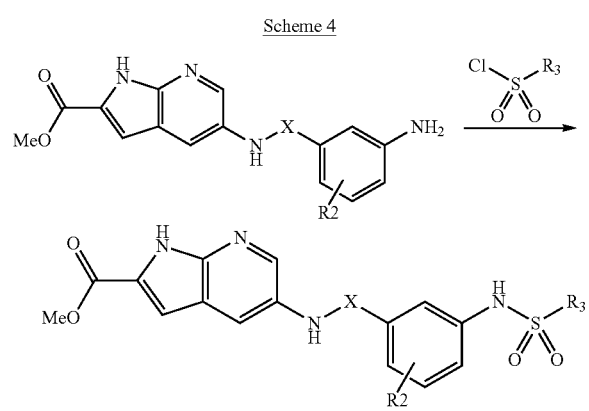

Scheme 4 wherein R2, R3 and X are as defined above.

This method to synthesize the sulfonamide compounds comprises at least a step of:
e) reaction of the key intermediate amine compound with various sulfonyl chloride.

The skilled person in the art will naturally apply all other well known synthesis techniques to obtain these types of sulfonamide compounds.

In another embodiment, the method is represented by scheme 5.

Concerning the method to synthesize the amide compounds, two methods amongst other are represented in Scheme 5:

Scheme 5

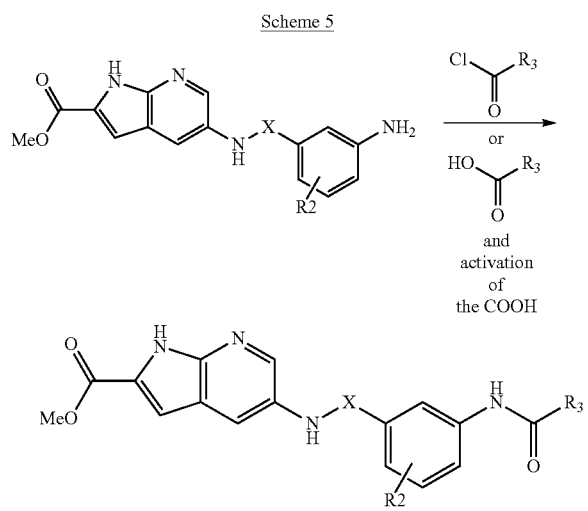

wherein R2, R3 and X are as defined above.

The methods of Scheme 5 comprise at least a step of:
f) reaction of the key intermediate amine compound with various acyl chlorides or carboxylic acids (Mouaddib, A., Joseph, B. et al., *Synthesis,* 2000, (4), 549-556).

The skilled person in the art will naturally apply all other well-known synthesis techniques to obtain these types of amide compounds.

In another embodiment, the method is represented by scheme 6.

Concerning the method to synthesize the thiourea compounds disclosed here-below, a method amongst other is represented in Scheme 6:

Scheme 6

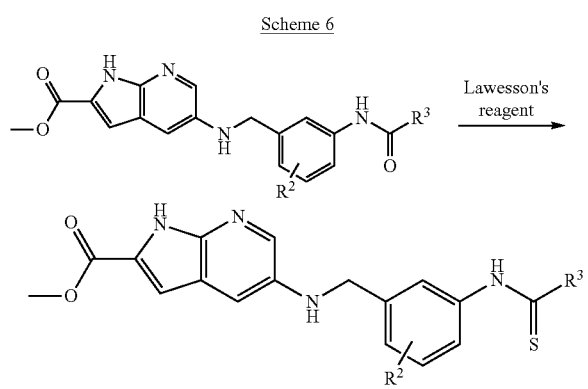

The preferred method to synthesize the thioamide compounds thus comprises at least a step of:
g) reaction of the key intermediate amide compound with Lawesson's reagent.

The sixth embodiment concerns the method to synthesize the non-commercially available carboxylic acids obtained according to the following Scheme 7, Scheme 8, Scheme 9 and/or Scheme 10.

4-aminomethyl-3-trifluoromethyl-benzoic acids or 4-aminomethyl-3-fluorobenzoic acids A method which was used in the present invention to synthesize 4-aminomethyl-3-trifluoromethyl-benzoic acids or 4-aminomethyl-3-fluorobenzoic acids, is represented by Scheme 7:

Scheme 7

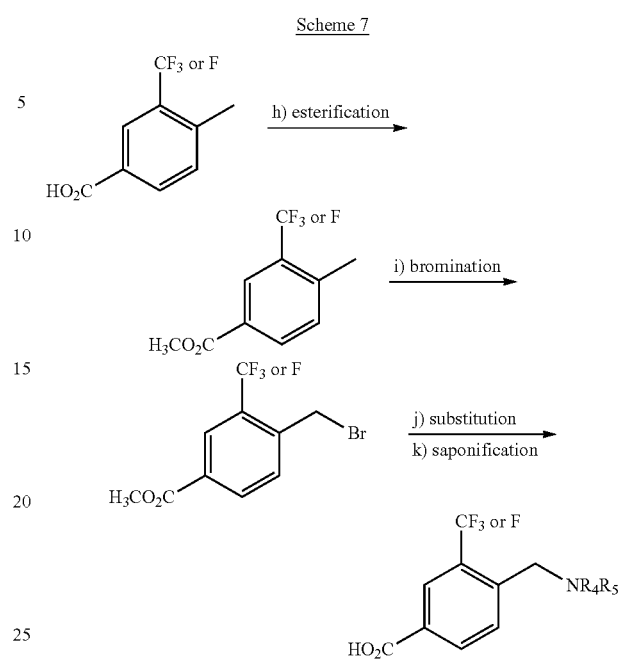

wherein $NR_4R_5$ represents:

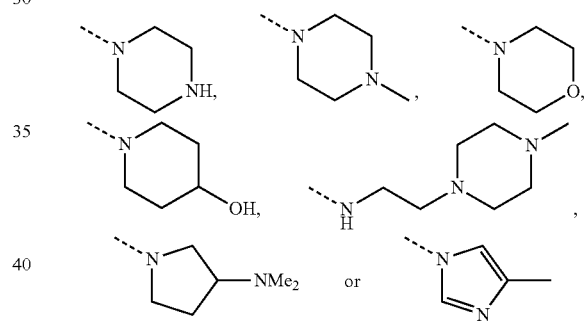

The preferred method to synthesize 4-aminomethyl-3-trifluoromethyl-benzoic acids and 4-aminomethyl-3-fluorobenzoic acids, comprises at least one of the following steps:
h) esterification of key 4-methyl-benzoic acids, preferably in methanol, advantageously in an acid medium to give the methylic ester,
i) radical bromination of the methyl group, preferably by N-bromosuccinimide (NBS), advantageously in presence of azobisisobutyronitrile (AIBN) as radical initiator (Sun, Yewei et al, *Bioorganic & Medicinal Chemistry,* 2008, 16(19), 8868-8874),
j) brome substitution by various primary and secondary amines,
k) saponification of the ester, preferably methylic ester.

The skilled person in the art will naturally apply all other well-known synthesis techniques to obtain 4-aminomethyl-3-trifluoromethyl-benzoic acids or 4-aminomethyl-3-fluorobenzoic acids, however several or even all steps g), h), i) and j) are preferably comprised in the method.

3-amino-5-trifluoromethyl-benzoic acids

A method to synthesize 3-amino-5-trifluoromethyl-benzoic acids is represented in Scheme 8:

Scheme 8

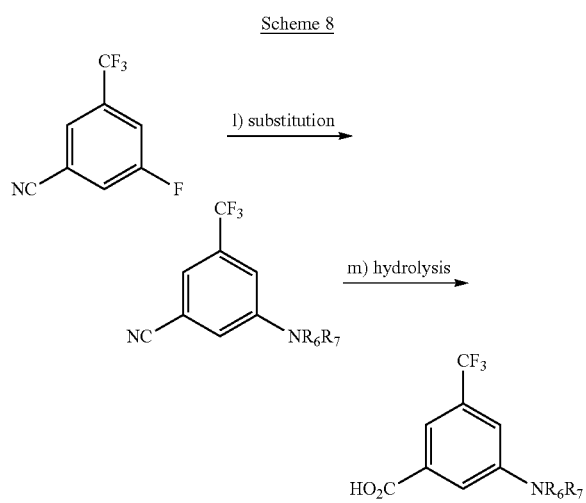

wherein NR₆R₇ represents:

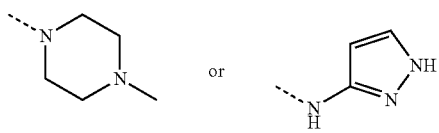

The preferred method to synthesize 3-amino-5-trifluoromethyl-benzoic acids comprises at least one of the following steps:
l) fluorine substitution by various primary and secondary amines,
m) hydrolysis of the nitrile function to the corresponding carboxylic acid.

The skilled person in the art will naturally apply all other well-known synthesis techniques to obtain 3-amino-5-trifluoromethyl-benzoic acids, however both steps l) and m) are preferably comprised in the method.

5-(4-methyl-piperazin-1-ylmethyl)-3-trifluoromethylbenzoic acid

The method which can be followed to synthesize 5-(4-methyl-piperazin-1-ylmethyl)-3-trifluoromethylbenzoic acid used in the present invention is represented in Scheme 9:

Scheme 9

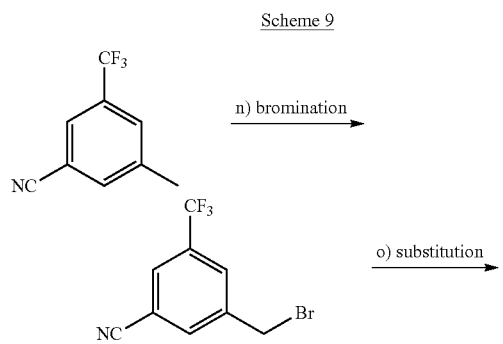

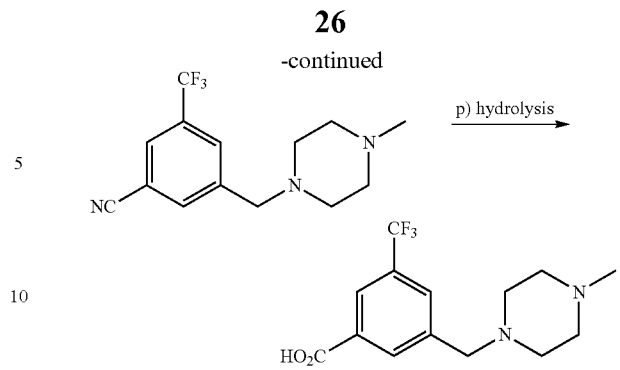

The method comprises at least one of the steps:
n) radical bromination of the methyl group by N-bromosuccinimide (NBS) in presence of Azobisisobutyronitrile (AIBN) as radical initiator (Sun, Yewei et al, *Bioorganic & Medicinal Chemistry*, 2008, 16(19), 8868-8874),
o) brome substitution by N-methylpiperazine,
p) hydrolysis of the nitrile function to the corresponding carboxylic acid.

The skilled person in the art will naturally apply all other well-known synthesis techniques to obtain 5-(4-methyl-piperazin-1-ylmethyl)-3-trifluoromethylbenzoic acid, however several or even all steps n), o) and p) are preferably comprised in the method.

3-dimethylamino-5-trifluoromethyl-benzoic acid

The method which can be followed to synthesize 3-dimethylamino-5-methyl-benzoic acid used in the present invention is represented in Scheme 10:

Scheme 10

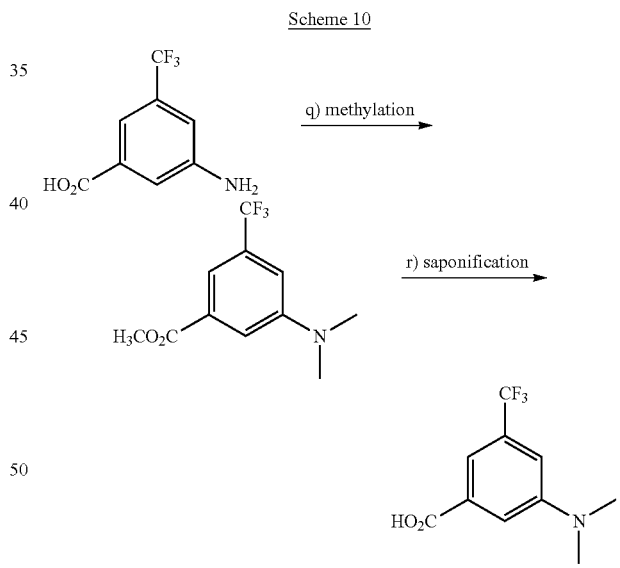

The method comprises at least one of the steps:
q) total methylation of the acid and amine functions, preferably by means of methyl iodide,
r) saponification of the resulting ester to give the corresponding carboxylic acid.

The skilled person in the art will naturally apply all other well-known synthesis techniques to obtain 3-dimethylamino-5-trifluoromethyl-benzoic acid, however one or both steps q) and r) are preferably comprised in the method.

Another embodiment concerns the method to synthesize 5-{2-Methyl-5-[4-(4-methyl-piperazin-1-ylmethyl)-3-trifluoromethylbenzoylamino]-benzylamino}-1H-pyrrolo[2,3-b]pyridine-2-carboxylic acid alkyl ester obtained according to the following Scheme 11:

Scheme 11

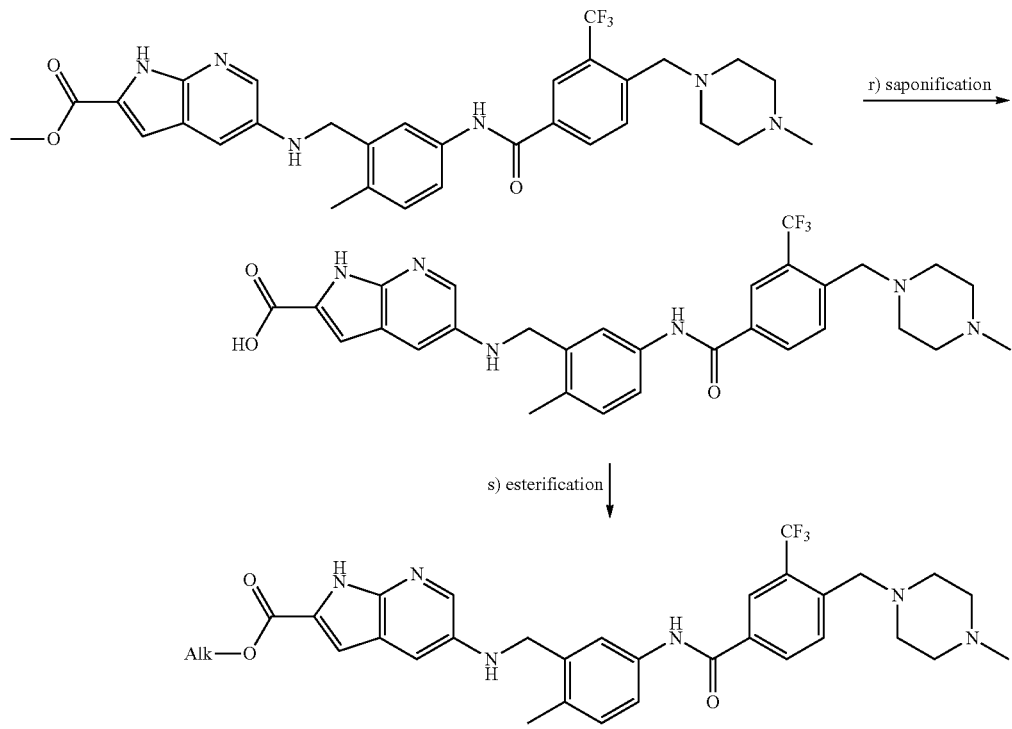

Preferably, the method comprises at least the following step:
- s) saponification of 5-{2-Methyl-5-[4-(4-methyl-piperazin-1-ylmethyl)-3-trifluoromethylbenzoylamino]-benzylamino}-1H-pyrrolo[2,3-b]pyridine-2-carboxylic acid methyl ester to afford it's carboxylic acid derivative,
- t) esterification of the resulting carboxylic acid by mean of thionyl chloride or sulfuric acid in alkyl-alcohol.

The skilled person in the art will naturally apply all other well-known synthesis techniques to obtain 5-{2-Methyl-5-[4-(4-methyl-piperazin-1-ylmethyl)-3-trifluoromethylbenzoylamino]-benzylamino}-1H-pyrrolo[2,3-b]pyridine-2-carboxylic acid alkyl ester, however one or both steps s) and t) are preferably comprised in the method.

Another embodiment concerns the method to synthesize 5-(3-{[4-(4-Methyl-piperazin-1-ylmethyl)-3-trifluoromethyl-benzoylamino]-methyl}-benzoylamino)-1H-pyrrolo[2,3-b]pyridine-2-carboxylic acid methyl ester or 5-{3-[(3-Trifluoromethyl-thiobenzoylamino)-methyl]-benzoylamino}-1H-pyrrolo[2,3-b]pyridine-2-carboxylic acid methyl ester obtained according the following Scheme 12:

Scheme 12

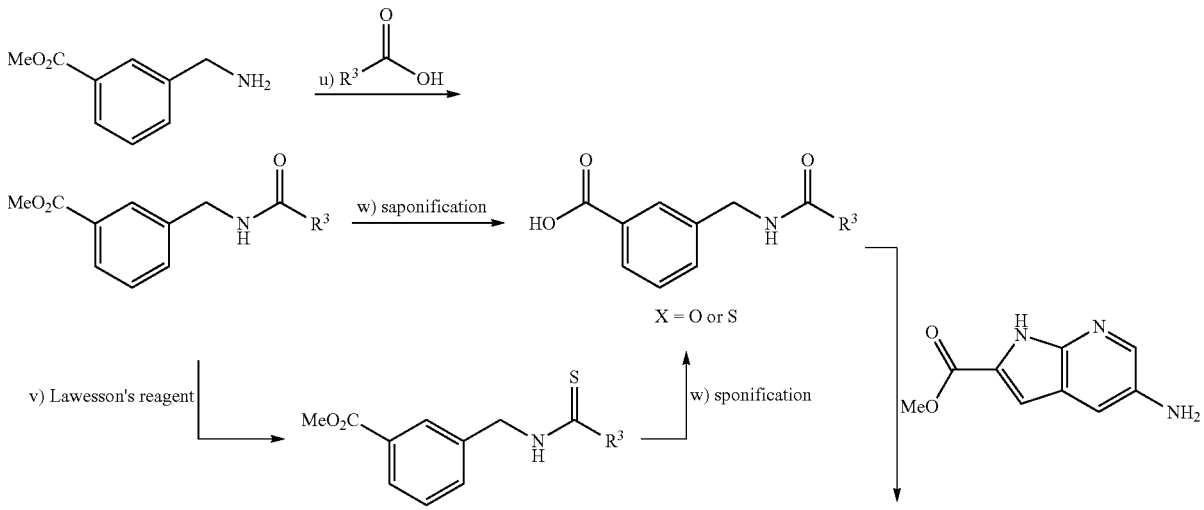

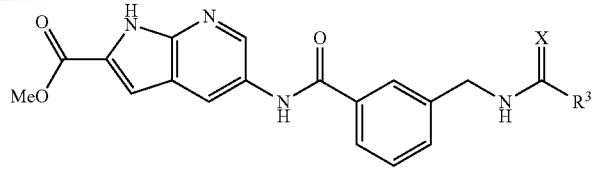

wherein R3 represents:

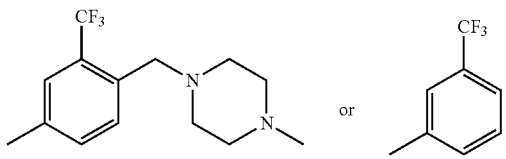

Preferably, the method comprises at least the following step:
u) peptide coupling reaction with the 3-Aminomethyl-benzoic acid methyl ester and a carboxylic acid,
v) reaction of the key intermediate amide compound with Lawesson's reagent,
w) saponification of the resulting ester to give the corresponding carboxylic acid,
x) peptide coupling reaction with the key carboxylic acid compound and the 5-amino-1H-pyrrolo[2,3-b]pyridine-2-carboxylic acid methyl ester.

Another embodiment concerns the method to synthesize 5-[3-(3-Trifluoromethyl-benzylcarbamoyl)-benzylamino]-1H-pyrrolo[2,3-b]pyridine-2-carboxylic acid methyl ester or 5-{3-[4-(4-Methyl-piperazin-1-ylmethyl)-3-trifluoromethyl-phenylcarbamoyl]-benzylamino}-1H-pyrrolo[2,3-b]pyridine-2-carboxylic acid methyl ester obtained according the following Scheme 13:

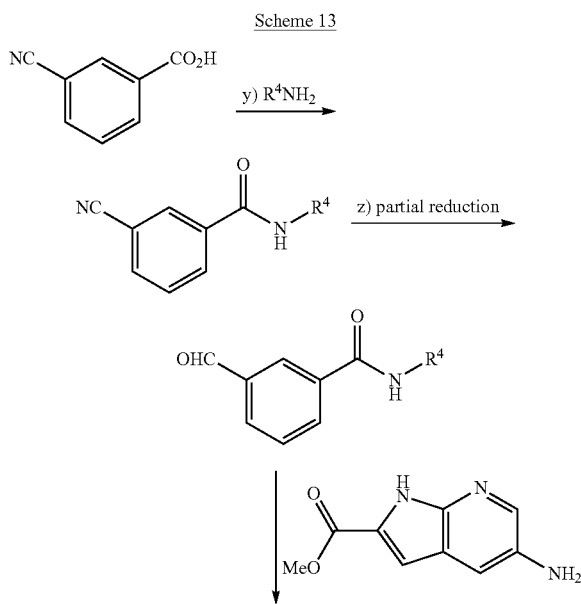

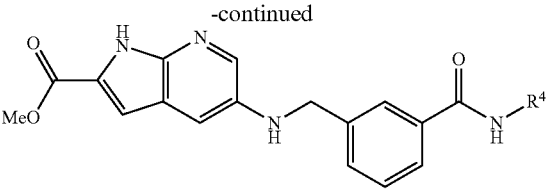

wherein R4 represents:

prepared according procedure described by Weijun Shen and al. (*J. Am. Chem. Soc.*, 2013, 135 (5), pp 1669-1672).

Preferably, the method comprises at least the following step:
y) peptide coupling reaction with the 3-Cyano-benzoic acid and an amine compound,
z) reduction of the resulting nitrile into the corresponding aldehyde,
aa) reductive amination of the key aldehyde compound with the 5-amino-1H-pyrrolo[2,3-b]pyridine-2-carboxylic acid methyl ester.

Uses

The present invention also relates to the use of the compounds according to the invention as inhibitors of protein kinases. Depending of the type of Cancer, one or several kinase proteins will be aimed.

In one embodiment, the compounds according to the invention are used as inhibitor of protein kinase BRAF.

In another embodiment, the compounds according to the invention are used as inhibitors of protein kinase EGFR (ErbB1).

In another embodiment, the compounds according to the invention are used as inhibitors of protein kinase EGFR (ErbB1) T790M L858R.

In another embodiment, the compounds according to the invention are used as inhibitors of protein kinase FGFR2.

In another embodiment, the compounds according to the invention are used as inhibitors of protein kinase KDR (VEGFR2).

In another embodiment, the compounds according to the invention are used as inhibitors of protein kinase PDGFRA (PDGFR alpha).

In another embodiment, the compounds according to the invention are used as inhibitors of protein kinase SRC.

In another embodiment, the compounds according to the invention are used as inhibitors of protein kinase ABL.

In another embodiment, the compounds according to the invention are used as inhibitors of protein kinase ABL T315I.

In another embodiment, the compounds according to the invention are used as inhibitors of protein kinase FGFR1.

In another embodiment, the compounds according to the invention are used as inhibitors of protein kinase VEGFR1.

In another embodiment, the compounds according to the invention are used as inhibitors of protein kinase PDGFRB (PDGFR beta).

In another embodiment, the compounds according to the invention are used as inhibitors of protein kinase ABL E255K.

In another embodiment, the compounds according to the invention are used as inhibitors of protein kinase ABL G250E.

In another embodiment, the compounds according to the invention are used as inhibitors of protein kinase ABL Y253F.

In another embodiment, the compounds according to the invention are used as inhibitors of protein kinase ABL2.

In another embodiment, the compounds according to the invention are used as inhibitors of protein kinase BLK.

In another embodiment, the compounds according to the invention are used as inhibitors of protein kinase BMX.

In another embodiment, the compounds according to the invention are used as inhibitors of protein kinase BRAF V600E.

In another embodiment, the compounds according to the invention are used as inhibitors of protein kinase BTK.

In another embodiment, the compounds according to the invention are used as inhibitors of protein kinase CSK.

In another embodiment, the compounds according to the invention are used as inhibitors of protein kinase EPHA1.

In another embodiment, the compounds according to the invention are used as inhibitors of protein kinase EPHA2.

In another embodiment, the compounds according to the invention are used as inhibitors of protein kinase EPHA4.

In another embodiment, the compounds according to the invention are used as inhibitors of protein kinase EPHB2.

In another embodiment, the compounds according to the invention are used as inhibitors of protein kinase EPHB4.

In another embodiment, the compounds according to the invention are used as inhibitors of protein kinase HER2.

In another embodiment, the compounds according to the invention are used as inhibitors of protein kinase ERBB4.

In another embodiment, the compounds according to the invention are used as inhibitors of protein kinase FES.

In another embodiment, the compounds according to the invention are used as inhibitors of protein kinase FGR.

In another embodiment, the compounds according to the invention are used as inhibitors of protein kinase FLT3.

In another embodiment, the compounds according to the invention are used as inhibitors of protein kinase FMS.

In another embodiment, the compounds according to the invention are used as inhibitors of protein kinase FRK.

In another embodiment, the compounds according to the invention are used as inhibitors of protein kinase FYN.

In another embodiment, the compounds according to the invention are used as inhibitors of protein kinase HCK.

In another embodiment, the compounds according to the invention are used as inhibitors of protein kinase LCK.

In another embodiment, the compounds according to the invention are used as inhibitors of protein kinase LYN.

In another embodiment, the compounds according to the invention are used as inhibitors of protein kinase MAPK14.

In another embodiment, the compounds according to the invention are used as inhibitors of protein kinase ERK2.

In another embodiment, the compounds according to the invention are used as inhibitors of protein kinase PKC theta.

In another embodiment, the compounds according to the invention are used as inhibitors of protein kinase RET.

In another embodiment, the compounds according to the invention are used as inhibitors of protein kinase VEGFR3.

In another embodiment, the compounds according to the invention are used as inhibitors of protein kinase YES.

In another embodiment, the compounds according to the invention are used as inhibitors of the proliferation of A549 cancer cell line.

In another embodiment, the compounds according to the invention are used as inhibitors of the proliferation of HepG2 cancer cell line.

In another embodiment, the compounds according to the invention are used as inhibitors of the proliferation of HuCCT1 cancer cell line.

In another embodiment, the compounds according to the invention are used as inhibitors of the proliferation of HuH6 Clone 5 cancer cell line.

In another embodiment, the compounds according to the invention are used as inhibitors the proliferation of HuH7 cancer cell line.

In another embodiment, the compounds according to the invention are used as inhibitors of the proliferation of PC-3 cancer cell line.

In another embodiment, the compounds according to the invention are used as inhibitors of the proliferation of Caki-2 cancer cell line.

In another embodiment, the compounds according to the invention are used as inhibitors of the proliferation of MDA-MB-231 cancer cell line.

In another embodiment, the compounds according to the invention are used as inhibitors of the proliferation of HT29 cancer cell line.

In another embodiment, the compounds according to the invention are used as inhibitors of the proliferation of BxPC-3 cancer cell line.

In another embodiment, the compounds according to the invention are used as inhibitors of the proliferation of H1975 cancer cell line.

In another embodiment, the compounds according to the invention are used as inhibitors of the proliferation of BaF3 WT.

In another embodiment, the compounds according to the invention are used as inhibitors of the proliferation of BaF3 T315I.

In another embodiment, the compounds according to the invention are used as inhibitors of the proliferation of BaF3 G250A.

In another embodiment, the compounds according to the invention are used as inhibitors of the proliferation of BaF3 G250E.

In another embodiment, the compounds according to the invention are used as inhibitors of the proliferation of BaF3 G250A+E279N.

In another embodiment, the compounds according to the invention are used as inhibitors of the proliferation of BaF3 E255K+M351T.

In another embodiment, the compounds according to the invention are used as inhibitors of the proliferation and migration of HUVEC primary cells.

In another embodiment, the compounds according to the invention are used as inhibitors of the proliferation and migration of HRMEC primary cells.

In another embodiment, the compounds according to the invention are used as inhibitors of the proliferation and migration of HeLa cancer cell line.

The compounds, and of course pharmaceutical compositions comprising such compounds, of the invention can be used in the treatment of pathologies associated with deregulation of protein kinases:
- in the case of immune disorders, inflammatory diseases, thrombotic diseases, neurodegenerative diseases, bone diseases, macular degeneration, fibrosis, cystogenesis, hyperproliferative diseases,
- in the case of all cancers more particularly liquid tumors such as hematological cancers such as leukemias, chronic or acute myeloproliferative disorders or solid tumors such as squamous cell cancer, small-cell lung cancer, non-small cell lung cancer, gastrointestinal cancers, pancreatic cancer, glial cell tumors such as glioblastoma and neurofibromatosis, cervical cancer, ovarian cancer, liver cancer, bladder cancer, breast cancer, melanoma, colorectal cancer, endometrial carcinoma, salivary gland carcinoma, renal cancer, prostate cancer, vulval cancer, thyroid cancer, sarcomas and/or astrocytomas,
- in the case of chronic or acute myeloproliferative disorders such as certain leukaemias,
- in the case of hepatic, lung, prostate, kidney, breast, pancreatic and colorectal gastrointestinal cancers.

Advantageously, the compounds of the invention, and of course pharmaceutical compositions comprising such compounds, can be used in the treatment of pathologies associated with deregulation of protein kinases in the case of diseases, wherein the diseases is selected from the group consisting of liver cancer, pancreatic cancer, lung cancer, breast cancer, prostate cancer, leukemias, renal cancer, endometrial cancer, colorectal cancer, chemoresistant cancers and macular degeneration.

According to another aspect, the invention relates to a medicinal product comprising a compound according to the invention as active principle. Thus, the compounds according to the invention can be used as medicinal products in the treatment of pathologies associated with deregulation of protein kinases:
- in the case of immune disorders, inflammatory diseases, thrombotic diseases, neurodegenerative diseases, bone diseases, macular degeneration, fibrosis, cystogenesis, hyperproliferative diseases,
- in the case of all cancers more particularly liquid tumors such as hematological cancers such as leukemias, chronic or acute myeloproliferative disorders or solid tumors such as squamous cell cancer, small-cell lung cancer, non-small cell lung cancer, gastrointestinal cancers, pancreatic cancer, glial cell tumors such as glioblastoma and neurofibromatosis, cervical cancer, ovarian cancer, liver cancer, bladder cancer, breast cancer, melanoma, colorectal cancer, endometrial carcinoma, salivary gland carcinoma, renal cancer, prostate cancer, vulval cancer, thyroid cancer, sarcomas and/or astrocytomas,
- in the case of chronic or acute myeloproliferative disorders such as certain leukemias,
- in the case of hepatic, lung, prostate, kidney, breast, pancreatic and colorectal gastrointestinal cancers.

The compositions according to the invention can be used in the treatment of pathologies associated with deregulation of protein kinases:
- in the case of immune disorders, inflammatory diseases, thrombotic diseases, neurodegenerative diseases, bone diseases, macular degeneration, fibrosis, cystogenesis, hyperproliferative diseases,
- in the case of all cancers more particularly liquid tumors such as hematological cancers such as leukemias, chronic or acute myeloproliferative disorders or solid tumors such as squamous cell cancer, small-cell lung cancer, non-small cell lung cancer, gastrointestinal cancers, pancreatic cancer, glial cell tumors such as glioblastoma and neurofibromatosis, cervical cancer, ovarian cancer, liver cancer, bladder cancer, breast cancer, melanoma, colorectal cancer, endometrial carcinoma, salivary gland carcinoma, renal cancer, prostate cancer, vulval cancer, thyroid cancer, sarcomas and/or astrocytomas.
- in the case of chronic or acute myeloproliferative disorders such as certain leukemias,
- in the case of hepatic, lung, prostate, kidney, breast, pancreatic and colorectal gastrointestinal cancers.

Moreover, in an advantageous way, the compounds according to the invention can be used for inhibiting cellular proliferation and/or angiogenesis involved in human or animal diseases.

In the same way, the compositions according to the invention can be used for inhibiting cellular proliferation and/or angiogenesis involved in human or animal diseases.

Another aspect of the present invention concerns an in vitro method (in vitro diagnostic device or an imaging tool) for providing information that is essential for the safe and effective use of the compounds according to present invention. As an example, the method will allow predicting whether a patient in need thereof, such as presenting cancer, is likely to respond to at least one of the compounds according to present invention, which method comprises determining the expression level, the gene modifications (amplification, mutation), the activation state or the appearance of a mutated form of the protein of at least one protein kinase in a sample of said patient, wherein said protein kinase is selected from the following list of kinases BRAF, EGFR, FGFR2, KDR, PDGFRA, SRC, ABL, FGFR1, VEGFR1, PDGFRB (PDGFR beta), ABL2, BLK, BMX, BTK, CSK, EPHA1, EPHA2, EPHA4, EPHB2, EPHB4, HER2, ERBB4, FES, FGR, FLT3, FMS, FRK, FYN, HCK, LCK, LYN, MAPK14, ERK2, PKC theta, RET, VEGFR3 and YES.

The expression levels, gene modifications (amplification, mutation), activation state or appearance of a mutated form of the protein kinase is classically determined by the usually known methods (see for example the in vitro and imaging tools of medical devices approved by the FDA: http://www.fda.gov/MedicalDevices/ProductsandMedicalProcedures/InVitroDiagnostics/ucm301431.htm) such as real-time PCR, imunohistochemistry, ELISA, fluorescence in situ hybridization (FISH), chromogenic in situ hybridization (CISH).

Another aspect of the present invention concerns an in vitro method for predicting the at least one compound according to the invention to be administered to a patient in need thereof, such as presenting a cancer, characterized in that it comprises the following steps:
a) putting into contact said compound(s) with a sample of human tissue or cells,
b) determination of the activity of the compound(s) on the sample via for example IC50 and/or via a compared activity of the protein kinases present, which can for example be chosen from the following list of kinases BRAF, EGFR, EGFR T790M L858R, FGFR2, KDR, PDGFRA, SRC, ABL, ABL T315I, FGFR1, VEGFR1, PDGFRB, ABL E255K, ABL G250E, ABL Y253F, ABL2, BLK, BMX, BRAF V600E, BTK, CSK, EPHA1, EPHA2, EPHA4, EPHB2, EPHB4, HER2, ERBB4, FES, FGR, FLT3, FMS, FRK, FYN, HCK, LCK, LYN, MAPK14, ERK2, PKC theta, RET, VEGFR3 and YES;

c) optionally conducting the same test as step a) with healthy cells such as hematological cells or stem cells or hepatic cells of said patient to determine the toxicity of the compound according to the present invention to healthy cells (i.e. not presenting any pathological aspects/properties);

d) selecting the compound according to the present invention presenting the best activity, and/or eventually lowest toxicity, to be administered to the patient in need thereof.

The methods to determine the activity of the protein kinases are classically known (as reported in Rosen et al., J Biol Chem., 15; 261(29), 13754-9. 1986; Ma et al., Expert Opin Drug Discov., 3(6), 607-621, 2008).

FIGURES

EXAMPLES

Figure 1:
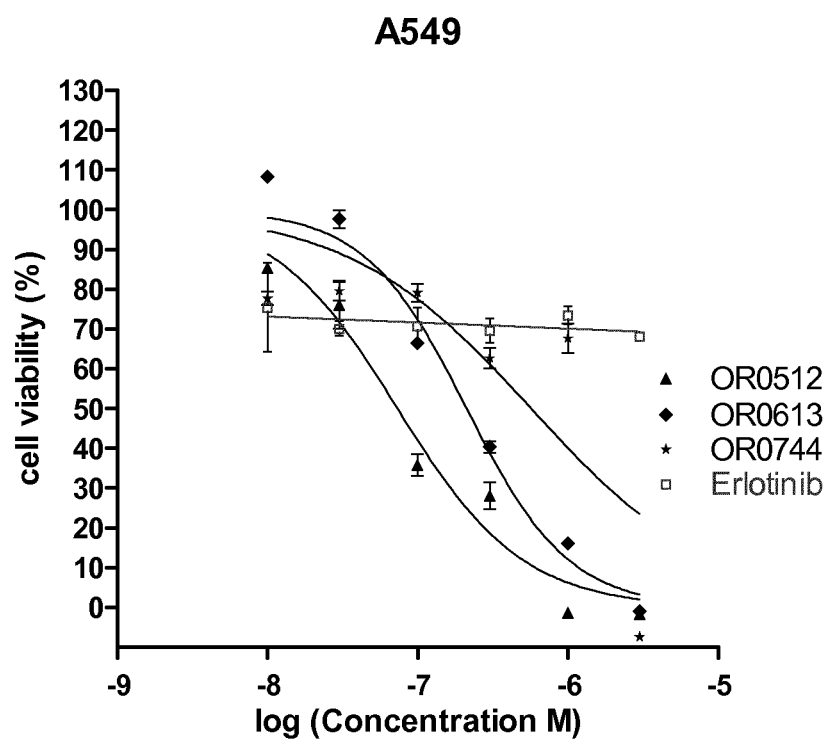
FIG. 1 is a graph representing anti-proliferative activity of some compounds on A549 cells.
Figure 2:
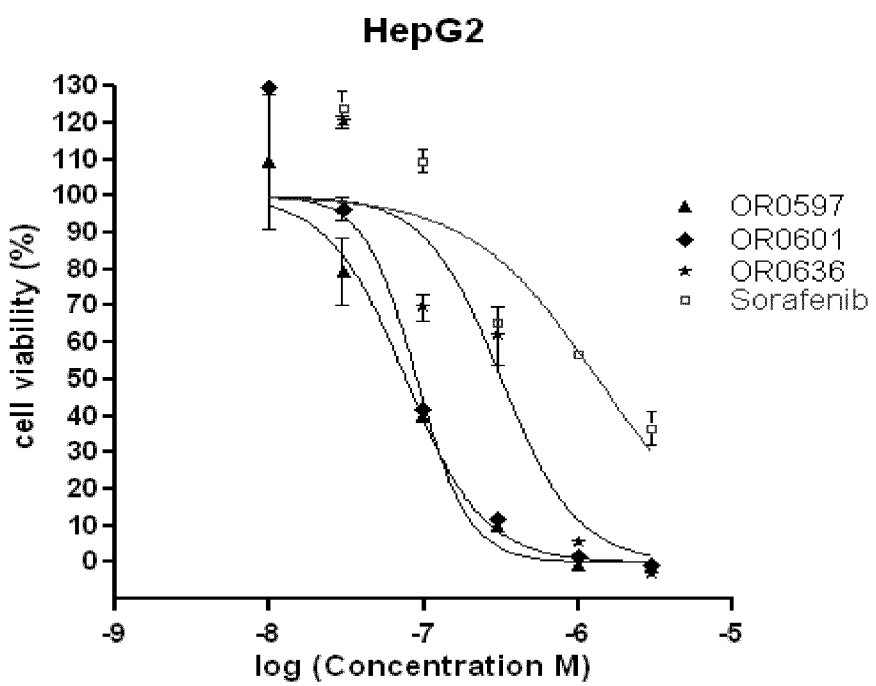
FIG. 2 is a graph representing anti-proliferative activity of some compounds on HepG2 cells.
Figure 3:
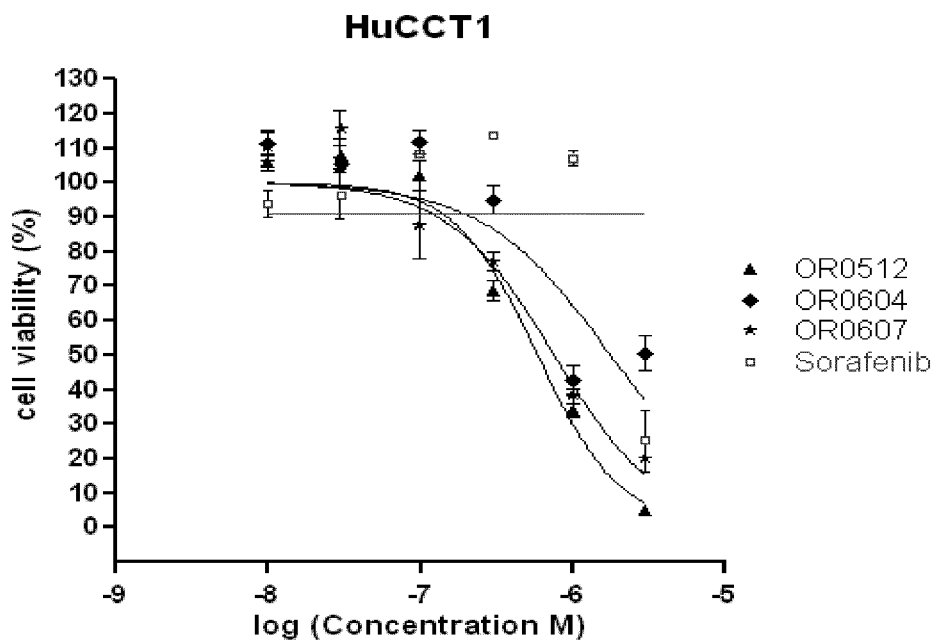
FIG. 3 is a graph representing anti-proliferative activity of some compounds on HuCCT1 cells.
Figure 4:
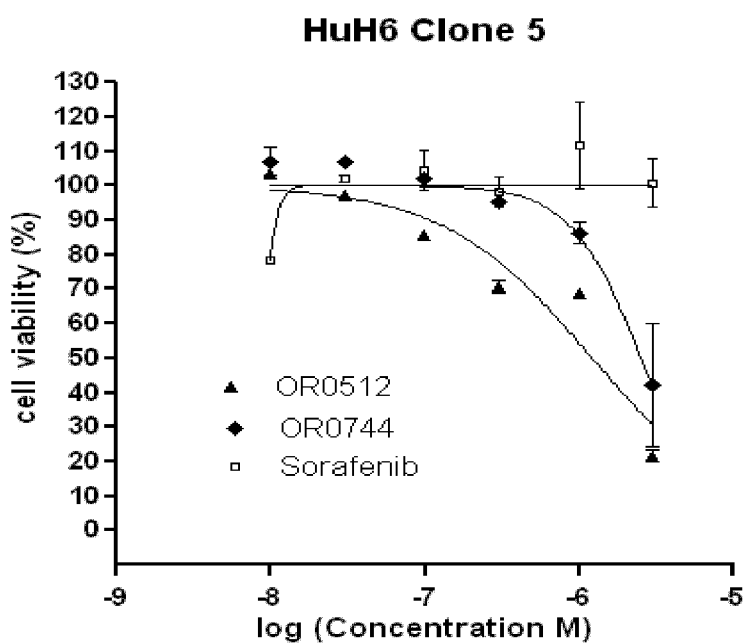
FIG. 4 is a graph representing anti-proliferative activity of some compounds on HuH6 Clone 5 cells.
Figure 5:
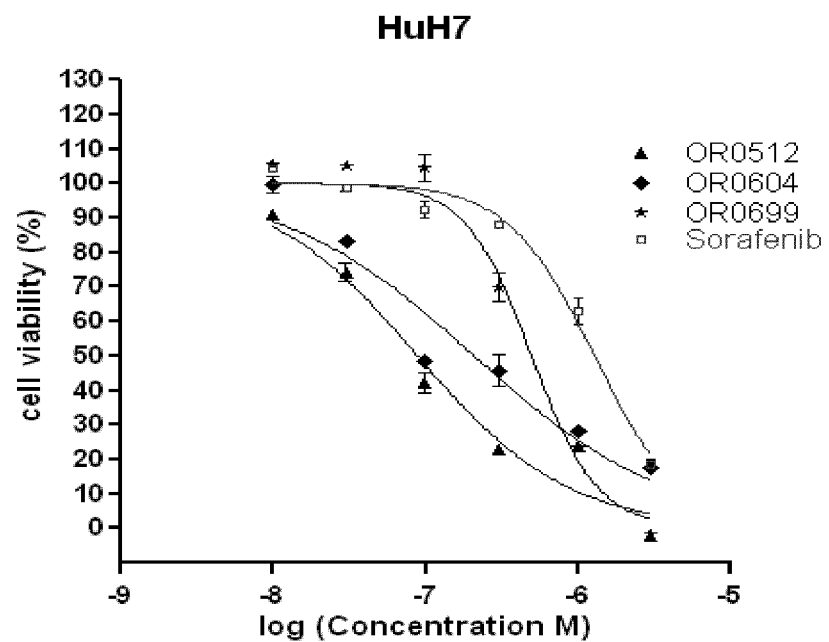
FIG. 5 is a graph representing anti-proliferative activity of some compounds on HuH7 cells.
Figure 6:
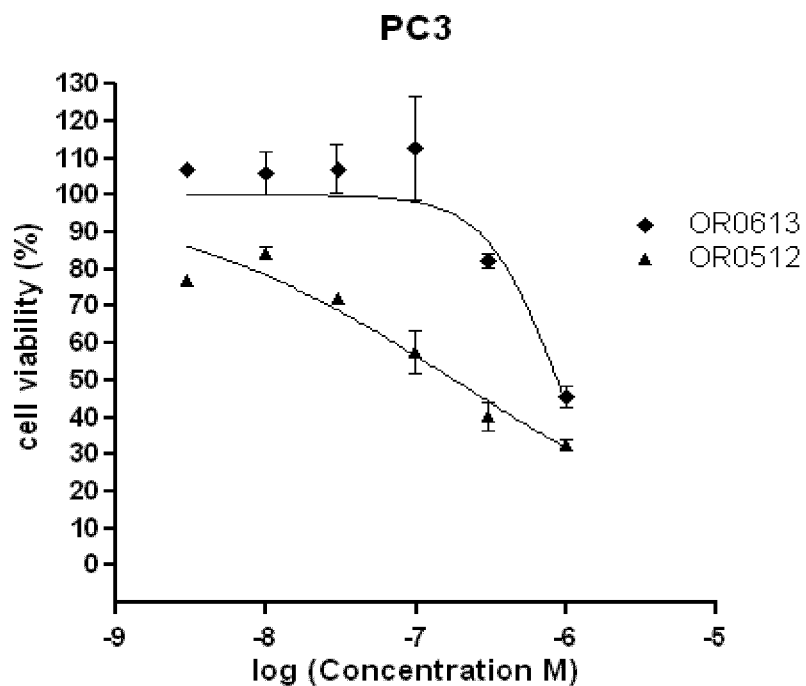
FIG. 6 is a graph representing anti-proliferative activity of some compounds on PC-3 cells.
Figure 7:
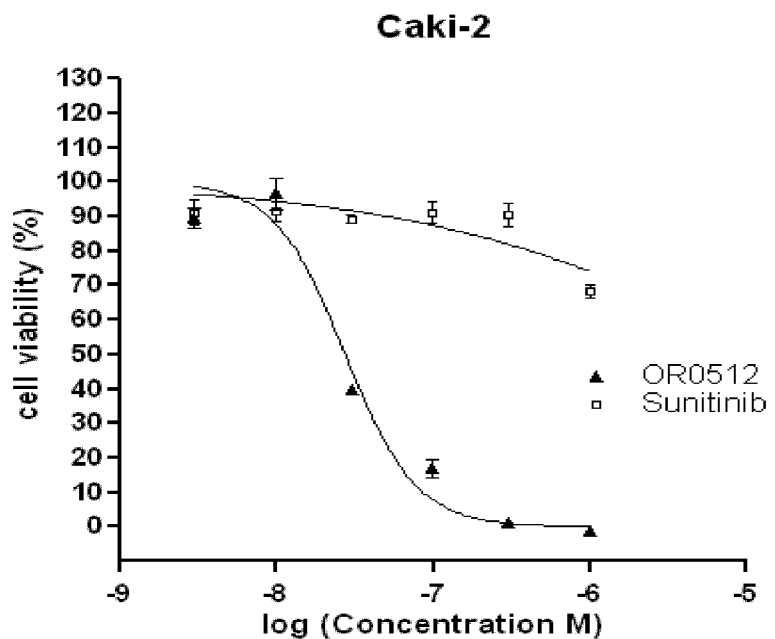
FIG. 7 is a graph representing anti-proliferative activity of some compounds on Caki-2 cells.
Figure 8:
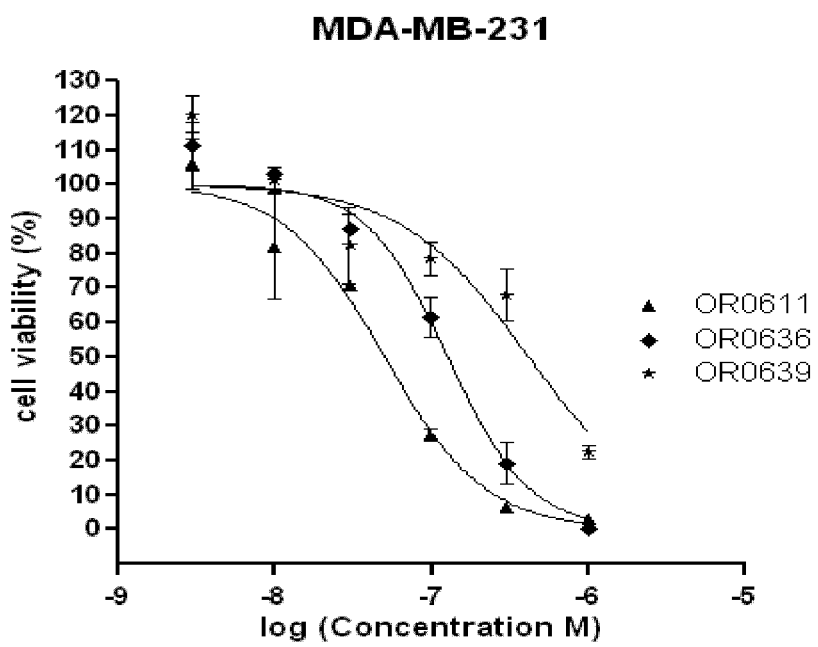
FIG. 8 is a graph representing anti-proliferative activity of some compounds on MDA-MB-231 cells.
Figure 9:
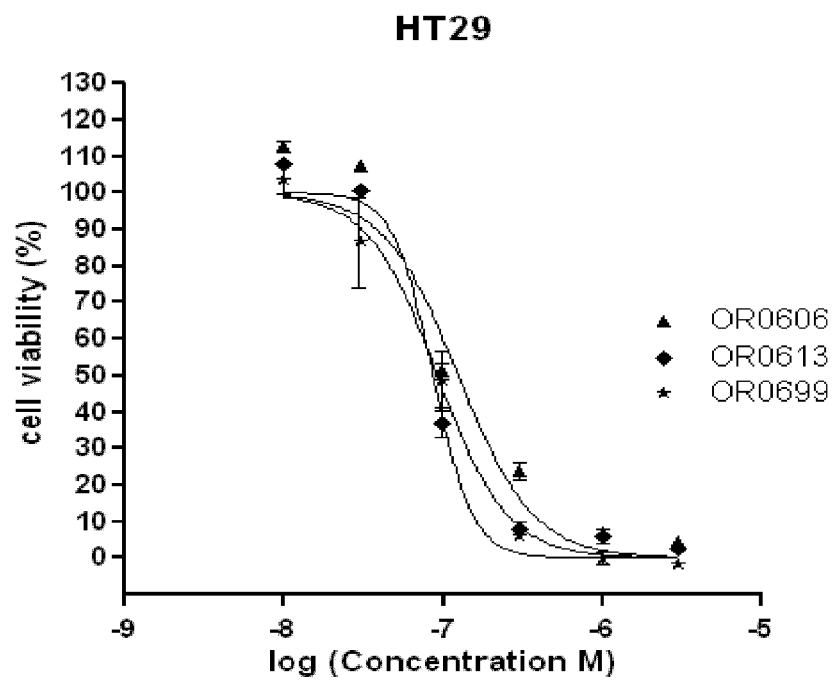
FIG. 9 is a graph representing anti-proliferative activity of some compounds on HT29 cells.
Figure 10:
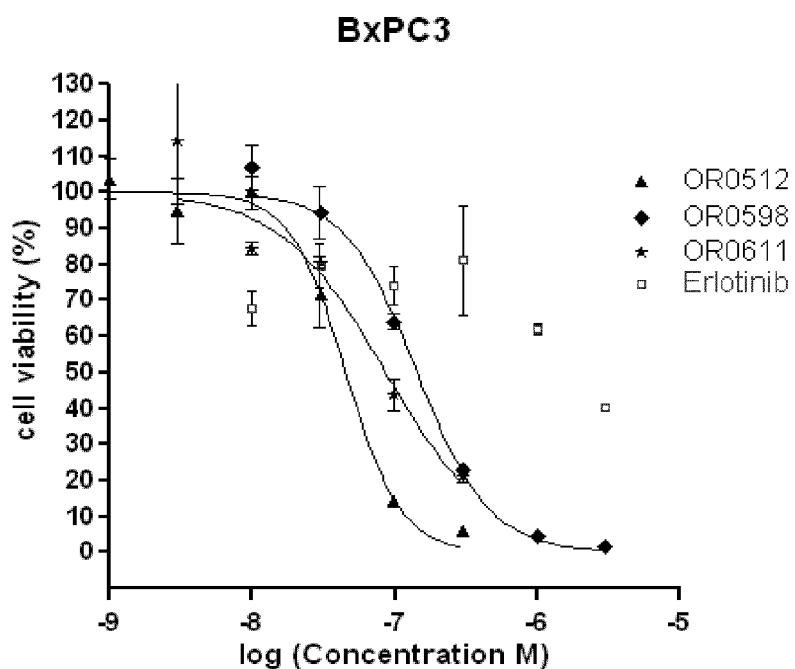
FIG. 10 is a graph representing anti-proliferative activity of some compounds on BxPC-3 cells.
Figure 11:
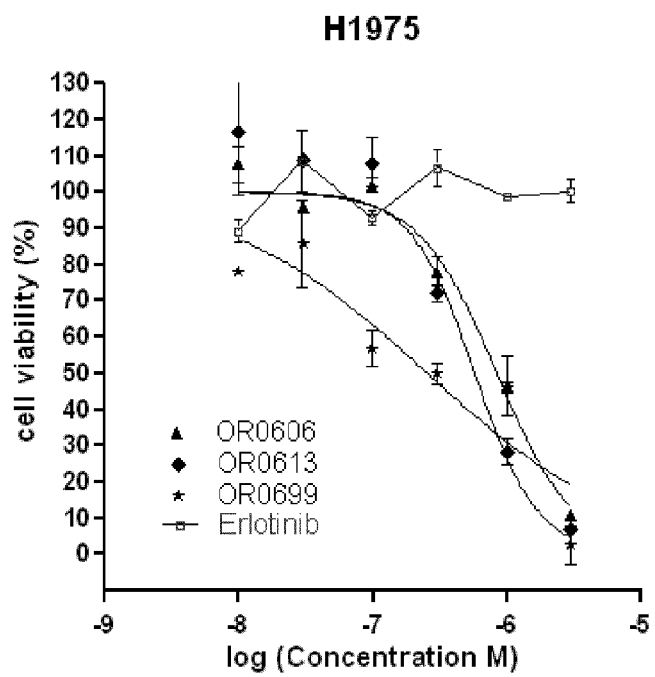
FIG. 11 is a graph representing anti-proliferative activity of some compounds on H1975 cells.
Figure 12:
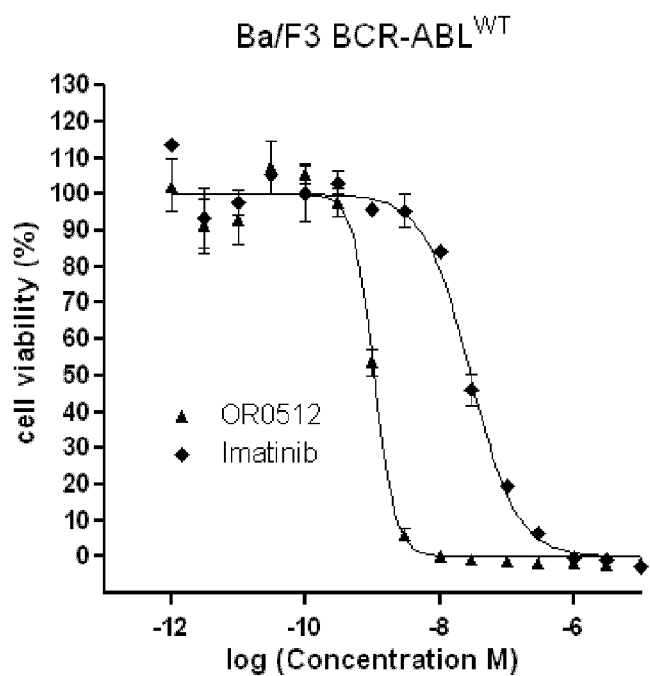
FIG. 12 is a graph representing anti-proliferative activity of some compounds on BaF3 BCR-ABL WT cells.
Figure 13:
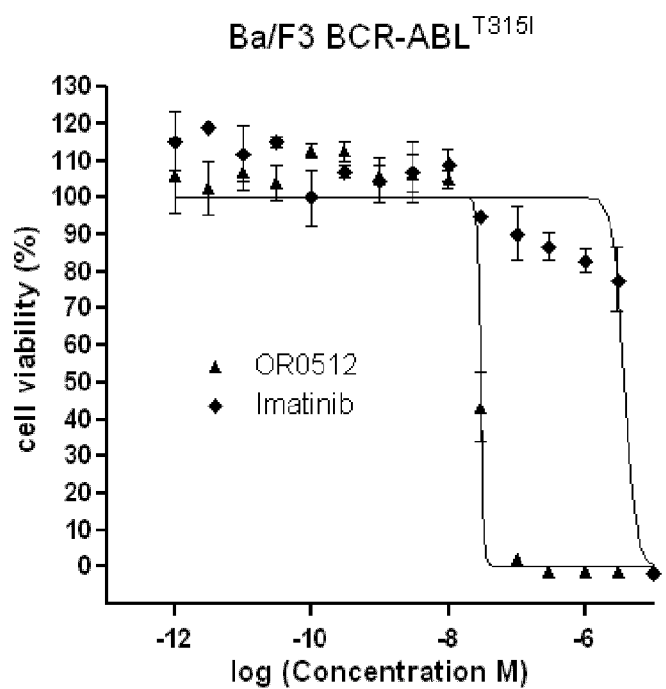
FIG. 13 is a graph representing anti-proliferative activity of some compounds on BaF3 BCR-ABL T315I cells.
Figure 14:
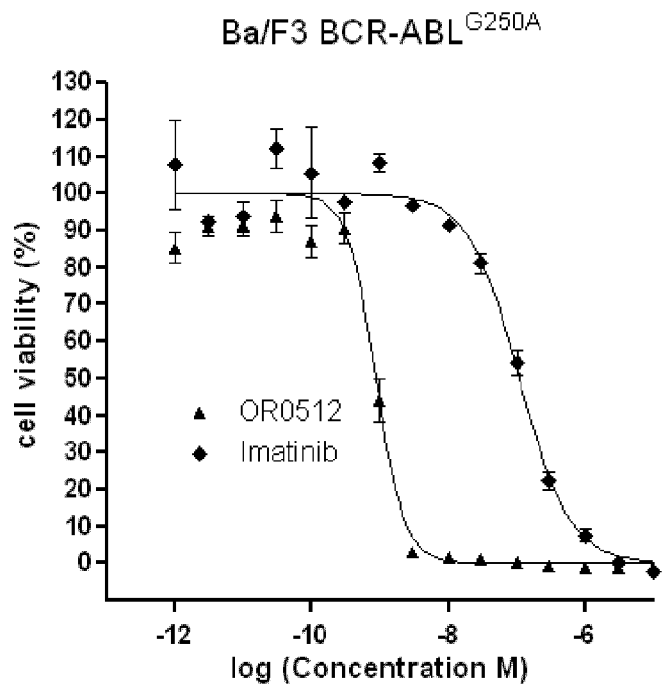
FIG. 14 is a graph representing anti-proliferative activity of some compounds on BaF3 BCR-ABL G250A cells.
Figure 15:
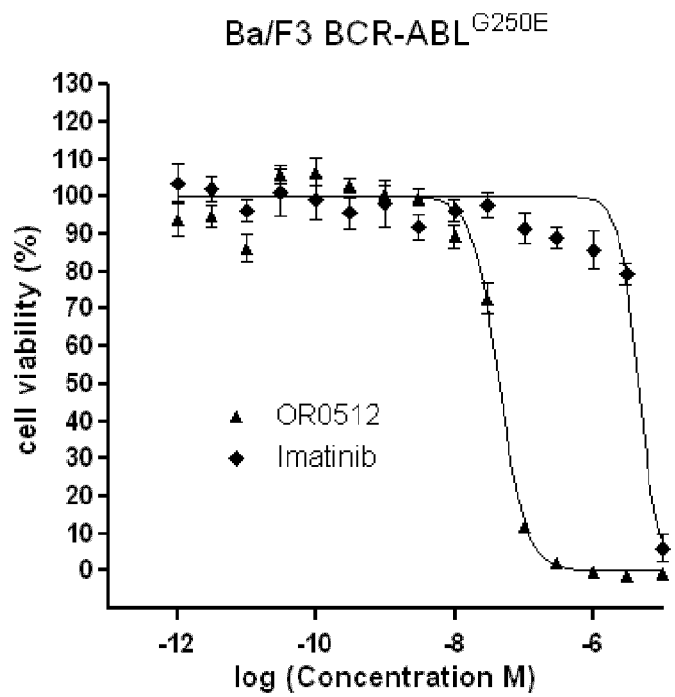
FIG. 15 is a graph representing anti-proliferative activity of some compounds on BaF3 BCR-ABL G250E cells.
Figure 16:
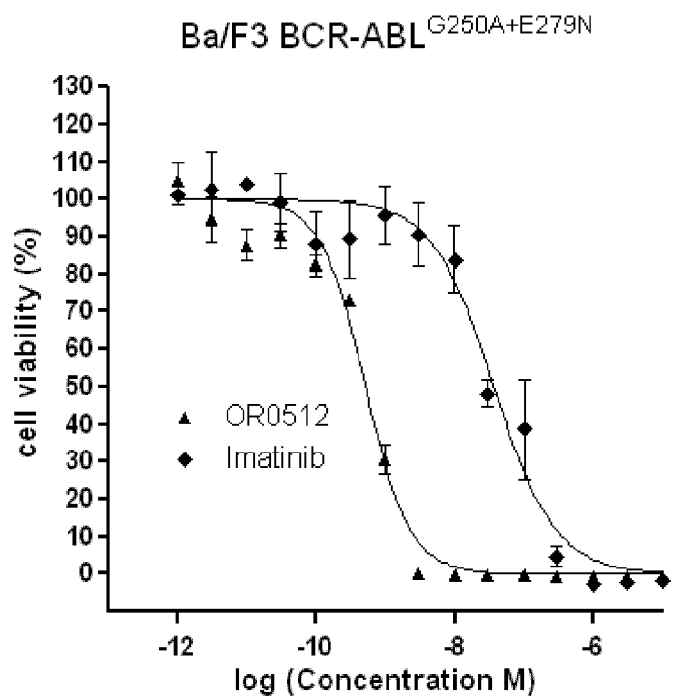
FIG. 16 is a graph representing anti-proliferative activity of some compounds on BaF3 BCR-ABL G250A+E279N cells.
Figure 17:
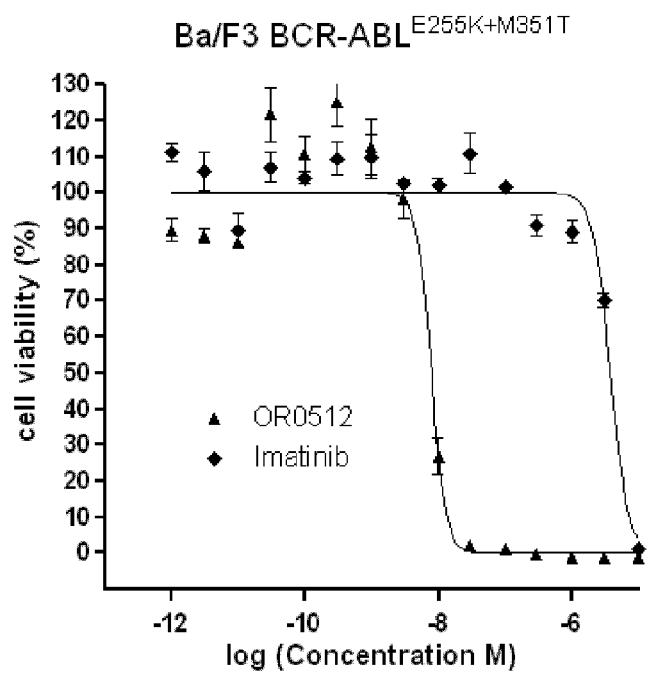
FIG. 17 is a graph representing anti-proliferative activity of some compounds on BaF3 BCR-ABL E255K+M351T cells.
Figure 18:
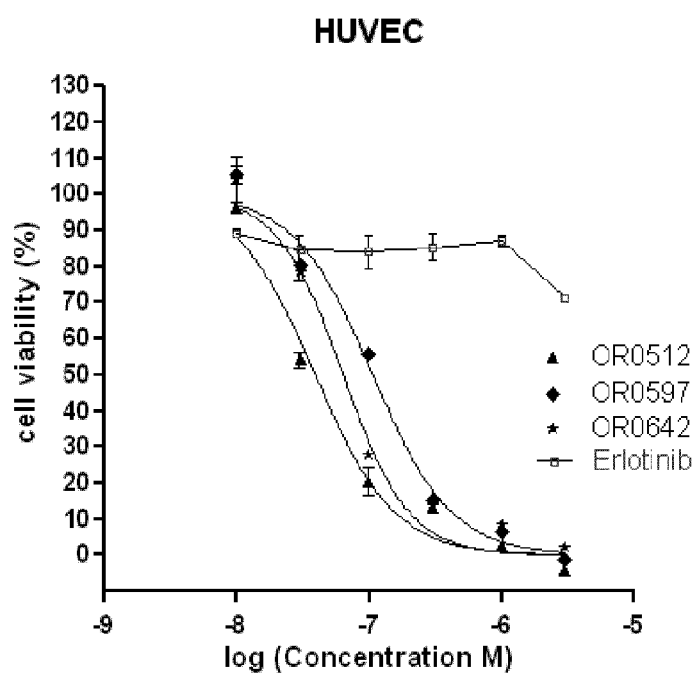
FIG. 18 is a graph representing anti-proliferative activity of some compounds on HUVEC cells.
Figure 19:
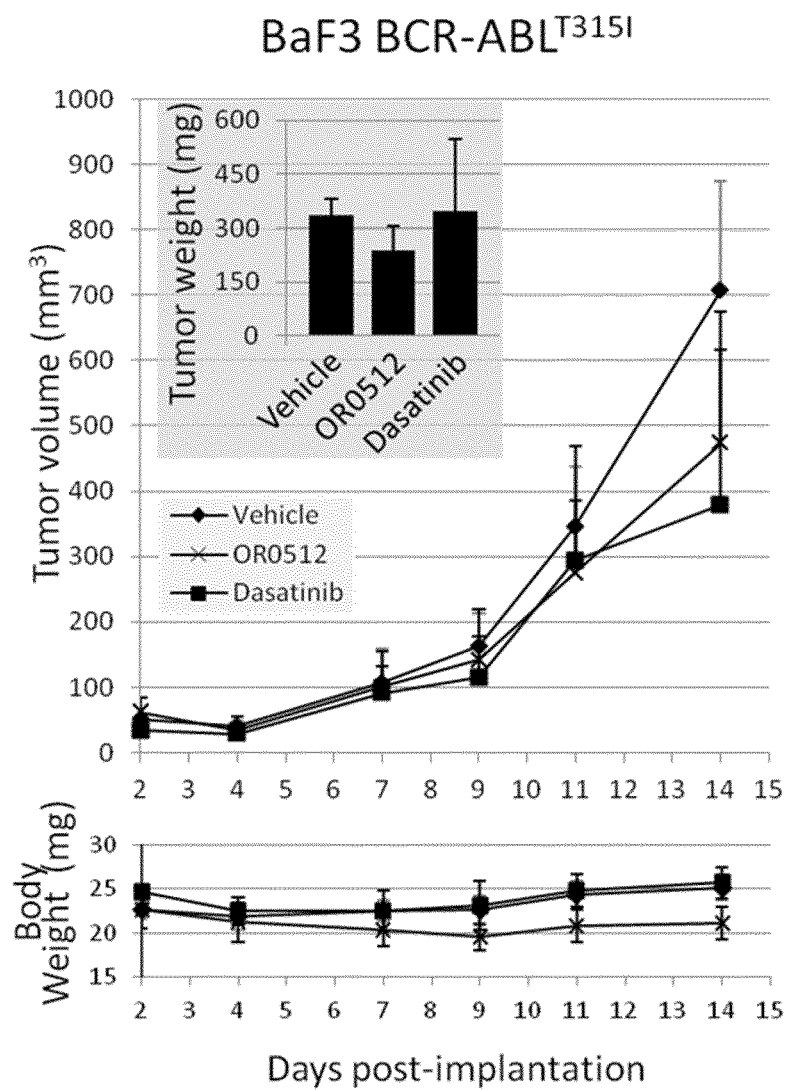
FIG. 19 is a graph representing the decrease of tumor (BaF3 BCR-ABL$^{T315I}$) volume (mm3), the mice body weight over time (Days post-implantation), and the tumor weight (mg) at the end of the experiment.
Figure 20:
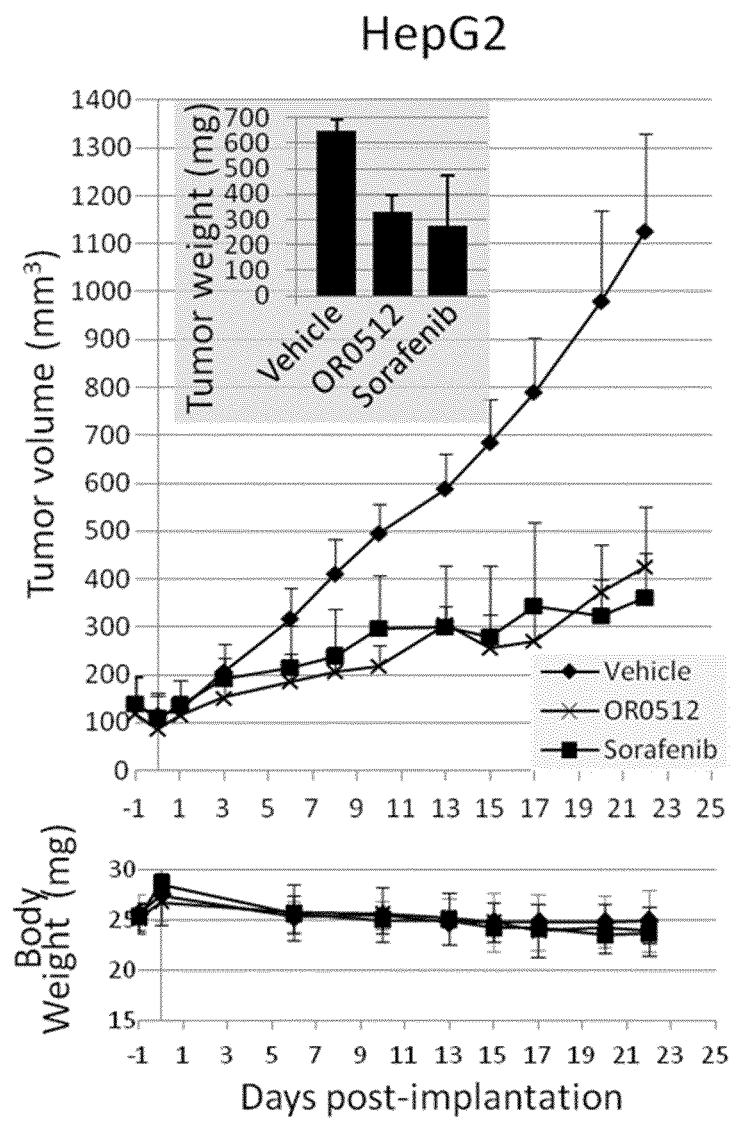
FIG. 20 is a graph representing the decrease of tumor (HepG2) volume (mm3), the mice body weight over time (Days post-implantation) and the tumor weight (mg) at the end of the experiment.
Figure 21:
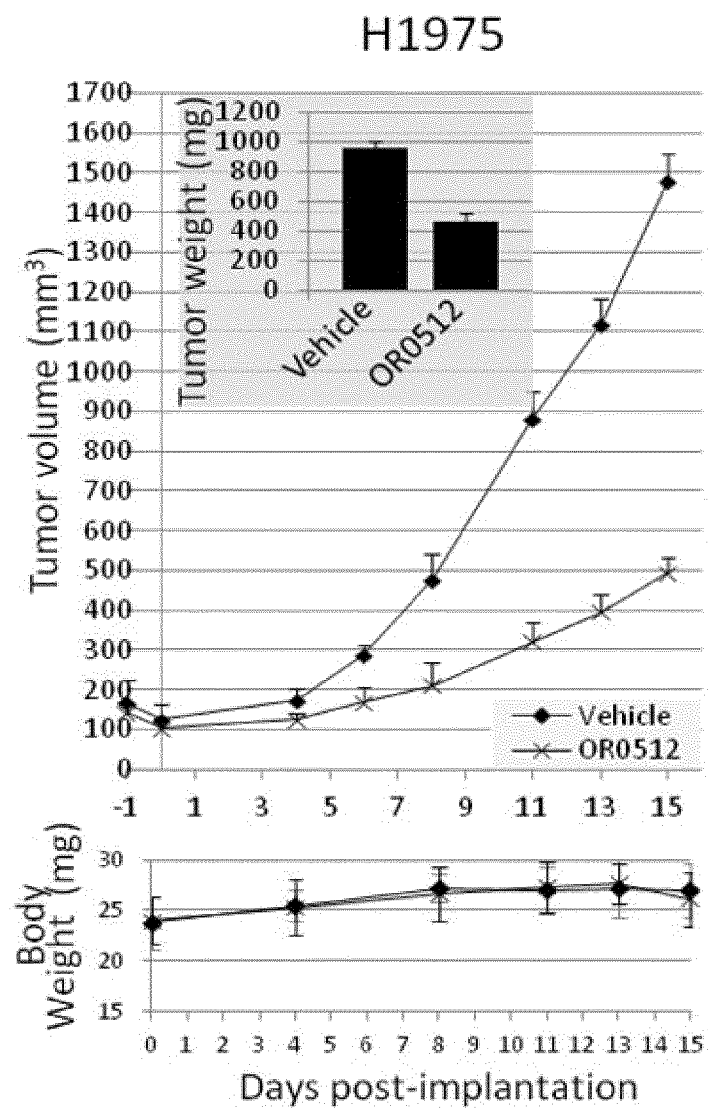
FIG. 21 is a graph representing the decrease of tumor (H1975) volume (mm3), the mice body weight over time (Days post-implantation) and the tumor weight (mg) at the end of the experiment.
Figure 22:
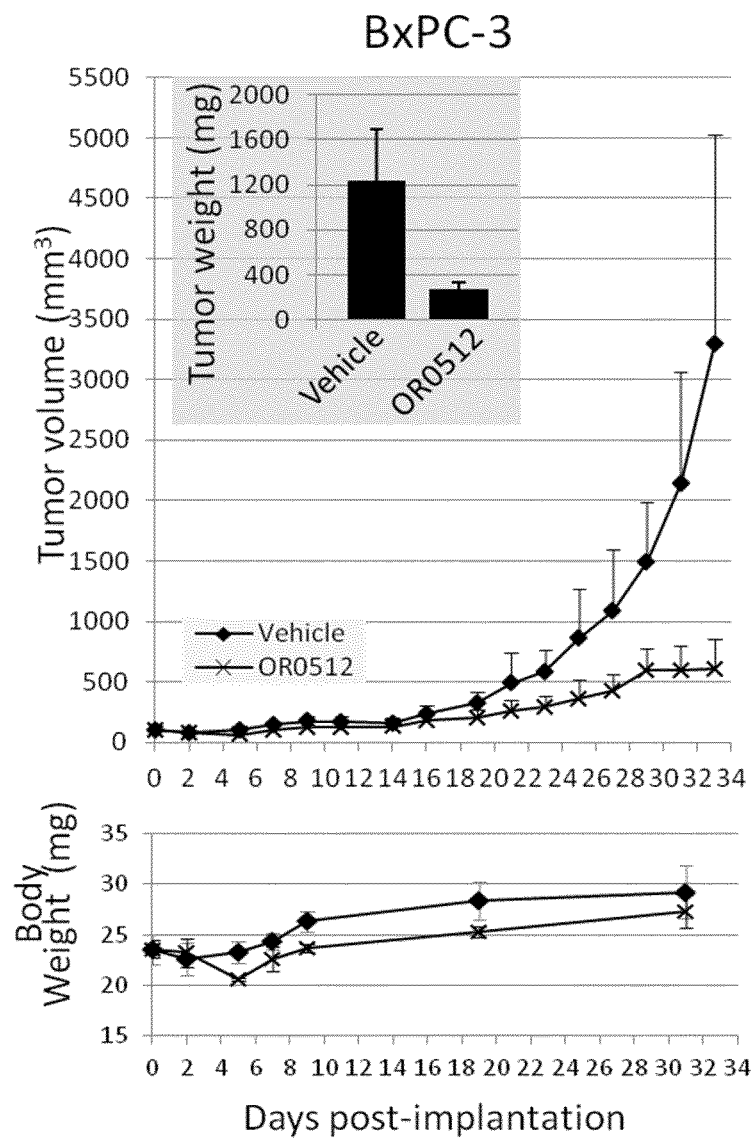
FIG. 22 is a graph representing the decrease of tumor (BxPC-3) volume (mm3), the mice body weight over time (Days post-implantation) and the tumor weight (mg) at the end of the experiment.
Figure 23:
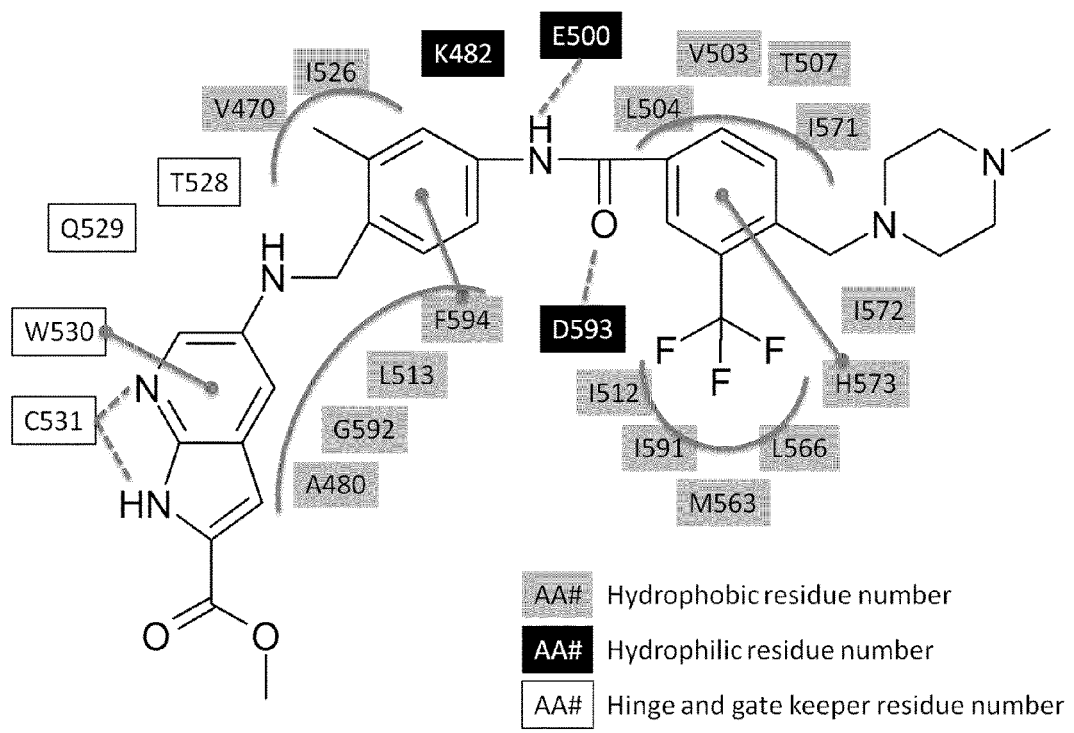
FIG. 23 is a schematic representation of the interactions (hydrophobic contacts, hydrogen bounds and aromatic staking) between compound OR0512 and the active site amino acids of the kinase domain of B-Raf according to the its crystal structure (PDB id=1UWH).
Figure 24:
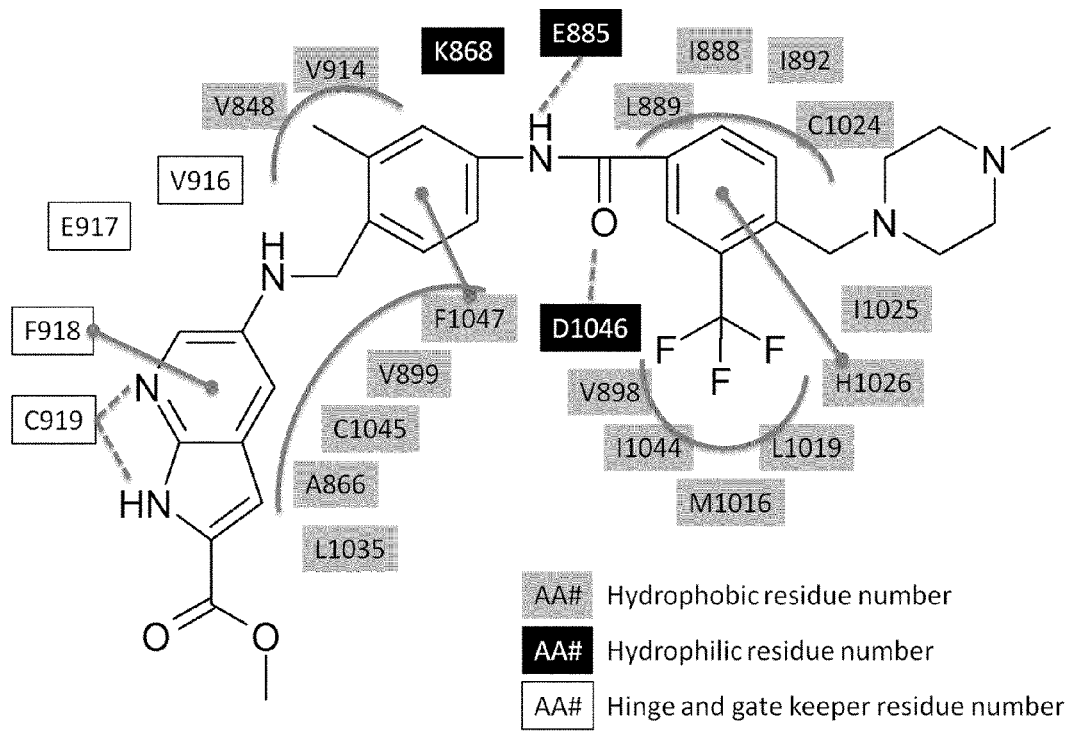
FIG. 24 is a schematic representation of the interactions (hydrophobic contacts, hydrogen bounds and aromatic staking) between compound OR0512 and the active site amino acids of the kinase domain of VEGFR2 according to the its crystal structure (PDB id=4ASD).
Figure 25:
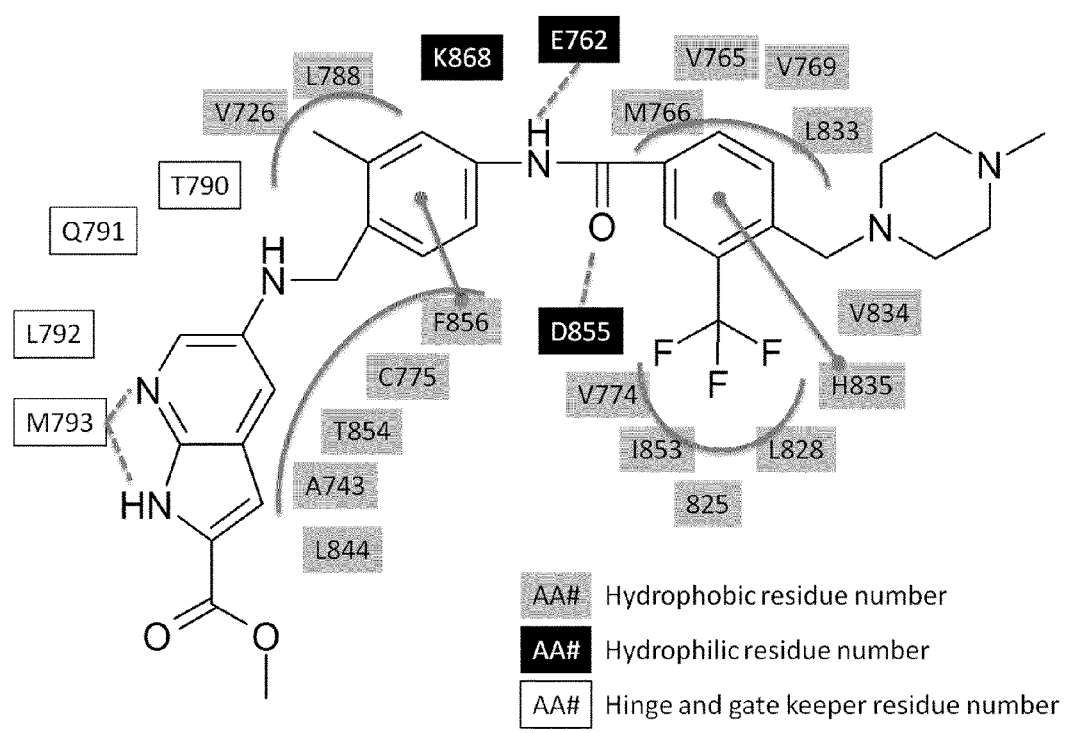
FIG. 25 is a schematic representation of the interactions (hydrophobic contacts, hydrogen bounds and aromatic staking) between compound OR0512 and the active site amino acids of the kinase domain of EGFR according to an homology model of this kinase.
Figure 26:
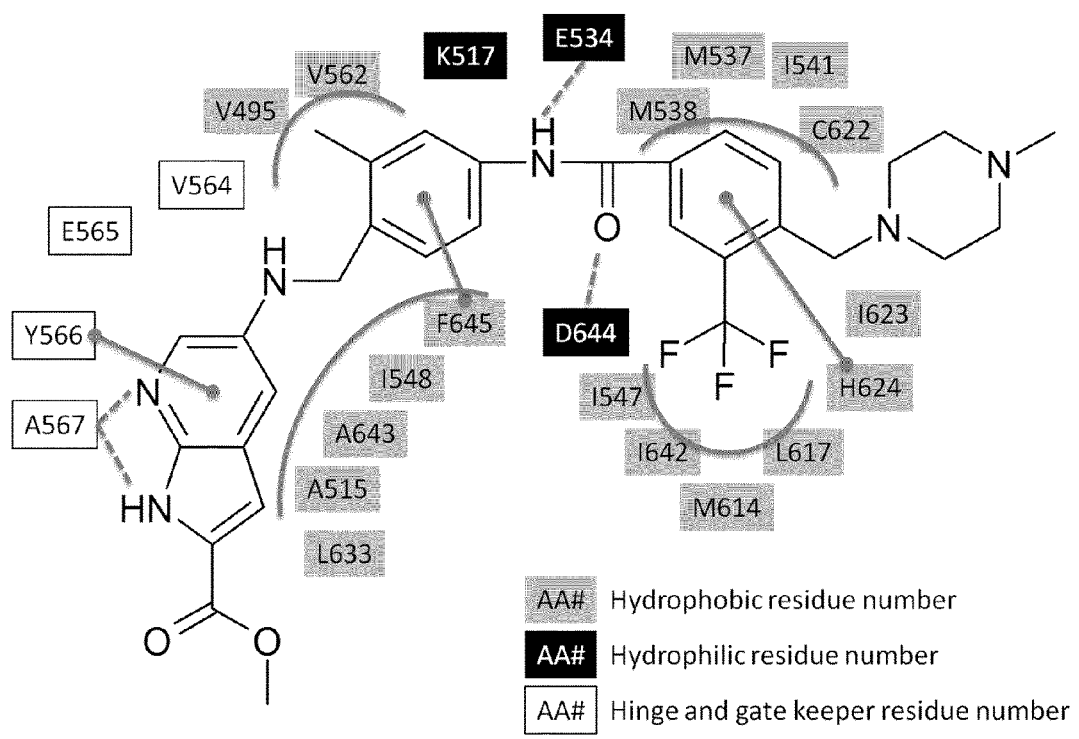
FIG. 26 is a schematic representation of the interactions (hydrophobic contacts, hydrogen bounds and aromatic staking) between compound OR0512 and the active site amino acids of the kinase domain of FGFR2 according to an homology model of this kinase.

The invention will be better understood on reading the following examples.

The compounds of the invention were obtained from 5-amino-1H-pyrrolo[2,3-b]pyridine-2-carboxylic acid methyl ester (commercially available from the company OriBase Pharma) in multi-stage synthesis, if necessary employing parallel synthesis apparatus ("Synthesis 1", Heidolph). The various synthesis protocols are detailed below together with the physicochemical characteristics of the compounds of the 7-azaindole type obtained.

The syntheses and analyses were carried out in the following conditions:

$^1$H and $^{13}$C Nuclear Magnetic Resonance:

Equipment:

Bruker Avance 400 (400 MHz); Bruker Avance 300 (300 MHz); Bruker DPX 200 (200 MHz)

Conditions of Use:

Room temperature (RT), chemical shifts expressed in parts per million (ppm), coupling constants (J) expressed in Hertz, internal reference trimethylsilane (TMS), multiplicity of the signals indicated by lower-case letters (singlet s, broad singlet bs, doublet d, triplet t, quadruplet q, multiple m), dimethylsulphoxide $d_6$, methanol $d_4$, chloroform d, as deuterated solvents.

High-Performance Liquid Chromatography (HPLC):

Equipment:

Agilent Technology 1260 Infinity

Conditions of Use:

Zorbax SB-C18, 2.1×50 mm, 1.8 µm; temperature: 30° C., Water/Acetonitrile/Formic acid elution gradient (90%/10%/0.1% to 0%/100%/0.1%)

Mass Spectrometry (MS):

Equipment:

Quadripole Agilent Technologies 6120

Conditions of Use:

ElectroSpray (ESI) in positive and/or negative mode.

Weighings:

Equipment:

Denver Instrument TP214 (precision 0.1 mg)

Conditions of Use:

Weighings carried out to the nearest milligram.

Parallel Synthesis:

Equipment:

Heidolph Synthesis 1 (16 reactors)

Conditions of Use:

16 reactions in parallel, room temperature, multiple evaporations.

Reactions Under Pressure:

Equipment:

Parr 300 mL autoclave.

Conditions of Use:

Hydrogenation under 20 or 30 bar of hydrogen.

Syntheses

Example A

Synthesis of 5-{2-methyl-5-[3-ureido]-benzylamino}-1H-pyrrolo[2,3-b]pyridine-2-carboxylic acid methyl ester in 3 steps starting from the commercial reagent from the company OriBase Pharma Scheme 14 represents a general method of synthesis of 5-{2-methyl-5-[3-ureido]-benzylamino}-1H-pyrrolo[2,3-b]pyridine-2-carboxylic acid methyl ester.

Scheme 14 - General synthesis scheme of example A

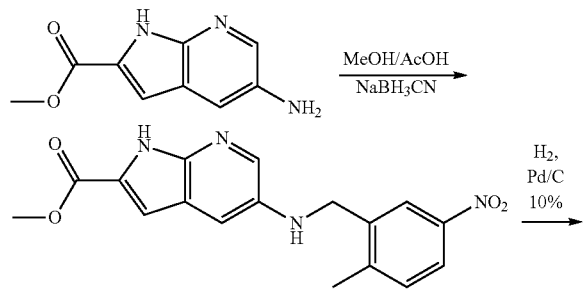

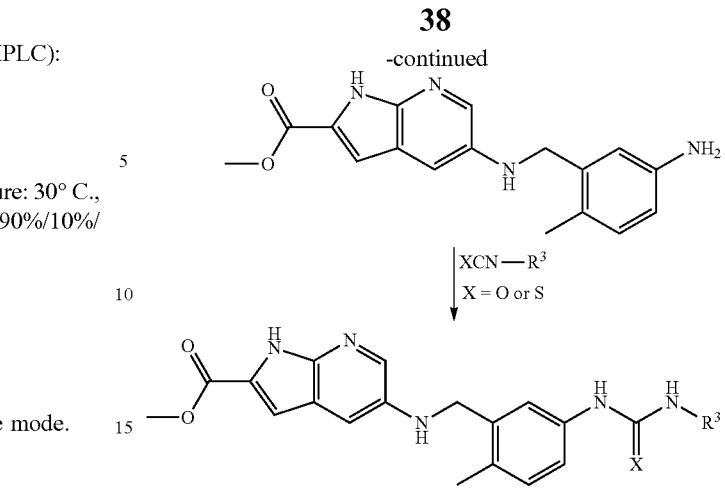

Step 1: General protocol for the preparation of 5-(2-methyl-5-nitro-benzylamino)-1H-pyrrolo[2,3-b]pyridine-2-carboxylic acid methyl ester 5-Amino-1H-pyrrolo[2,3-b]pyridine-2-carboxylic acid methyl ester (12.16 g, 63.7 mol) and 2-methyl-5-nitrobenzaldehyde (10.5 g, 63.7 mol) are stirred in AcOH 10% in MeOH for 2 h. Then NaBH$_3$CN (7.9 g, 127.3 mol) is slowly added and mixture is stirred under argon for 48 h. Solvents are evaporated and a saturated solution of NaHCO$_3$ is added until neutrality. Solid formed is filtrated and washed with petroleum ether/EtOAc 5/5. A brownish solid, methyl 5-(5-amino-2-methylbenzylnitro)-1H-pyrrolo[2,3-b]pyridine-2-carboxylate, is obtained (17.9 g, 53.9 mmol). Yield=82%. ESI-MS: m/z 341 ([M+H]$^+$). HPLC purity: 80%

Step 2: General protocol for the preparation of 5-(5-amino-2-methyl-benzylamino)-1H-pyrrolo[2,3-b]pyridine-2-carboxylic acid methyl ester 5-(2-Methyl-5-nitro-benzylamino)-1H-pyrrolo[2,3-b]pyridine-2-carboxylic acid methyl ester (17.8 g, 53.9 mmol), methanol (300 mL), 7.2 mL of HCl 12N and palladium 10% on charcoal (1.7 g, 10% w/w) are put in an autoclave filled with 30 bar of dihydrogen and stirred for 48 h. Mixture is filtered on celite and washed with methanol. Solvent is evaporated, then NaHCO$_{3(aq)}$ is added. The solid obtained is filtrated, washed with water to obtain a brownish solid (14.4 g, 46.4 mmol). Yield=96%. $^1$H NMR (300 MHz, DMSO-d6) δ 12.03 (s, 1H), 8.08 (d, J=2.6 Hz, 1H), 6.95 (d, J=2.7 Hz, 1H), 6.90 (s, 1H), 6.83 (d, J=8.0 Hz, 1H), 6.57 (d, J=2.3 Hz, 1H), 6.36 (dd, J=2.3 Hz, 1H), 5.94 (s, 1H), 4.77 (s, 2H), 4.07 (d, J=5.3 Hz, 2H), 3.83 (s, 4H). ESI-MS: m/z 311 ([M+H]$^+$). HPLC purity: 95%.

Step 3: General protocol for the preparation of 5-{2-methyl-5-[3-ureido]-benzylamino}-1H-pyrrolo[2,3-b]pyridine-2-carboxylic acid methyl ester To a solution of 5-(5-amino-2-methyl-benzylamino)-1H-pyrrolo[2,3-b]pyridine-2-carboxylic acid methyl ester was added the isocyanate or isothiocyanate derivative (1 eq). The mixture was allowed to stir at RT overnight. The solvent was removed and the crude product was purified by silica gel chromatography.

Table 1 shows the various compounds synthesized according to the synthesis described above in Scheme 14.

TABLE 1

Compounds obtained by example A

| Example No. | Used reagents | Synthesized inhibitors (mass and analytical data) |
|---|---|---|
| OR0603 | 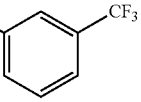 | 5-{2-Methyl-5-[3-(3-trifluoromethyl-phenyl)-ureido]-benzylamino}-1H-pyrrolo[2,3-b]pyridine-2-carboxylic acid methyl ester<br>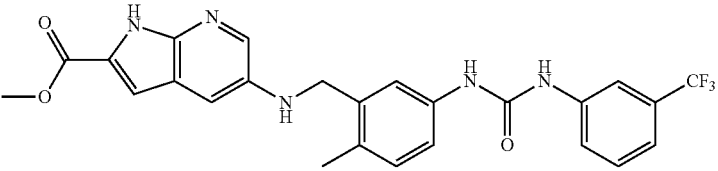<br>Yield: 22%<br>$^1$H NMR (400 MHz, DMSO-d6) δ (ppm) 9.03 (br s, 1H), 8.80 (s, 1H), 8.09 (d, J = 2.6, 1H), 7.98 (s, 1H), 7.48 (d, 2H), 7.40 (s, 1H), 7.26 (s, 2H), 7.11 (d, J = 8.2, 1H), 6.97 (d, J = 2.6, 1H), 6.90 (s, 1H), 6.08 (t, J = 5.4, 1H), 4.20 (d, J = 5.4, 2H), 3.82 (s, 3H), 2.28 (s, 3H).<br>HPLC: 90%; MS: 498.2 (M + 1) |
| OR0896 |  | 5-[2-Methyl-5-(3-pyridin-3-yl-ureido)-benzylamino]-1H-pyrrolo[2,3-b]pyridine-2-carboxylic acid methyl ester<br>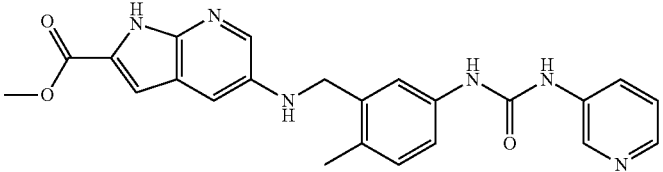<br>Yield: 14%<br>$^1$H NMR (300 MHz, DMSO-d6) δ (ppm) 12.04 (s, 1H), 8.69 (s, 2H), 8.57-8.50 (m, 1H), 8.15 (d, J = 3.4 Hz, 1H), 8.10 (d, J = 2.5 Hz, 1H), 7.94-7.84 (m, 1H), 7.47-7.37 (m, 1H), 7.34-7.20 (m, 2H), 7.11 (d, J = 8.2 Hz, 1H), 6.97 (d, J = 2.3 Hz, 1H), 6.89 (s, 1H), 6.15-6.03 (m, 1H), 4.21 (d, J = 4.6 Hz, 2H), 3.82 (s, 3H), 2.28 (s, 3H).<br>HPLC: 99%; MS: 431 (M + 1) |
| OR0952 |  | 5-[2-Methyl-5-(3-pyridin-4-yl-ureido)-benzylamino]-1H-pyrrolo[2,3-b]pyridine-2-carboxylic acid methyl ester<br>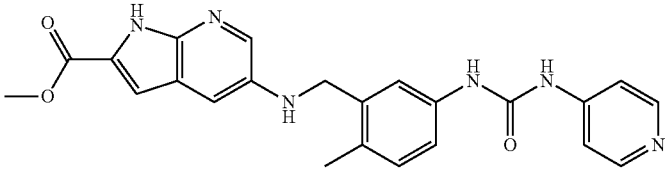<br>Yield: 12%<br>$^1$H NMR (300 MHz, DMSO-d6) δ (ppm) 12.04 (s, 1H), 8.93 (s, 1H), 8.72 (s, 1H), 8.17-8.02 (m, 1H), 7.66-7.3 (m, 3H), 7.28-7.20 (m, 1H), 7.12 (d, J = 8.0, 1H), 6.96 (d, J = 2.0, 1H), 6.89 (d, J = 1.5, 1H), 6.18-6.02 (m, 1H), 4.21 (d, J = 5.0, 2H), 3.82 (s, 3H), 2.29 (s, 3H).<br>HPLC: 97%; MS: 431 (M + 1) |

TABLE 1-continued

Compounds obtained by example A

| Example No. Used reagents | Synthesized inhibitors (mass and analytical data) |
|---|---|
| OR1016 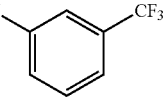 | 5-{2-Methyl-5-[3-(3-trifluoromethyl-phenyl)-thioureido]-benzylamino}-1H-pyrrolo[2,3-b]pyridine-2-carboxylic acid methyl ester 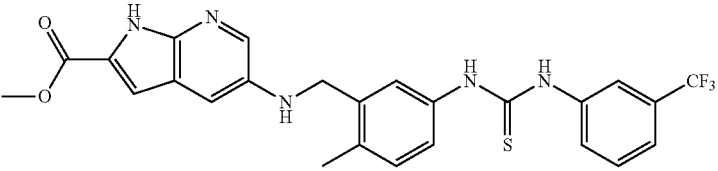 Yield: 36% ¹H NMR (300 MHz, DMSO-d6) δ (ppm) 12.01 (s, 1H), 9.91 (s, 1H), 9.76 (s, 1H), 8.08 (d, J = 2.5, 1H), 7.93 (s, 1H), 7.65 (d, J = 8.3, 1H), 7.49 (t, J = 7.9, 1H), 7.41 (d, J = 8.0, 1H), 7.34 (m, 2H), 7.18 (d, J = 8.0, 1H), 6.98 (s, 1H), 6.85 (d, J = 1.9, 1H), 6.09 (s, 1H), 4.23 (d, J = 5.3, 2H), 3.82 (s, 3H), 2.33 (s, 3H). HPLC: 94%; MS: 514 (M + 1) |

Example B

Synthesis of 5-[2-methyl-5-(sulfonylamino)-benzylamino]-1H-pyrrolo[2,3-b]pyridine-2-carboxylic acid methyl ester in 1 stage Scheme 15 represents a general method of synthesis of 5-[2-methyl-5-(sulfonylamino)-benzylamino]-1H-pyrrolo[2,3-b]pyridine-2-carboxylic acid methyl ester starting from an amino derivative already described in example A.

Scheme 15 - General synthesis scheme of example B

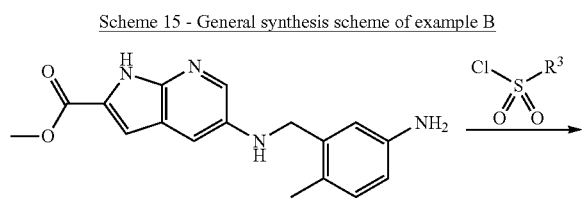

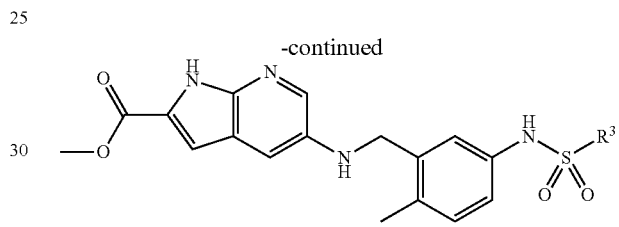

-continued

Step 1: Synthesis of 5-[2-methyl-5-(sulfonylamino)-benzylamino]-1H-pyrrolo[2,3-b]pyridine-2-carboxylic acid methyl ester 20 μL of trimethylamine (1.1 eq) is added to a cold solution of 5-(5-amino-2-methyl-benzylamino)-1H-pyrrolo[2,3-b]pyridine-2-carboxylic acid methyl ester (40 mg, 0.13 mmol) in 2 mL of anhydrous DMF. A cold solution of sulfonyl chloride derivative (1.2 eq) in 2 mL of anhydrous DMF is then added dropwise. The reaction mixture is stirred at 0° C. for 30 minutes and overnight at RT. DMF is evaporated, then saturated NaHCO₃ solution is added. The solid obtained is filtrated, washed with water to obtain a yellow solid. Table 2 shows the compound synthesized according to the synthesis Scheme 15 described above.

TABLE 2

Compounds obtained by example B

| Example No. Used reagents | Synthesized inhibitors (mass and analytical data) |
|---|---|
| OR0595 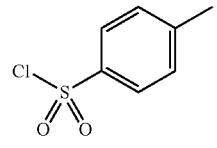 | 5-[2-Methyl-5-(toluene-4-sulfonylamino)-benzylamino]-1H-pyrrolo[2,3-b]pyridine-2-carboxylic acid methyl ester 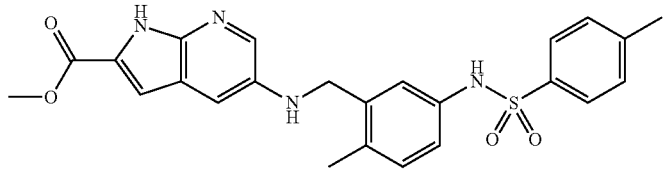 |

TABLE 2-continued

Compounds obtained by example B

| Example No. Used reagents | Synthesized inhibitors (mass and analytical data) |
|---|---|

Yield: 83%
$^1$H NMR (600 MHz, DMSO-d6) δ (ppm) 12.09 (s, 1H), 10.00 (s, 1H), 8.08 (d, J = 2.6, 1H), 7.40 (d, J = 8.2, 2H), 7.17 (s, 1H), 7.07-6.97 (m, 3H), 6.87 (d, J = 2.0, 1H), 6.84-6.79 (m, 2H), 6.12 (t, J = 5.5, 1H), 4.14 (d, J = 5.5, 2H), 3.85 (s, 3H), 2.22 (s, 3H), 2.21 (s, 3H).
HPLC: 99%; MS: 465.2 (M + 1)

OR0882

5-[2-Methyl-5-(3-trifluoromethyl-benzenesulfonylamino)-benzylamino]-1H-pyrrolo[2,3-b]pyridine-2-carboxylic acid methyl ester Yield: x21%
$^1$H NMR (300 MHz, DMSO-d6) δ (ppm) 12.04 (s, 1H), 10.21 (s, 1H), 8.02 (s, 1H), 7.93 (s, 1H), 7.83 (d, J = 7.3, 1H), 7.74 (d, J = 7.3, 1H), 7.52 (t, J = 7.3, 1H), 7.14-6.99 (m, 2H), 6.89-6.77 (m, 3H), 6.06 (t, J = 5.8, 1H), 4.13 (d, J = 5.8, 2H), 3.83 (s, 3H), 2.23 (s, 3H).
HPLC: 99%; MS: 465 (M + 1)

Example C

Synthesis of 5-{2-methyl-5-[3-amido]-benzylamino}-1H-pyrrolo[2,3-b]pyridine-2-carboxylic methyl esters in 1 stage Scheme 16 represents a general method of synthesis of 5-{2-methyl-5-[3-amido]-benzylamino}-1H-pyrrolo[2,3-b]pyridine-2-carboxylic methyl ester in 1 step. This step consists on the reaction of 5-(5-amino-2-methyl-benzylamino)-1H-pyrrolo[2,3-b]pyridine-2-carboxylic acid methyl ester with either an acyl chloride or a carboxylic acid.

Scheme 16 - General synthesis of example C

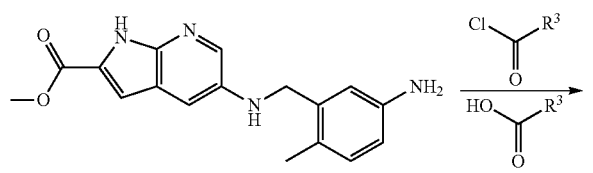

Option 1: Synthesis of 5-{2-methyl-5-[3-amido]-benzylamino}-1H-pyrrolo[2,3-b]pyridine-2-carboxylic methyl esters by reaction of acyl chlorides 55 μL of trimethylamine (3 eq) and 1.5 eq of acyl chloride are added to a solution of 5-(5-Amino-2-methyl-benzylamino)-1H-pyrrolo[2,3-b]pyridine-2-carboxylic acid methyl ester (40 mg, 0.13 mmol) in anhydrous DMF. The reaction mixture is stirred overnight at RT. DMF is evaporated; the solid is taken off into ethyl acetate. The organic layer is washed with saturated NaHCO$_3$ solution, dried over Na$_2$SO$_4$ and evaporated under reduce pressure to give a yellow solid.

Table 3 shows the compounds synthesized according to the synthesis schema 16 described above, with option1 (i.e. reaction of acyl chlorides).

TABLE 3

Compounds obtained by example C with acyl chlorides

| Example No. | Used reagents | Synthesized inhibitors (mass and analytical data) |
|---|---|---|
| OR0599 | 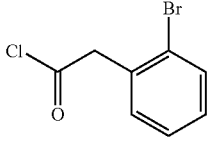 [SMILES: O=C(Cl)Cc1ccccc1Br] | 5-{5-[2-(2-Bromo-phenyl)-acetylamino]-2-methyl-benzylamino}-1H-pyrrolo[2,3-b]pyridine-2-carboxylic acid methyl ester<br>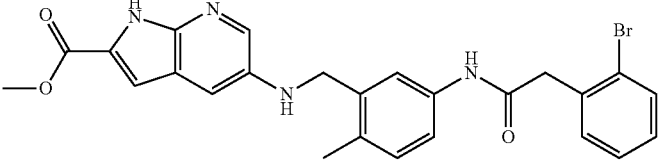<br>Yield: 20%<br>$^1$H NMR (400 MHz, DMSO-d6) δ (ppm) 12.02 (s, 1H), 10.06 (s, 1H), 8.13-8.00 (m, 1H), 7.65-7.49 (m, 1H), 7.42 (bs, 1H), 7.38-7.27 (m, 2H), 7.22-7.14 (m, 1H), 7.13-7.06 (m, 1H), 6.96-6.91 (m, 1H), 6.91-6.85 (m, 1H), 6.09-5.99 (m, 1H), 4.25-4.13 (m, 2H), 3.82 (s, 3H), 3.75 (s, 2H), 2.27 (s, 3H).<br>HPLC: 96%; MS: 507.1 (M + 1) |
| OR0618 | 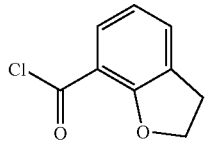 [SMILES: O=C(Cl)c1cccc2c1OCC2] | 5-{5-[(2,3-Dihydro-benzofuran-7-carbonyl)-amino]-2-methyl-benzylamino}-1H-pyrrolo[2,3-b]pyridine-2-carboxylic acid methyl ester<br>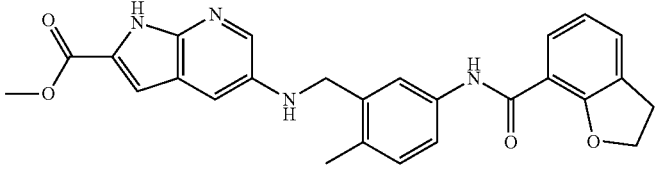<br>Yield: 13%<br>$^1$H NMR (400 MHz, DMSO-d6) δ (ppm) 9.63 (s, 1H), 8.10 (d, J = 2.5, 1H), 7.63 (d, J = 1.8, 1H), 7.60-7.54 (m, 2H), 7.42 (d, J = 6.3, 1H), 7.18 (d, J = 8.2, 1H), 7.03 (d, J = 2.5, 1H), 6.96 (t, J = 7.6, 1H), 6.90 (d, J = 1.8, 1H), 6.01 (t, J = 5.5, 1H), 4.72 (t, J = 8.8, 2H), 4.22 (d, J = 5.5, 2H), 3.83 (s, 3H), 3.25 (t, J = 8.8, 2H), 2.33 (s, 3H).<br>HPLC: 92%; MS: 457.0 (M + 1) |
| OR0620 | 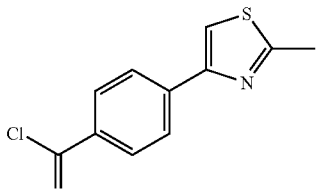 | 5-{2-Methyl-5-[4-(2-methyl-thiazol-4-yl)-benzoylamino]-benzylamino}-1H-pyrrolo[2,3-b]pyridine-2-carboxylic acid methyl ester<br>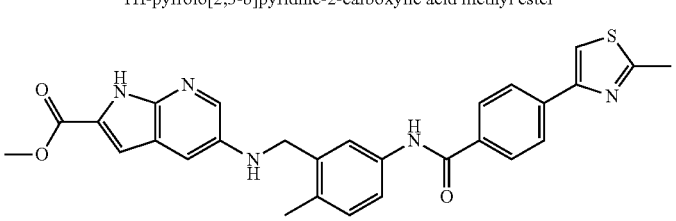<br>Yield: 36%<br>$^1$H NMR (400 MHz, DMSO-d6) δ (ppm) 12.01 (s, 1H), 10.16 (s, 1H), 8.08-7.95 (m, 6H), 7.75-7.60 (m, 2H), 7.17 (d, J = 7.6, 1H), 6.98 (s, 1H), 6.89 (s, 1H), 6.04 (t, J = 5.5, 1H), 4.21 (d, J = 5.5, 2H), 3.81 (s, 3H), 2.72 (s, 3H), 2.31 (s, 3H).<br>HPLC: 90%; MS: 512.2 (M + 1) |

TABLE 3-continued

Compounds obtained by example C with acyl chlorides

| Example No. | Used reagents | Synthesized inhibitors (mass and analytical data) |
|---|---|---|
| OR0601 | [acyl chloride: 3-(trifluoromethyl)phenylacetyl chloride] | 5-{2-Methyl-5-[2-(3-trifluoromethyl-phenyl)-acetylamino]-benzylamino}-1H-pyrrolo[2,3-b]pyridine-2-carboxylic acid methyl ester<br><br>Yield: 11%<br>$^1$H NMR (600 MHz, DMSO-d6) δ (ppm) 12.00 (s, 1H), 10.07 (s, 1H), 8.08 (d, J = 2.5, 1H), 7.64 (s, 1H), 7.61-7.56 (m, 2H), 7.56-7.51 (m, 2H), 7.43 (bs, 1H), 7.11 (d, J = 8.2, 1H), 6.95 (d, J = 2.4, 1H), 6.88 (d, J = 1.1, 1H), 6.02 (t, J = 5.5, 1H), 4.19 (d, J = 5.5, 2H), 3.83 (s, 3H), 3.70 (s, 2H), 2.28 (s, 3H)<br>HPLC: 99%; MS: 497.2 (M + 1) |
| OR1062 | [acyl chloride: 2-methoxybenzoyl chloride] | 5-[5-(2-Methoxy-benzoylamino)-2-methyl-benzylamino]-1H-pyrrolo[2,3-b]pyridine-2-carboxylic acid methyl ester<br><br>Yield: 24%<br>$^1$H NMR (300 MHz, DMSO-d6) δ (ppm) $^1$H NMR (300 MHz, DMSO) δ 12.04 (s, 1H), 10.00 (s, 1H), 8.09 (d, J = 2.0, 1H), 7.73-7.55 (m, 3H), 7.50-7.42 (m, 1H), 7.15 (t, J = 1.1, 2H), 7.09-6.97 (m, 2H), 6.90 (d, J = 2.0, 1H), 6.02 (t, J = 5.0, 1H), 4.21 (d, J = 5.0, 2H), 3.84 (s, 3H), 3.83 (s, 3H), 2.32 (s, 3H).<br>HPLC: >99%; MS: 445.2 (M + 1) |

Option 2: Synthesis of 5-{2-methyl-5-[3-amido]-benzylamino}-1H-pyrrolo[2,3-b]pyridine-2-carboxylic methyl esters by reaction of carboxylic acids All the carboxylic acids involved in this synthesis are not commercially available. First is described the synthesis of these needed carboxylic acids:

Synthesis of 4-aminomethyl-3-substituted-benzoic acids

Scheme 17 represents the general method to synthesize the 4-aminomethyl-3-substituted-benzoic acids.

Scheme 17

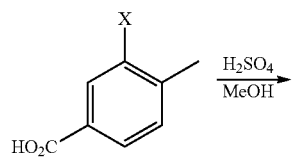
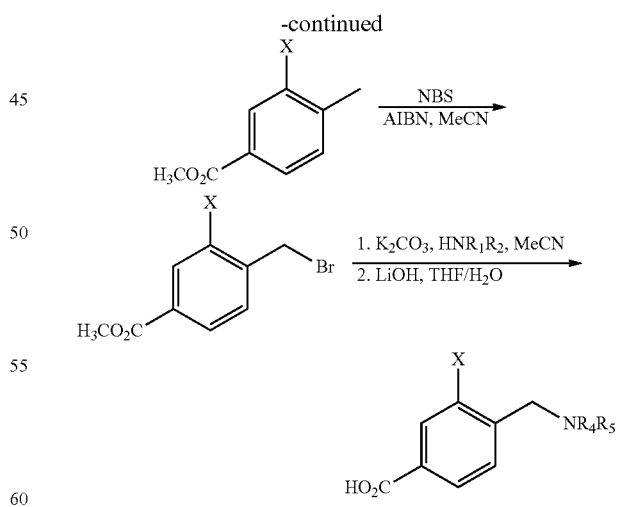

General Procedure for Esterification:

4-methyl-3-substituted benzoic acid (24 mmol) in methanol (50 mL) with $H_2SO_4$ (0.260 mL, 4.8 mmol) are stirred and heated to reflux for one night. Methanol is evaporated and product is extracted at pH=7 with EtOAc.

4-methyl-3-trifluoromethyl-benzoic acid methyl ester

Yield=95%. $^1$H NMR (300 MHz, CDCl$_3$) δ 8.25 (s, 1H), 8.04 (dd, J=1.2, 8.0, 1H), 7.33 (d, J=8.0, 1H), 3.91 (s, 3H), 2.51 (d, J=1.5, 3H).

4-methyl-3-fluoro-benzoic acid methyl ester

Yield=83% (4.0 g), HPLC: 98%, ESI-MS: [M+H]$^+$=169 Da.

General Procedure for the Bromination:

4-methyl-3-substituted benzoic acid methyl ester (18.3 mmol) in CCl$_4$ (40 mL) with NBS (3.9 g, 22 mmol) and benzoylperoxide with 25% of water (0.55 g, 1.7 mmole) are stirred and heated to reflux for 6 h. Solvent is evaporated, a water solution of K$_2$CO$_3$ is added and product is extracted with EtOAc to obtain a pale yellow solid.

4-(bromomethyl)-3-(trifluoromethyl)benzoic acid methyl ester

Yield=140% (crude).

4-(bromomethyl)-3-fluoro benzoic acid methyl ester

Yield=quant (5.9 g), ESI-MS: [M+H]$^+$=247 Da.

General Procedure for Nucleophilic Substitution on Bromomethyl:

4-(Bromomethyl)-3-substituted benzoic acid methyl ester (200 mg) in acetonitrile (5 mL) with K$_2$CO$_3$ (1.5 eq) and amine derivative (1.05 eq) were stirred and heated to reflux under argon overnight. Acetonitrile was evaporated, water (30 mL) was added and the product was extracted with AcOEt. The organic layer was washed with water, dried, filtered and concentrated. Further purification was performed by silica gel chromatography to obtain the expected product.

4-(4-Methylpiperazin-1-ylmethyl)-3-trifluoromethyl-benzoic acid methyl ester Yield=54% (1.75 g). $^1$H NMR (300 MHz, CDCl$_3$) δ 8.28 (s, 1H), 8.16 (d, J=8.1, 1H), 7.91 (d, J=8.1, 1H), 3.93 (s, 3H), 3.70 (s, 2H), 2.53 (s, 8H), 2.32 (s, 3H). ESI-MS: [M+H]$^+$=317 Da.

3-Fluoro-4-(4-methylpiperazin-1-ylmethyl)-benzoic acid methyl ester

Yield=49% (1.48 g). HPLC: 88%, ESI-MS: [M+H]$^+$=267 Da.

4-(4-Methoxycarbonyl-2-trifluoromethyl-benzyl)-piperazine-1-carboxylic acid tert-butyl ester Yield: 56% (1.89 g). HPLC: 97%. ESI-MS: [M+H]$^+$=403 Da.

4-Morpholin-4-ylmethyl-3-trifluoromethyl-benzoic acid methyl ester

Yield: 23% (343 mg). HPLC: 95%. ESI-MS: [M+H]$^+$=305 Da.

4-(4-Hydroxy-piperidin-1-ylmethyl)-3-trifluoromethyl-benzoic acid methyl ester Yield: 39% (84 mg). ESI-MS: [M+H]$^+$=318.1 Da.

4-{[2-(4-Methyl-piperazin-1-yl)-ethylamino]-methyl}-3-trifluoromethyl-benzoic acid methyl ester Yield: 20% (50 mg). ESI-MS: [M+H]$^+$=360.1 Da.

4-(4-Methyl-imidazol-1-ylmethyl)-3-trifluoromethyl-benzoic acid methyl ester Yield: 44% (90 mg). HPLC: 87% ESI-MS: [M+H]$^+$=299 Da.

4-(3-Dimethylamino-pyrrolidin-1-ylmethyl)-3-fluoro-benzoic acid methyl ester Yield: 60% (2 g). HPLC: 85% ESI-MS: [M+H]$^+$=281 Da.

General Procedure for Saponification:

Ester derivative was dissolved in THF (0.8 mol/L) and a water solution of LiOH (3 eq) was added. Mixture was heated to reflux for 4 h. THF was evaporated and impurities were extracted with EtOAc at pH=12. Aqueous layer was saturated with NaCl$_{(s)}$ and acidified until pH=3 with HCl 6 N. Product was extracted with Butan-1-ol. Butan-1-ol was evaporated and the solid obtained was washed with EtOAc to remove salts and impurities. A white solid was obtained.

4-(4-methylpiperazin-1-ylmethyl)-3-trifluoromethyl-benzoic acid

Yield=100% (1.21 g). $^1$H NMR (300 MHz, DMSO-d6) δ 10.44 (m, 1H), 8.19 (s, 1H), 8.18 (m, 1H), 7.93 (m, 1H), 3.79 (s, 2H), 2.75 (s, 3H). ESI-MS: [M+H]$^+$=303 Da.

3-Fluoro-4-(4-methylpiperazin-1-ylmethyl)-benzoic acid

Yield=65% (0.91 g). HPLC: >99%, ESI-MS: [M+H]$^+$=253 Da.

4-(4-Carboxy-2-trifluoromethyl-benzyl)-piperazine-1-carboxylic acid

Yield: 57% (265 mg). HPLC: 97% ESI-MS: [M+H]$^+$=389 Da.

4-Morpholin-4-ylmethyl-3-trifluoromethyl-benzoic acid

Yield: 35% (114 mg). ESI-MS: [M+H]$^+$=290 Da.

4-(4-Hydroxy-piperidin-1-ylmethyl)-3-trifluoromethyl-benzoic acid

Yield: 94% (128 mg). ESI-MS: [M+H]$^+$=304.1 Da.

4-{[2-(4-Methyl-piperazin-1-yl)-ethylamino]-methyl}-3-trifluoromethyl-benzoic acid Yield: 95% (176 mg). ESI-MS: [M+H]$^+$=346.1 Da.

4-(4-Methyl-imidazol-1-ylmethyl)-3-trifluoromethyl-benzoic acid

Yield: 99% (224 mg). ESI-MS: [M+H]$^+$=285 Da.

4-(3-Dimethylamino-pyrrolidin-1-ylmethyl)-3-fluoro-benzoic acid

Yield: 36% (687 mg). ESI-MS: [M+H]$^+$=267 Da.

Synthesis of 3-aminomethyl-5-trifluoromethyl-benzoic acids

Scheme 18 represents the general method to synthesize the [3-amino]-5-trifluoromethyl-benzoic acids.

Scheme 18

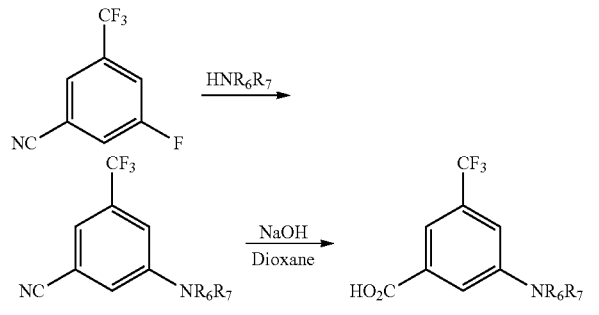

General Procedure for Nucleophilic Substitution:

A solution of 3-fluoro-5-trifluoromethyl-benzonitrile (1 eq) and the corresponding amine (3 eq) in DMA was stirred at 145° C. during 3 h. NaCl$_{(aq)}$ was added. The product was taken off into ethyl acetate. The organic layer was washed two times with water then dried over Na$_2$SO$_4$ and evaporated under reduced pressure to give a yellow solid.

3-(4-Methyl-piperazin-1-yl)-5-trifluoromethyl-benzonitrile

Yield: quantitative. HPLC: 94% ESI-MS: [M+H]$^+$=270 Da.

3-(1H-Pyrazol-3-ylamino)-5-trifluoromethyl-benzonitrile

Yield: 83%. HPLC: 92% ESI-MS: [M+H]$^+$=253 Da.

General Procedure for Hydrolysis of Nitrile:

At a solution of nitrile derivative in dioxane (0.13M) was added NaOH (10 eq, 1 g/L) in H$_2$O. The mixture was heat at reflux overnight. After evaporation of the dioxane, the aqueous layer was washed with AcOEt, then acidified with HCl 2N and extract with AcOEt. The organic layer was dried over Na$_2$SO$_4$ filtered and concentrated.

3-(4-Methyl-piperazin-1-yl)-5-trifluoromethyl-benzoic acid

Yield: 60%. HPLC: 100%. ESI-MS: [M+H]$^+$=289 Da.

3-(1H-Pyrazol-3-ylamino)-5-trifluoromethyl-benzoic acid

Yellow solid. Yield: 76% (85 mg). HPLC: 100%. ESI-MS: [M+H]$^+$=272 Da.

Synthesis of 3-(4-methyl-piperazin-1-ylmethyl)-5-trifluoromethyl-benzoic acid Scheme 19 represents the general method to synthesize the 3-(4-methyl-piperazin-1-ylmethyl)-5-trifluoromethyl-benzoic acid in 3 steps starting from 3-methyl-5-trifluoromethyl-benzonitrile.

Scheme 19

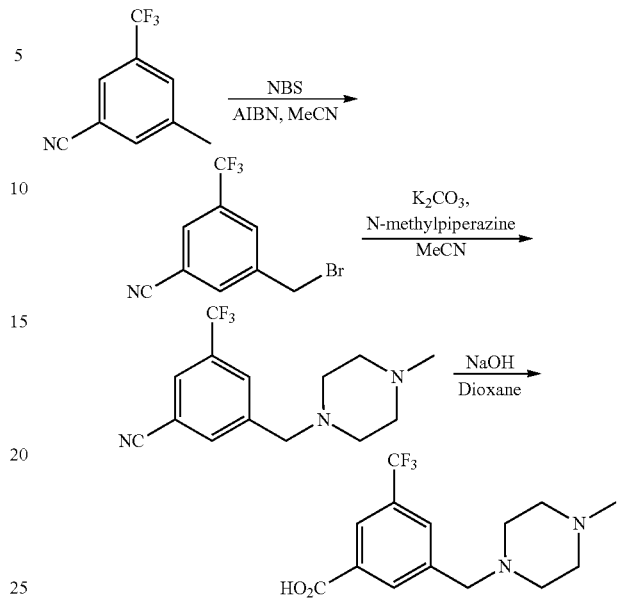

3-Bromomethyl-5-trifluoromethyl-benzonitrile 3-methyl-5-trifluoromethyl-benzonitrile in MeCN (0.42 mol/L, 1 eq)) with AIBN (0.017 eq) were stirred and heated at 85° C. under Argon. Six times, every 15 min, 0.25 eq of NBS and 0.005 eq of AIBN were added (each addition was performed at 50° C., then the mixture was heated again at 85° C.). After additions, the mixture was stirred and kept at 85° C. for 2 h. MeCN was evaporated under reduced pressure and the solid was washed with Et$_2$O and the bromide derivative was in the filtrate. Et$_2$O was evaporated under reduced pressure to give a pink solid. The crude was directly used in the next step. Yield: Not determined. HPLC purity: Not determined. ESI-MS: [M+H]$^+$=264 Da.

3-(4-Methyl-piperazin-1-ylmethyl)-5-trifluoromethyl-benzonitrile

3-Bromomethyl-5-trifluoromethyl-benzonitrile in MeCN (0.17 mol/L, 1 eq) with K$_2$CO$_3$ (2.5 eq) and methylpiperazine (1.5 eq) were stirred and heated at reflux under argon overnight. Water was added. The product was taken off into ethyl acetate. The organic layer was dried with Na$_2$SO$_4$ and evaporated under reduced pressure. The crude was directly used in the next step. Crude yield: 21%.

3-(4-Methyl-piperazin-1-ylmethyl)-5-trifluoromethyl-benzoic acid

To a solution of 3-(4-methyl-piperazin-1-ylmethyl)-5-trifluoromethyl-benzonitrile in dioxane (0.13M) was added NaOH (10 eq, 1 g/L) in H$_2$O. The mixture was heat at reflux overnight. Dioxane was evaporated under reduced pressure and the precipitate in H$_2$O was filtered and washed with H$_2$O. The filtrated was retrieved and water was removed to give a white solid. It was washed with MeOH and the filtrate was retrieved, concentrated under reduced pressure. The crude was purified on 40 g of Silicagel with CH$_2$Cl$_2$ with 1% of NEt$_3$ to MeOH with 1% of NEt$_3$. The fraction retrieved was concentrated under reduced pressure and the solid obtained was washed with a mixture of petroleum ether/AcOEt (1/1). Yield: 83%. HPLC purity: 100%. ESI-MS: [M+H]$^+$=303 Da.

Synthesis of
3-dimethylamino-5-trifluoromethyl-benzoic acid

General method to synthesize 3-dimethylamino-5-methyl-benzoic acid is represented in 2 steps by Scheme 20:

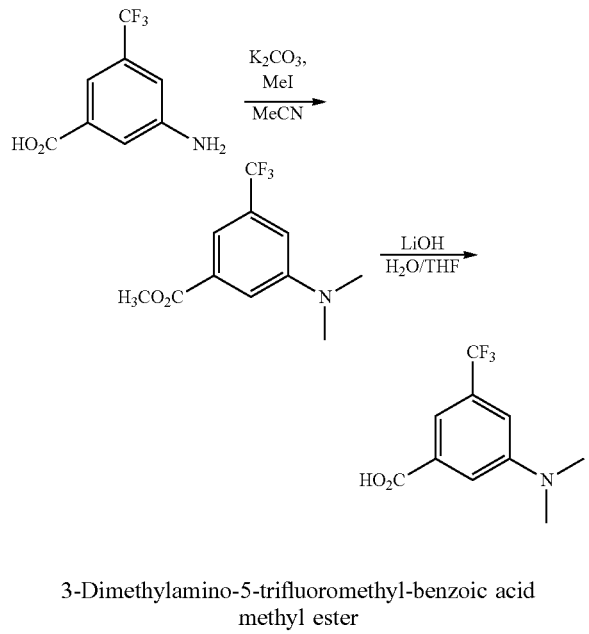

3-Dimethylamino-5-trifluoromethyl-benzoic acid methyl ester

K$_2$CO$_3$ (400 mg, 3 eq) and methyliodide (0.6 mL, 7 eq) are added to a solution of 3-amino-5-trifluoromethyl-benzoic acid (200 mg, 0.96 mmol) in acetonitrile (8 mL). The reaction mixture is heated at reflux for 2 days. Evaporation of the solvent gives 230 mg of crude 3-dimethylamino-5-trifluoromethyl-benzoic acid methyl ester which is used without further purification.

LC/MS: 97%, [M+H]+=248.1 Da.

3-Dimethylamino-5-trifluoromethyl-benzoic acid

To a solution of 3-dimethylamino-5-trifluoromethyl-benzoic acid methyl ester (240 mg) in THF (2 mL) was added a solution of LiOH (3 eq) in water (2 mL). The mixture was stirred at reflux for 4 hours. The THF was then evaporated; more water was added and acidified with HCl 2N. The product was extract with AcOEt, dried over Na$_2$SO$_4$ and concentrated to give a white solid.

Yield: 82% (183 mg), LC/MS: 90%, [M+H]+=234 Da.

General protocol for the preparation of 5-{2-methyl-5-[3-amido]-benzylamino}-1H-pyrrolo[2,3-b]pyridine-2-carboxylic methyl esters Acid derivative is dissolved in anhydrous DMF (0.06 mol/L) with DIEA (5 eq) and HATU (2 eq). After 15 min, 5-{2-methyl-5-[3-amino]-benzylamino}-1H-pyrrolo[2,3-b]pyridine-2-carboxylic methyl ester is slowly added and mixture is stirred for 12 h at RT. DMF is evaporated and saturated NaHCO$_3$ solution is added. Product is extracted with EtOAc, dried, filtered and evaporated to obtain a dark mixture. After purification by washing with MeOH or EtOAc or by silica column, expected product is obtained as a slightly yellow or orange powder.

Table 4 shows the compounds synthesized according to the synthesis scheme 16 described above, with option 2 (i.e. reaction of carboxylic acids).

TABLE 4

Compounds obtained by example C with carboxylic acids

| Example No. | Used reagents | Synthesized inhibitors (mass and analytical data) |
|---|---|---|
| OR0606 | 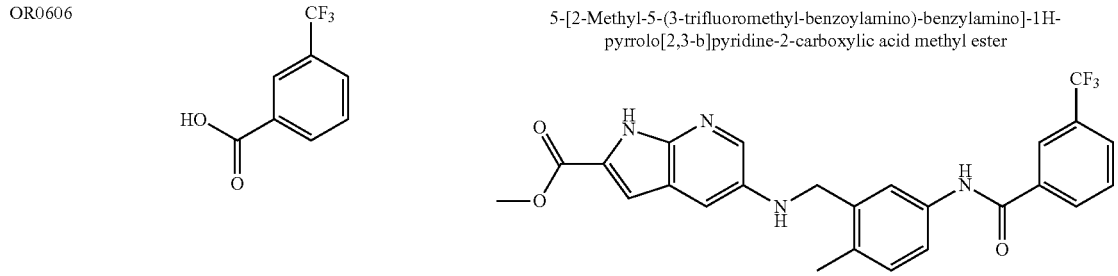 | 5-[2-Methyl-5-(3-trifluoromethyl-benzoylamino)-benzylamino]-1H-pyrrolo[2,3-b]pyridine-2-carboxylic acid methyl ester |

Yield: 6%
$^1$H NMR (400 MHz, DMSO-d6) δ (ppm) 12.03 (s, 1H), 10.38 (s, 1H), 8.25-8.19 (m, 2H), 8.10 (d, J = 2.7, 1H), 7.93 (d, J = 8.0, 1H), 7.74 (t, J = 8.0, 1H), 7.69-7.64 (m, 2H), 7.20 (d, J = 8.0, 1H), 6.98 (d, J = 2.7, 1H), 6.91-6.88 (m, 1H), 6.07 (t, J = 5.5, 1H), 4.23 (d, J = 5.5, 2H), 3.82 (s, 3H), 2.33 (s, 3H).
HPLC: 91%; MS: 483.2 (M + 1)

TABLE 4-continued

Compounds obtained by example C with carboxylic acids

| Example No. | Used reagents | Synthesized inhibitors (mass and analytical data) |
|---|---|---|
| OR0604 | 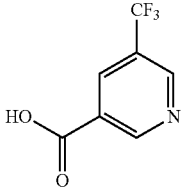 [SMILES: O=C(O)c1cncc(C(F)(F)F)c1] | 5-{2-Methyl-5-[(5-trifluoromethyl-pyridine-3-carbonyl)-amino]-benzyl-amino}-1H-pyrrolo[2,3-b]pyridine-2-carboxylic acid methyl ester<br>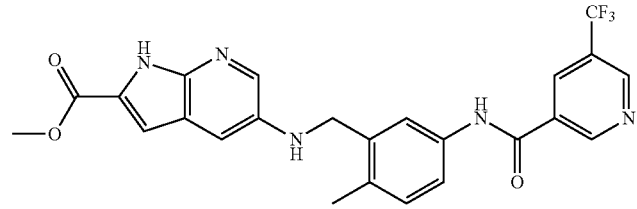<br>Yield: 13%<br>¹H NMR (400 MHz, DMSO-d6) δ (ppm) 12.02 (s, 1H), 10.52 (s, 1H), 9.32 (s, 1H), 9.14 (s, 1H), 8.62 (s, 1H), 8.09 (d, J = 2.5, 1H), 7.71-7.63 (m, 2H), 7.21 (d, J = 8.9, 1H), 6,.98-6.95 (m, 2H), 6.12 (t, J = 5.4, 1H), 4.25 (d, J = 5.4, 2H), 3.82 (s, 3H), 2.34 (s, 3H).<br>HPLC: 95%; MS: 484.2 (M + 1) |
| OR0865 | 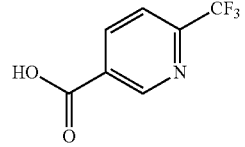 [SMILES: O=C(O)c1ccc(C(F)(F)F)nc1] | 5-{2-Methyl-5-[(6-trifluoromethyl-pyridine-3-carbonyl)-amino]-benzyl-amino}-1H-pyrrolo[2,3-b]pyridine-2-carboxylic acid methyl ester<br>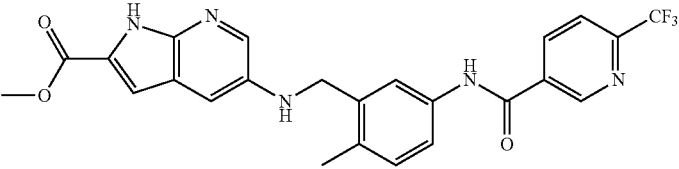<br>Yield: 14%<br>¹H NMR (300 MHz, DMSO-d6) δ (ppm) 12.05 (s, 1H), 10.53 (s, 1H), 9.18 (s, 1H), 8.50 (d, J = 8.0, 1H), 8.15-7.98 (m, 2H), 7.66 (s, 2H), 7.21 (d, J = 8.0, 1H), 7.02-6.98 (m, 1H), 6.94-6.87 (m, 1H), 6.14-6.10 (m, 1H), 4.25 (s, 2H), 3.82 (s, 3H), 2.34 (s, 3H).<br>HPLC: >99%; MS: 484 (M + 1) |
| OR0866 | 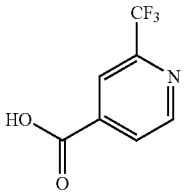 [SMILES: O=C(O)c1ccnc(C(F)(F)F)c1] | 5-{2-Methyl-5-[(2-trifluoromethyl-pyridine-4-carbonyl)-amino]-benzyl-amino}-1H-pyrrolo[2,3-b]pyridine-2-carboxylic acid methyl ester<br>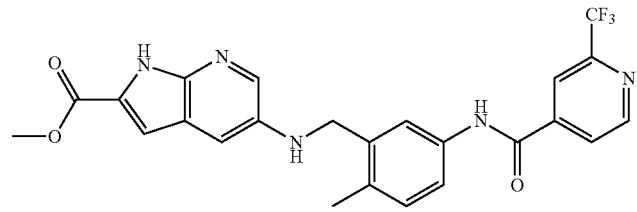<br>Yield: 6%<br>¹H NMR (300 MHz, DMSO-d6) δ (ppm) 12.05 (s, 1H), 10.59 (s, 1H), 8.94 (d, J = 5.6, 1H), 8.30 (s, 1H), 8.11 (d, J = 8.4, 2H), 7.66 (s, 2H), 7.22 (d, J = 8.4, 1H), 6.99 (s, 1H), 6.90 (s, 1H), 6.25-6.10 (m, 1H), 4.25 (s, 2H), 3.82 (s, 3H), 2.34 (s, 3H).<br>HPLC: >99%; MS: 484 (M + 1) |

TABLE 4-continued

Compounds obtained by example C with carboxylic acids

| Example No. | Used reagents | Synthesized inhibitors (mass and analytical data) |
|---|---|---|
| OR0605 | 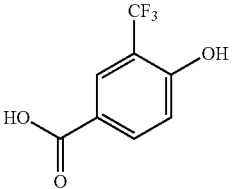 [SMILES: O=C(O)c1ccc(O)c(C(F)(F)F)c1] | 5-[5-(4-Hydroxy-3-trifluoromethyl-benzoylamino)-2-methyl-benzylamino]-1H-pyrrolo[2,3-b]pyridine-2-carboxylic acid methyl ester<br>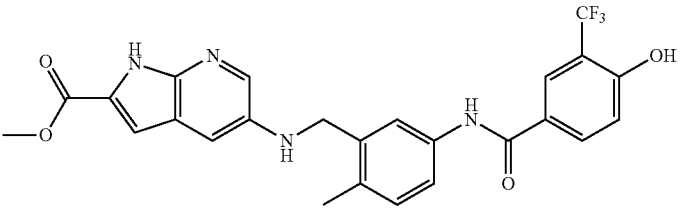<br>Yield: 15%<br>$^1$H NMR (400 MHz, DMSO-d6) δ (ppm) 12.03 (s, 1H), 10.07 (s, 1H), 8.10 (d, J = 2.9, 2H), 8.01 (d, J = 9.5, 1H), 7.70-7.58 (m, 2H), 7.18 (d, J = 8.1, 1H), 7.07-6.96 (m, 2H), 6.89 (d, J = 2.1, 1H), 6.04 (t, J = 4.8, 1H), 4.21 (d, J = 4.8, 2H), 3.82 (s, 3H), 2.32 (s, 3H).<br>HPLC: 91%; MS: 499.2 (M + 1) |
| OR0869 | 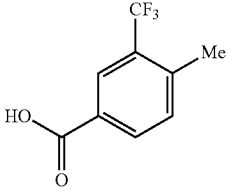 [SMILES: Cc1ccc(C(=O)O)cc1C(F)(F)F] | 5-[2-Methyl-5-(4-methyl-3-trifluoromethyl-benzoylamino)-benzylamino]-1H-pyrrolo[2,3-b]pyridine-2-carboxylic acid methyl ester<br>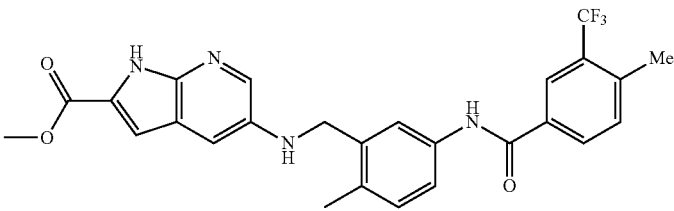<br>Yield: 26%<br>$^1$H NMR (300 MHz, DMSO-d6) δ (ppm) 12.10 (s, 1H), 10.32 (s, 1H), 8.19 (s, 1H), 8.15-8.03 (m, 2H), 7.72-7.61 (m, 2H), 7.58 (d, J = 8.1, 1H), 7.19 (d, J = 8.1, 1H), 7.10-6.98 (m, 1H), 6.92 (s, 1H), 6.17-6.12 (m, 1H), 4.24 (s, 2H), 3.83 (s, 3H), 2.60 (s, 3H), 2.32 (s, 3H).<br>HPLC: 97%; MS: 497 (M + 1) |
| OR0871 | 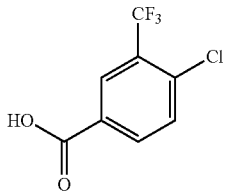 [SMILES: O=C(O)c1ccc(Cl)c(C(F)(F)F)c1] | 5-[5-(4-Chloro-3-trifluoromethyl-benzoylamino)-2-methyl-benzylamino]-1H-pyrrolo[2,3-b]pyridine-2-carboxylic acid methyl ester<br>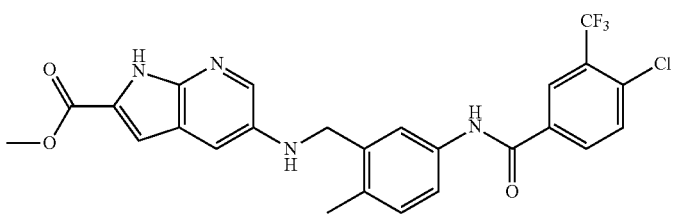<br>Yield: 5%<br>$^1$H NMR (300 MHz, DMSO-d6) δ (ppm) 12.05 (s, 1H), 10.43 (s, 1H), 8.33 (s, 1H), 8.21 (d, J = 7.9, 1H), 8.10 (s, 1H), 7.87 (d, J = 8.4, 1H), 7.65 (s, 2H), 7.20 (d, J = 8.4, 1H), 6.98 (s, 1H), 6.90 (s, 1H), 6.28-5.93 (m, 1H), 4.23 (s, 2H), 3.82 (s, 3H), 2.33 (s, 3H).<br>HPLC: 99%; MS: 517 (M + 1) |

TABLE 4-continued

Compounds obtained by example C with carboxylic acids

| Example No. | Used reagents | Synthesized inhibitors (mass and analytical data) |
|---|---|---|
| OR0607 | 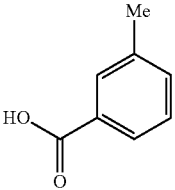 | 5-[2-Methyl-5-(3-methyl-benzoylamino)-benzylamino]-1H-pyrrolo[2,3-b]pyridine-2-carboxylic acid methyl ester<br>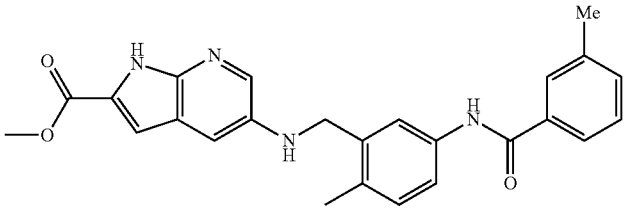<br>Yield: 28%<br>$^1$H NMR (400 MHz, DMSO-d6) δ (ppm) 12.04 (s, 1H), 10.11 (s, 1H), 8.09 (d, J = 2.5, 1H), 7.77-7.59 (m, 4H), 7.36 (2d, J = 8.7, 2H), 7.17 (d, J = 8.2, 1H), 6.98 (s, J = 2.5, 1H), 6.90 (d, J = 2.1, 1H), 6.05 (t, J = 5.2, 1H), 4.21 (d, J = 5.2, 2H), 3.82 (s, 3H), 2.34 (2s, 6H).<br>HPLC: 93%; MS: 429.2 (M + 1) |
| OR0867 | 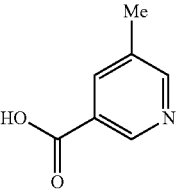 | 5-{2-Methyl-5-[(5-methyl-pyridine-3-carbonyl)-amino]-benzylamino}-1H-pyrrolo[2,3-b]pyridine-2-carboxylic acid methyl ester<br>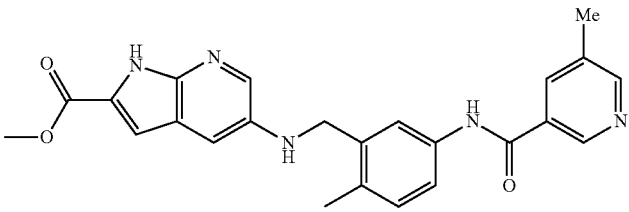<br>Yield: 20%<br>$^1$H NMR (300 MHz, DMSO-d6) δ (ppm) 12.01 (s, 1H), 10.28 (s, 1H), 8.85 (s, 1H), 8.55 (s, 1H), 8.18-7.96 (m, 2H), 7.81-7.58 (m, 2H), 7.21 (s, 1H), 6.93 (s, 2H), 6.09 (s, 1H), 4.24 (s, 2H), 3.81 (s, 3H), 2.42-2.22 (m, 6H).<br>HPLC: 98%; MS: 430 (M + 1) |
| OR0868 | 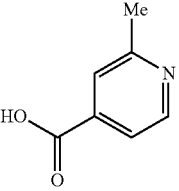 | 5-{2-Methyl-5-[(2-methyl-pyridine-4-carbonyl)-amino]-benzylamino}-1H-pyrrolo[2,3-b]pyridine-2-carboxylic acid methyl ester<br>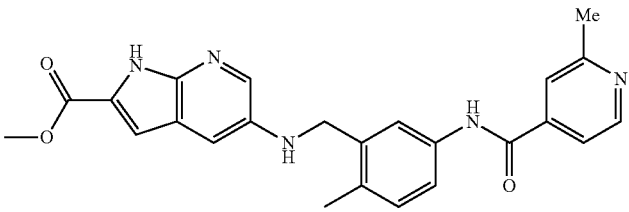<br>Yield: 20%<br>$^1$H NMR (300 MHz, DMSO-d6) δ (ppm) 12.01 (s, 1H), 10.33 (s, 1H), 8.57 (d, J = 4.5, 1H), 8.10 (d, J = 2.3, 1H), 7.75-7.62 (m, 3H), 7.58 (d, J = 4.5, 1H), 7.19 (d, J = 7.6, 1H), 6.97 (d, J = 2.3, 1H), 6.89 (s, 1H), 6.08 (t, J = 5.3, 1H), 4.22 (s, 2H), 3.82 (s, 3H), 2.53 (s, 3H), 2.33 (s, 3H).<br>HPLC: 94%; MS: 430 (M + 1) |

TABLE 4-continued

Compounds obtained by example C with carboxylic acids

| Example No. | Used reagents | Synthesized inhibitors (mass and analytical data) |
|---|---|---|
| OR0608 | 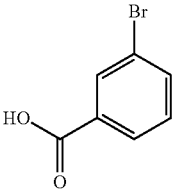 | 5-[5-(3-Bromo-benzoylamino)-2-methyl-benzylamino]-1H-pyrrolo[2,3-b]pyridine-2-carboxylic acid methyl ester<br>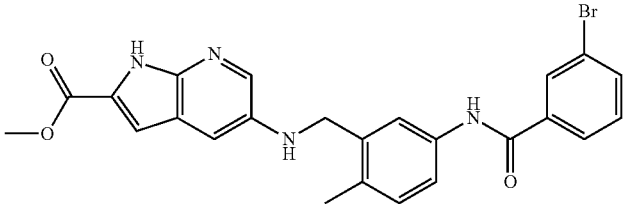<br>Yield: 24%<br>$^1$H NMR (400 MHz, DMSO-d6) δ (ppm) 10.25 (s, 1H), 8.14-8.06 (m, 2H), 7.90 (d, J = 7.9, 1H), 7.75 (d, J = 9.0, 1H), 7.70-7.62 (m, 2H), 7.45 (t, J = 7.9, 1H), 7.18 (d, J = 7.9, 1H), 6.98 (d, J = 2.6, 1H), 6.90 (d, J = 2.1, 1H), 6.07 (t, J = 5.4, 1H), 4.22 (d, J = 5.4, 2H), 3.82 (s, 4H), 2.32 (s, 3H).<br>HPLC: 90%; MS: 493.1 (M + 1) |
| OR0610 | 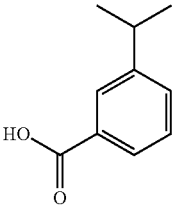 | 5-[5-(3-Isopropyl-benzoylamino)-2-methyl-benzylamino]-1H-pyrrolo[2,3-b]pyridine-2-carboxylic acid methyl ester<br>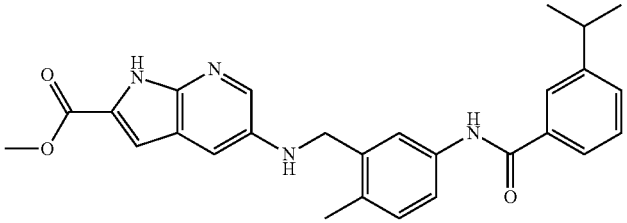<br>Yield: 26%<br>$^1$H NMR (600 MHz, DMSO-d6) δ (ppm) 12.00 (s, 1H), 10.08 (s, 1H), 8.10 (d, J = 2.4, 1H), 7.76 (s, 1H), 7.73-7.68 (m, 2H), 7.64 (d, J = 8.2, 1H), 7.43 (t, J = 7.6, 1H), 7.39 (t, J = 7.6, 1H), 7.17 (d, J = 8.2, 1H), 7.00 (d, J = 2.4, 1H), 6.90 (d, J = 1.9, 1H), 6.00 (t, J = 5.4, 1H), 4.22 (d, J = 5.4, 2H), 3.83 (s, 3H), 2.99-2.93 (q, J = 7.0, 1H), 2.33 (s, 3H), 1.23 (d, J = 7.0, 6H).<br>HPLC: 95%; MS: 457.3 (M + 1) |
| OR0611 | 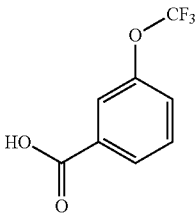 [SMILES: O=C(O)c1cccc(OC(F)(F)F)c1] | 5-[2-Methyl-5-(3-trifluoromethoxy-benzoylamino)-benzylamino]-1H-pyrrolo[2,3-b]pyridine-2-carboxylic acid methyl ester<br>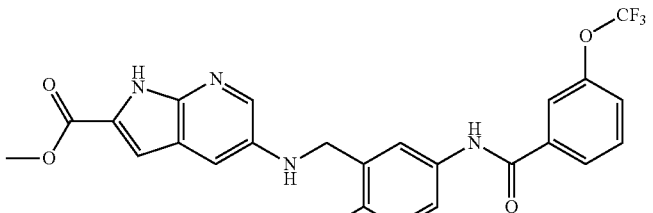<br>Yield: 25%<br>$^1$H NMR (400 MHz, DMSO-d6) δ (ppm) 12.04 (s, 1H), 10.30 (s, 1H), 8.09 (d, J = 2.6, 1H), 7.96 (d, J = 7.8, 1H), 7.86 (s, 1H), 7.70-7.61 (m, 3H), 7.60-7.55 (m, 1H), 7.19 (d, J = 8.2, 1H), 6.97 (d, J = 2.5, 1H), 6.89 (d, J = 2.1, 1H), 6.08 (t, J = 5.3, 1H), 4.22 (d, J = 5.3, 2H), 3.82 (s, 3H), 2.33 (s, 3H).<br>HPLC: 93%; MS: 499.2 (M + 1) |

TABLE 4-continued

Compounds obtained by example C with carboxylic acids

| Example No. | Used reagents | Synthesized inhibitors (mass and analytical data) |
|---|---|---|
| OR0612 | 4-trifluoromethyl-cyclohexanecarboxylic acid | 5-{2-Methyl-5-[(4-trifluoromethyl-cyclohexanecarbonyl)-amino]-benzylamino}-1H-pyrrolo[2,3-b]pyridine-2-carboxylic acid methyl ester<br><br>Yield: 20%<br>$^1$H NMR (400 MHz, DMSO-d6) δ (ppm) 12.03 (s, 1H), 9.69 (d, J = 19.6, 1H), 8.07 (s, 1H), 7.52 (d, J = 8.2, 1H), 7.43 (s, 1H), 7.09 (d, J = 8.2, 1H), 6.96 (dd, J = 8.0 and 2.6, 1H), 6.89 (s, 1H), 6.07-5.97 (m, 1H), 4.17 (d, J = 5.1, 2H), 3.82 (s, 3H), 2.28 (s, 3H), 1.90-1.80 (m, 2H), 1.75-1.47 (m, 6H), 1.30-1.15 (m, 2H).<br>HPLC: 92%; MS: 489.1 (M + 1) |
| OR0615 | benzo[1,3]dioxole-5-carboxylic acid | 5-{5-[(Benzo[1,3]dioxole-5-carbonyl)-amino]-2-methyl-benzylamino}-1H-pyrrolo[2,3-b]pyridine-2-carboxylic acid methyl ester<br><br>Yield: 10%<br>$^1$H NMR (600 MHz, DMSO-d6) δ (ppm) 12.01 (s, 1H), 9.95 (s, 1H), 8.10 (d, J = 1.8, 1H), 7.68 ppm (s, 1H), 7.62 (d, J = 8.1, 1H), 7.53 (d, J = 8.4, 1H), 7.47 (s, 1H), 7.16 (d, J = 8.1, 1H), 7.00 (d, J = 8.8, 2H), 6.90 (s, 1H), 6.10 (s, 2H), 6.01 (t, J = 4.7, 1H), 4.21 (d, J = 4.7, 2H), 3.83 (s, 3H), 2.32 (s, 3H).<br>HPLC: 94%; MS: 459.1 (M + 1) |
| OR0616 | 3H-benzotriazole-5-carboxylic acid | 5-{5-[(3H-Benzotriazole-5-carbonyl)-amino]-2-methyl-benzylamino}-1H-pyrrolo[2,3-b]pyridine-2-carboxylic acid methyl ester<br><br>Yield: 14%<br>$^1$H NMR (600 MHz, DMSO-d6) δ (ppm) 12.02 (s, 1H), 10.26 (s, 1H), 8.52 (s, 1H), 8.10 (d, J = 2.7, 1H), 7.89 (s, 1H), 7.72 (s, 2H), 7.68 (d, J = 7.8, 2H), 7.19 (d, J = 8.3, 1H), 7.00 (s, 1H), 6.90 (s, 1H), 6.05 (t, J = 5.3, 1H), 4.22 (d, J = 5.3, 2H), 3.82 (s, 3H), 2.33 (s, 3H).<br>HPLC: 93%; MS: 456.2 (M + 1) |

TABLE 4-continued

Compounds obtained by example C with carboxylic acids

| Example No. | Used reagents | Synthesized inhibitors (mass and analytical data) |
|---|---|---|
| OR0617 | 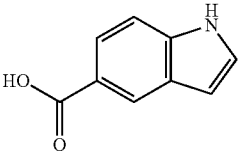 [SMILES: O=C(O)c1ccc2[nH]ccc2c1] | 5-{5-[(1H-Indole-5-carbonyl)-amino]-2-methyl-benzylamino}-1H-pyrrolo[2,3-b]pyridine-2-carboxylic acid methyl ester 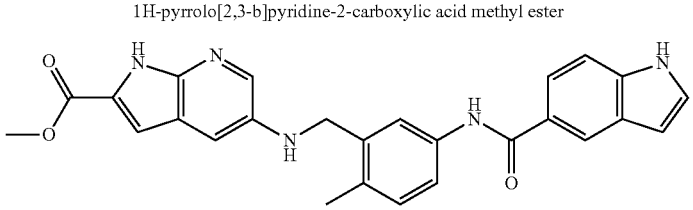 Yield: 44% $^1$H NMR (200 MHz, DMSO-d6) δ (ppm) 12.07 (s, 1H), 11.38 (s, 1H), 10.05 (s, 1H), 8.23 (s, 1H), 8.13 (d, J = 2.6, 1H), 7.73 (dd, J = 1.7 and 6.5, 2H), 7.67 (d, J = 1.7, 1H), 7.51-7.42 (m, 2H), 7.18 (d, J = 8.2, 1H), 7.02 (d, 1H), 6.92 (s, 1H), 6.57 (s, 1H), 6.07 (s, 1H), 4.22 (s, 2H), 3.84 (s, 3H), 2.34 (s, 3H). HPLC: 92%; MS: 454.0 (M + 1) |
| OR0975 | 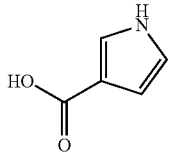 | 5-{2-Methyl-5-[(1H-pyrrole-3-carbonyl)-amino]-benzylamino}-1H-pyrrolo[2,3-b]pyridine-2-carboxylic acid methyl ester 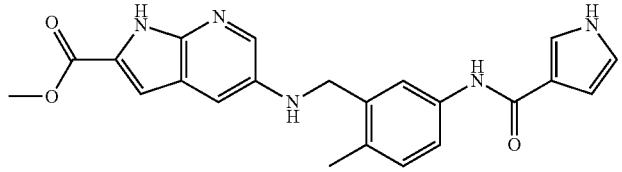 Yield: 55% $^1$H NMR (300 MHz, DMSO-d6) δ (ppm) 12.06 (s, 1H), 11.21 (s, 1H), 9.39 (s, 1H), 8.10 (s, 1H), 7.71-7.56 (m, 1H), 7.64-7.56 (m, 1H), 7.51-7.42 (m, 1H), 7.12 (d, J = 7.9 Hz, 1H), 7.07-6.99 (m, 1H), 6.95-6.87 (m, 1H), 6.81-6.73 (m, 1H), 6.64-6.56 (m, 1H), 6.30-5.75 (m, 1H), 4.20 (s, 2H), 3.83 (s, 3H), 2.30 (s, 3H). HPLC: 98%; MS: 404 (M + 1) |
| OR0512 | 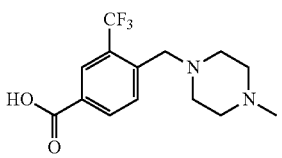 | 5-{2-Methyl-5-[4-(4-methyl-piperazin-1-ylmethyl)-3-trifluoromethyl-benzoyl-amino]-benzylamino}-1H-pyrrolo[2,3-b]pyridine-2-carboxylic acid methyl ester 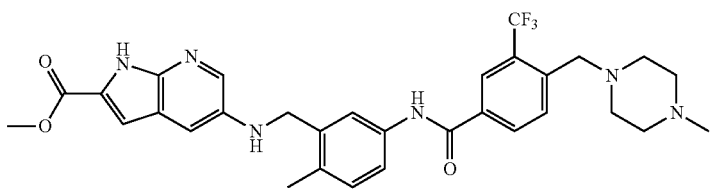 Yield: 16% $^1$H NMR (400 MHz, DMSO-d6) δ (ppm) 12.04 (s, 1H), 10.35 (s, 1H), 8.23-8.15 (m, 2H), 8.08 (d, J = 2.6, 1H), 7.85 (d, J = 8.0, 1H), 7.64 (d, J = 8.0, 2H), 7.19 (d, J = 7.9, 1H), 6.96 (d, J = 2.5, 1H), 6.88 (d, J = 2.1, 1H), 6.08 (s, J = 5.5, 1H), 4.22 (d, J = 5.5, 2H), 3.81 (s, 3H), 3.73 (s, 2H), 2.44-2.34 (m, 8H), 2.32 (s, 3H), 2.16 (s, 3H). HPLC: 94%; MS: 595.2 (M + 1) |

TABLE 4-continued

Compounds obtained by example C with carboxylic acids

| Example No. | Used reagents | Synthesized inhibitors (mass and analytical data) |
|---|---|---|
| OR0864 | 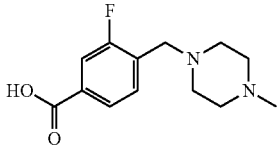 | 5-{5-[3-Fluoro-4-(4-methyl-piperazin-1-ylmethyl)-benzoylamino]-2-methyl-benzylamino}-1H-pyrrolo[2,3-b]pyridine-2-carboxylic acid methyl ester 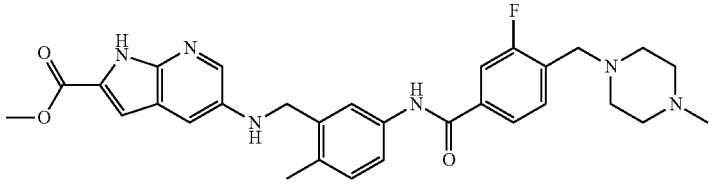 Yield: 3% $^1$H NMR (300 MHz, DMSO-d6) δ (ppm) 12.07 (s, 1H), 10.26-10.15 (m, 1H), 8.14 (s, 1H), 7.81-7.65 (m, 4H), 7.54 (t, J = 7.1, 1H), 7.22 (d, J = 8.5, 1H), 7.02 (d, J = 1.8, 1H), 6.93 (d, J = 1.8, 1H), 6.10 (t, J = 5.3, 1H), 4.26 (d, J = 5.3, 2H), 3.86 (s, 3H), 3.59 (s, 2H), 2.43-2.39 (m, 11H), 2.20 (s, 3H). HPLC: 92%; MS: 545 (M + 1) |
| OR0598 | 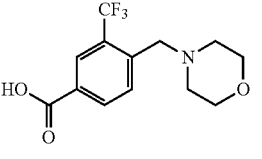 | 5-[2-Methyl-5-(4-morpholin-4-ylmethyl-3-trifluoromethyl-benzoylamino)-benzylamino]-1H-pyrrolo[2,3-b]pyridine-2-carboxylic acid methyl ester 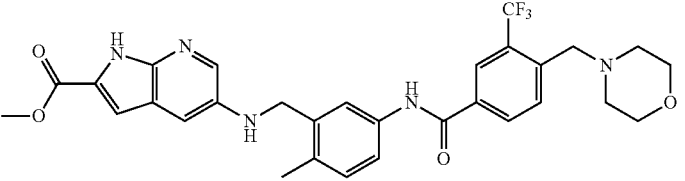 Yield: 22% $^1$H NMR (400 MHz, DMSO-d6) δ (ppm) 12.03 (s, 1H), 10.34 (s, 1H), 8.20 (s, 1H), 8.17 (d, J = 8.2, 1H), 8.09 (d, J = 2.5, 1H), 7.90 (d, J = 7.4, 1H), 7.66 (s, 1H), 7.65 (d, J = 7.4, 1H), 7.19 (d, J = 8.2, 1H), 6.98 (d, J = 2.6, 1H), 6.90 (s, 1H), 6.06 (t, J = 5.3, 1H), 4.22 (d, J = 5.3, 2H), 3.82 (s, 3H), 3.67 (s, 2H), 3.62-3.56 (m, 4H), 2.43-2.35 (m, 4H), 2.33 (s, 3H). HPLC: 89%; MS: 582.3 (M + 1) |
| OR0613 | 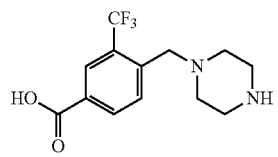 [SMILES: O=C(O)c1ccc(CN2CCNCC2)c(C(F)(F)F)c1] | 5-[2-Methyl-5-(4-piperazin-1-ylmethyl-3-trifluoromethyl-benzoylamino)-benzylamino]-1H-pyrrolo[2,3-b]pyridine-2-carboxylic acid methyl ester 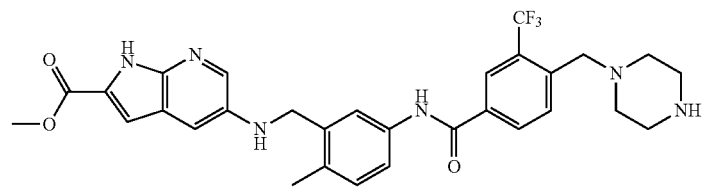 Yield: 13% $^1$H NMR (400 MHz, DMSO-d6) δ (ppm) 12.02 (s, 1H), 10.33 (s, 1H), 8.20-8.13 (m, 2H), 8.09 (d, J = 2.4, 1H), 7.88 (d, J = 8.6, 1H), 7.69-7.64 (m, 3H), 7.20 (d, J = 8.6, 1H), 6.98 (d, J = 2.4 1H), 6.89 (s, 1H), 6.06 (t, J = 5.2, 1H), 4.22 (d, J = 5.2, 2H), 3.82 (s, 3H), 3.61 (s, 2H), 2.69 (b, 3H), 2.33 (bs, 6H). HPLC: 91%; MS: 581.2 (M + 1) |

TABLE 4-continued

Compounds obtained by example C with carboxylic acids

| Example No. | Used reagents | Synthesized inhibitors (mass and analytical data) |
|---|---|---|
| OR0636 | | 5-{5-[4-(4-Hydroxy-piperidin-1-ylmethyl)-3-trifluoromethyl-benzoylamino]-2-methyl-benzylamino}-1H-pyrrolo[2,3-b]pyridine-2-carboxylic acid methyl ester<br><br>Yield: 48%<br>$^1$H NMR (300 MHz, DMSO-d6) δ (ppm) 12.03 (s, 1H), 10.34 (s, 1H), 8.21-8.13 (m, 2H), 8.10 (d, J = 2.6, 1H), 7.89 (d, J = 8.6, 1H), 7.69-7.62 (m, 2H), 7.19 (d, J = 8.9, 1H), 6.98 (d, J = 2.6, 1H), 6.90 (d, J = 2.1, 1H), 6.09 (t, J = 5.3, 1H), 4.57 (d, J = 4.1, 1H), 4.23 (d, J = 5.3, 2H), 3.82 (s, 3H), 3.62 (s, 2H), 3.54-3.43 (m, 1H), 2.70-2.59 (m, 2H), 2.33 (s, 3H), 2.16-2.04 (m, 2H), 1.77-1.65 (m, 2H), 1.49-1.33 (m, 2H).<br>HPLC: 91%; MS: 596.2 (M + 1) |
| OR0637 | | 5-[2-Methyl-5-(4-{[2-(4-methyl-piperazin-1-yl)-ethylamino]-methyl}-3-trifluoromethyl-benzoylamino)-benzylamino]-1H-pyrrolo[2,3-b]pyridine-2-carboxylic acid methyl ester<br><br>Yield: 21%<br>$^1$H NMR (300 MHz, DMSO) δ (ppm) 12.03 (s, 1H), 10.33 (s, 1H), 8.25-8.14 (m, 2H), 8.10 (d, J = 2.6, 1H), 7.88 (d, J = 8.5, 1H), 7.74-7.61 (m, 2H), 7.19 (d, J = 8.5, 1H), 6.98 (d, J = 2.4, 1H), 6.89 (d, J = 1.2, 1H), 6.07 (t, J = 5.4, 1H), 4.23 (d, J = 5.4, 2H), 3.91 (s, 2H), 3.82 (s, 3H), 2.60 (t, J = 6.4, 3H), 2.45-2.20 (m, 14H), 2.12 (s, 3H).<br>HPLC: 92%; MS: 639.3 (M + 1) |
| OR0639 | | 5-{2-Methyl-5-[4-(4-methyl-imidazol-1-ylmethyl)-3-trifluoromethyl-benzoylamino]-benzylamino}-1H-pyrrolo[2,3-b]pyridine-2-carboxylic acid methyl ester<br><br>Yield: 9%<br>$^1$H NMR (300 MHz, DMSO) δ (ppm) 12.03 (s, 1H), 10.36 (s, 1H), 8.24 (s, 1H), 8.20-8.04 (m, 2H), 7.75-7.56 (m, 3H), 7.19 (d, J = 8.6, 1H), 7.09 (d, J = 8.1, 1H), 7.04-6.78 (m, 3H), 6.07 (t, J = 5.0, 1H), 5.38 (s, 2H), 4.21 (d, J = 5.0, 2H), 3.82 (s, 3H), 2.33 (s, 3H), 2.11 (s, 3H).<br>HPLC: 87%; MS 577.2 (M + 1) |

TABLE 4-continued

*Compounds obtained by example C with carboxylic acids*

| Example No. | Used reagents | Synthesized inhibitors (mass and analytical data) |
|---|---|---|
| OR0974 | (structure) | 5-{5-[4-(3-Dimethylamino-pyrolidin-1-ylmethyl)-3-fluoro-benzoylamino]-2-methyl-benzylamino}-1H-pyrrolo[2,3-b]pyridine-2-carboxylic acid methyl ester<br><br>Yield: 10%<br>$^1$H NMR (300 MHz, DMSO) δ (ppm) 12.01 (s, 1H), 10.21 (s, 1H), 8.13 (d, J = 2.6, 1H), 7.78-7.67 (m, 5H), 7.56 (d, J = 7.6, 1H), 7.22 (d, J = 7.6, 1H), 7.01 (d, J = 2.6, 1H), 6.93 (s, 1H), 6.10 (t, J = 6.5, 1H), 4.26 (d, J = 6.5, 2H), 3.86 (s, 3H), 3.72-3.58 (m, 2H), 2.75-2.63 (m, 2H), 2.42-2.36 (m, 3H), 2.32 (s, 1H), 2.10 (s, 6H), 1.95-1.77 (m, 1H), 1.71-1.53 (m, 1H).<br>HPLC: 96%; MS: 559 (M + 1) |
| OR0642 | (structure) | 5-{2-Methyl-5-[3-(1H-pyrazol-3-ylamino)-5-trifluoromethyl-benzoylamino]-benzyl-amino}-1H-pyrrolo[2,3-b]pyridine-2-carboxylic acid methyl ester<br><br>Yield: 15%<br>$^1$H NMR (300 MHz, DMSO) δ (ppm) 12.04 (s, 1H), 10.43 (s, 1H), 8.41 (s, 1H), 8.38 (d, J = 2.6, 1H), 8.13-8.08 (m, 2H), 7.91 (s, 1H), 7.71-7.63 (m, 2H), 7.21 (d, J = 7.9, 1H), 6.98 (d, J = 5.2, 1H), 6.89 (s, J = 1.7, 1H), 6.09 (t, J = 5.3, 1H), 5.83 (d, J = 2.6, 1H), 5.31 (s, 2H), 4.25 (d, J = 5.3, 2H), 3.82 (s, 3H), 2.34 (s, 3H).<br>HPLC: 84%; MS: 564.1 (M + 1) |
| OR0698 | (structure) | 5-{2-Methyl-5-[3-(4-methyl-piperazin-1-yl)-5-trifluoromethyl-benzoylamino]-benzyl-amino}-1H-pyrrolo[2,3-b]pyridine-2-carboxylic acid methyl ester<br><br>Yield: 6%<br>$^1$H NMR (300 MHz, DMSO) δ (ppm) 12.04 (s, 1H), 10.26 (s, 1H), 8.10 (d, J = 2.5, 1H), 7.72-7.61 (m, 3H), 7.58 (s, 1H), 7.34 (s, 1H), 7.20 (d, J = 8.2, 1H), 6.99 (d, J = 2.5, 1H), 6.90 (d, J = 2.0, 1H), 6.06 (t, J = 4.1 1H), 4.22 (d, J = 4.1, 2H), 3.83 (s, 3H), 2.58-2.52 (m, 4H), 2.53-2.48 (m, 4H), 2.34 (s, 3H), 2.29 (s, 3H).<br>HPLC: 97%; MS: 581.3 (M + 1) |

TABLE 4-continued

Compounds obtained by example C with carboxylic acids

| Example No. | Used reagents | Synthesized inhibitors (mass and analytical data) |
|---|---|---|
| OR0699 | 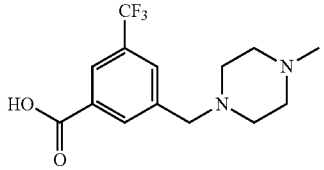 | 5-{2-Methyl-5-[3-(4-methyl-piperazin-1-ylmethyl)-5-trifluoromethyl-benzoylamino]-benzylamino}-1H-pyrrolo[2,3-b]pyridine-2-carboxylic acid methyl ester<br>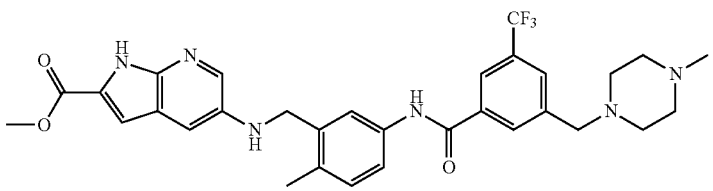<br>Yield: 11%.<br>$^1$H NMR (300 MHz, DMSO) δ (ppm) 12.25-11.82 (m, 1H), 10.38 (s, 1H), 8.19-8.01 (m, 3H), 7.81 (s, 1H), 7.67 (s, 1H), 7.65 (d, J = 7.4, 1H), 7.21 (d, J = 7.1, 1H), 6.99 (d, J = 2.5, 1H), 6.90 (s, 1H), 6.08 (t, J = 5.4, 1H), 4.24 (d, J = 5.4, 2H), 3.83 (s, 3H), 3.60 (s, 2H), 2.42-2.18 (m, 11H), 2.14 (s, 3H).<br>HPLC: 97%; MS: 595.3 (M + 1) |
| OR0597 | 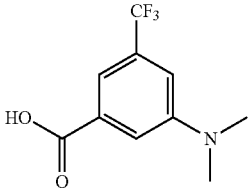 | 5-[5-(3-Dimethylamino-5-trifluoromethyl-benzoylamino)-2-methyl-benzylamino]-1H-pyrrolo[2,3-b]pyridine-2-carboxylic acid methyl ester<br>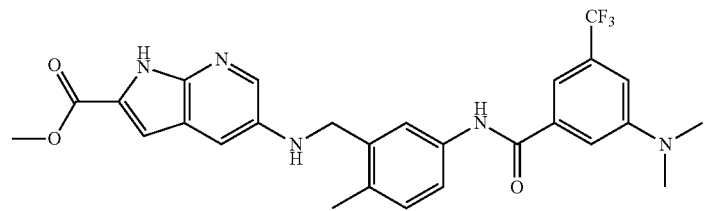<br>Yield: 23%<br>$^1$H NMR (200 MHz, DMSO-d6) δ (ppm) 1.05 (s, 1H), 10.25 (s, 1H), 8.09 (s, 1H), 7.73-7.55 (m, 2H), 7.50-7.34 (m, 2H), 7.20 (d, J = 8.0, 1H), 7.01 (d, J = 10.2, 2H), 6.89 (s, 1H), 6.13-5.98 (m, 1H), 4.21 (s, 2H), 3.82 (s, 3H), 3.01 (s, 6H), 2.32 (s, 3H).<br>HPLC: 90%; MS: 526.2 (M + 1) |

Example D

Synthesis of 5-{5-[4-(4-methyl-piperazin-1-ylmethyl)-3-trifluoromethyl-benzoylamino]-benzylamino}-1H-pyrrolo[2,3-b]pyridine-2-carboxylic acid methyl esters in 3 stages starting from the commercial reagent from the company OriBase Pharma Scheme 21 represents a general method of synthesis of 5-{5-[4-(4-methyl-piperazin-1-ylmethyl)-3-trifluoromethyl-benzoylamino]-benzylamino}-1H-pyrrolo[2,3-b]pyridine-2-carboxylic acid methyl ester in 3 steps.

Scheme 21 - General synthesis scheme of example D

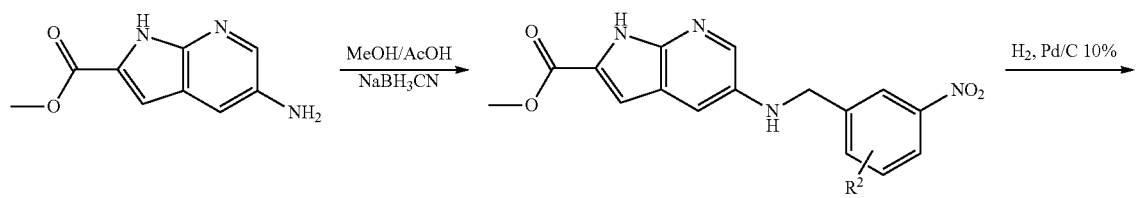

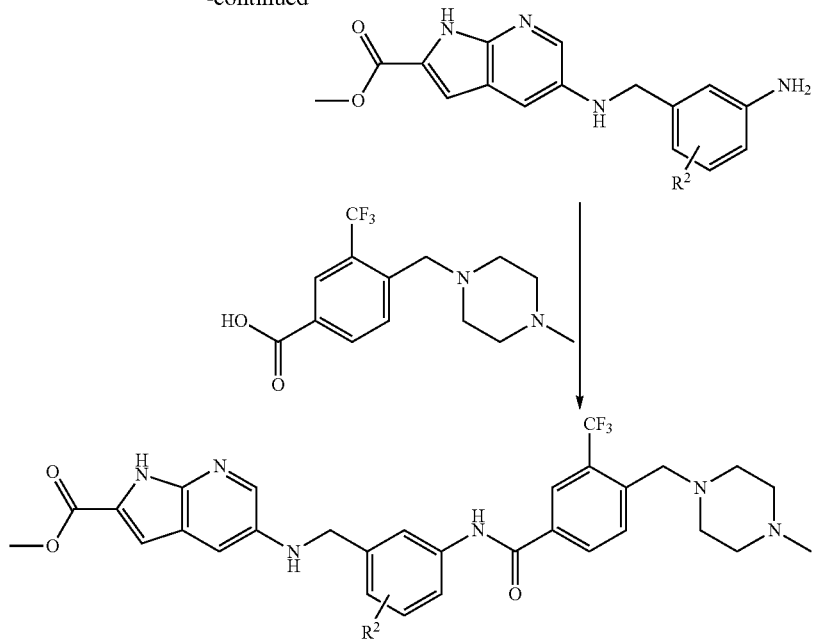

Step 1: General protocol for the preparation of 5-(3-nitro-benzylamino)-1H-pyrrolo[2,3-b]pyridine-2-carboxylic acid methyl esters 5-Amino-1H-pyrrolo[2,3-b]pyridine-2-carboxylic acid methyl ester (100 mg) and the nitrobenzaldehyde derivative (1 eq) were stirred in a mixture of MeOH and AcOH (10%) for 2 h. Then NaBH$_3$CN (2 eq) was slowly added and the mixture was stirred under argon at RT overnight. Solvents were evaporated and a saturated solution of NaHCO$_3$ was added until neutrality. The aqueous layer was extracted by EtOAc. The organic layer was dried over Na2SO4, filtered and concentrated to give the expected product.

5-(2-Chloro-5-nitro-benzylamino)-1H-pyrrolo[2,3-b]pyridine-2-carboxylic acid methyl ester Yellow powder. Yield: 85% (158 mg). HPLC: 80%. MS: 361 (M+1).

5-(2-Fluoro-5-nitro-benzylamino)-1H-pyrrolo[2,3-b]pyridine-2-carboxylic acid methyl ester Yellow solid. Yield: 74% (800 mg). HPLC: >99%. MS: 345 (M+1).

5-(3-Nitro-4-methyl-benzylamino)-1H-pyrrolo[2,3-b]pyridine-2-carboxylic acid methyl ester Yellow solid. Yield: 86% (152 mg). HPLC: 85%. MS: 341 (M+1).

5-(3-nitro-benzylamino)-1H-pyrrolo[2,3-b]pyridine-2-carboxylic acid methyl ester Brown powder. Yield: 87% (443 mg). HPLC: 94%. MS: 327 (M+1).

Step 2: General protocol for the preparation of 5-(3-amino-benzylamino)-1H-pyrrolo[2,3-b]pyridine-2-carboxylic acid methyl esters 5-(Nitro-benzylamino)-1H-pyrrolo[2,3-b]pyridine-2-carboxylic acid methyl ester derivative (200 mg), methanol (150 mL) and palladium 10% on charcoal (10% w/w) were put in an autoclave filled with 30 bar of dihydrogen and stirred for 48 h. Mixture was filtered on celite and washed with methanol. Solvent is evaporated to give the expected product 5-(5-Amino-3-chloro-benzylamino)-1H-pyrrolo[2,3-b]pyridine-2-carboxylic acid methyl ester Yellow powder. Yield: 99% (183 mg). HPLC: 77%. MS: 331 (M+1).

5-(5-Amino-3-fluoro-benzylamino)-1H-pyrrolo[2,3-b]pyridine-2-carboxylic acid methyl ester Brown powder. Yield: 43% (311 mg). HPLC: 93%. MS: 315 (M+1).

5-(3-Amino-4-methyl-benzylamino)-1H-pyrrolo[2,3-b]pyridine-2-carboxylic acid methyl ester Yellow powder. Yield: 90% (240 mg). HPLC: 85%. MS: 311 (M+1).

5-(3-amino-benzylamino)-1H-pyrrolo[2,3-b]pyridine-2-carboxylic acid methyl ester Off-white powder. Yield: 87% (351 mg). HPLC: 99%. MS: 297 (M+1).

Step 3: General protocol for the preparation of 5-{5-[4-(4-methyl-piperazin-1-ylmethyl)-3-trifluoromethyl-benzoylamino]-benzylamino}-1H-pyrrolo[2,3-b]pyridine-2-carboxylic acid methyl esters 4-(4-Methyl-piperazin-1-ylmethyl)-3-trifluoromethyl-benzoic acid is dissolved in anhydrous DMF (0.06 mol/L) with DIEA (5 eq) and HATU (2 eq). After 15 min, the amine derivative is slowly added and mixture is stirred for 12 h at RT. DMF is evaporated and NaHCO$_{3(aq)}$ is added. Product is extracted with EtOAc, dried, filtered and evaporated to obtain a dark mixture. After purification by washing with MeOH or EtOAc or by silica column, expected product is obtained as a slightly yellow or orange powder.

Table 5 shows the compounds synthesized according to the synthesis Scheme 21 described above.

TABLE 5

Compounds obtained by example D

| Example No. | Used reagents | Synthesized inhibitors (mass and analytical data) |
|---|---|---|
| OR0621 | 4-[(4-methyl-piperazin-1-ylmethyl)]-3-trifluoromethyl-benzoic acid | 5-{2-Chloro-5-[4-(4-methyl-piperazin-1-ylmethyl)-3-trifluoromethyl-benzoyl-amino]-benzylamino}-1H-pyrrolo[2,3-b]pyridine-2-carboxylic acid methyl ester<br><br>Yield: 37%<br>$^1$H NMR (300 MHz, DMSO) δ 12.05 (s, 1H), 10.59 (s, 1H), 8.22-8.16 (m, 2H), 8.09 (d, 1H), 7.86 (d, 3H), 7.70-7.68 (m, 2H), 7.47 (d, 1H), 6.90 (dd, J = 2.2, 4.8, 2H), 6.34 (t, J = 5.2, 1H), 4.41-4.27 (m, 2H), 3.81 (s, 3H), 3.69 (d, 2H), 2.62-2.50 (m, 8H), 2.40-2.26 (s, 3H).<br>HPLC: 71%; MS: 615.2 (M + 1) |
| OR0816 | 4-[(4-methyl-piperazin-1-ylmethyl)]-3-trifluoromethyl-benzoic acid | 5-{2-Fluoro-5-[4-(4-methyl-piperazin-1-ylmethyl)-3-trifluoromethyl-benzoyl-amino]-benzylamino}-1H-pyrrolo[2,3-b]pyridine-2-carboxylic acid methyl ester<br><br>Yield: 26%<br>$^1$H NMR (300 MHz, DMSO) δ 12.06 (s, 1H), 10.45 (s, 1H), 8.25-8.12 (m, 2H), 8.12-8.03 (m, 1H), 7.95-7.84 (m, 1H), 7.84-7.67 (m, 2H), 7.23 (t, J = 9.2 Hz, 1H), 7.06-6.95 (m, 1H), 6.95-6.84 (m, 1H), 6.30-6.15 (m, 1H), 4.42-4.28 (m, 2H), 3.82 (s, 3H), 3.66 (s, 2H), 2.48-2.30 (m, 8H), 2.21 (s, 3H).<br>HPLC: 98%; MS: 599 (M+l) |
| OR0622 | 4-[(4-methyl-piperazin-1-ylmethyl)]-3-trifluoromethyl-benzoic acid | 5-{4-Methyl-3-[4-(4-methyl-piperazin-1-ylmethyl)-3-trifluoromethyl-benzoyl-amino]-benzylamino}-1H-pyrrolo[2,3-b]pyridine-2-carboxylic acid methyl ester<br><br>Yield: 8%<br>$^1$H NMR (600 MHz, DMSO) δ (ppm) 11.99 (s, 1H), 10.10 (s, 1H), 8.25 (s, 1H), 8.22 (d, J = 8.1, 2H), 8.15 (s, 1H), 8.05 (d, J = 2.7, 1H), 7.95 (d, J = 8.1, 1H), 7.90 (d, J = 8.1, 1H), 7.35 (s, 1H), 7.23 (s, 1H), 6.99 (d, J = 2.6, 1H), 6.86 (s, J = 1.7, 1H), 6.20 (t, J = 5.9, 1H), 4.29 (d, J = 5.9, 2H), 3.67 (m, 3H), 2.45-2.30 (m, 10H), 2.22-2.11 (m, 6H)<br>HPLC: 78%; MS: 595.2 (M + 1) |

TABLE 5-continued

Compounds obtained by example D

| Example No. | Used reagents | Synthesized inhibitors (mass and analytical data) |
|---|---|---|
| OR1067 | 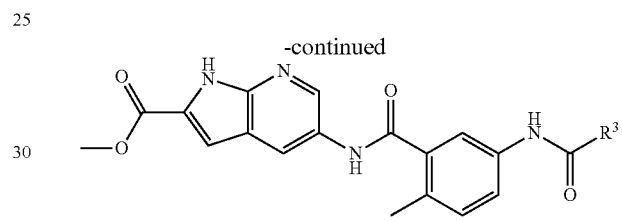 | 5-{3-[4-(4-methyl-piperazin-1-ylmethyl)-3-trifluoromethyl-benzoylamino]-benzylamino}-1H-pyrrolo[2,3-b]pyridine-2-carboxylic acid methyl ester<br><br>Yield: 41%<br>¹H NMR (600 MHz, DMSO) δ (ppm) 12.07 (s, 1H), 10.46 (s, 1H), 8.25 (s, 1H), 8.23 (d, J = 8.2, 1H), 8.10 (d, J = 2.5, 1H), 7.93 (d, J = 7.7, 1H), 7.82 (s, 1H), 7.70 (d, J = 8.2, 1H), 7.35 (t, J = 7.7, 1H), 7.19 (d, J = 7.7, 1H), 7.00 (d, J = 2.5, 1H), 6.90 (s 1H), 6.29 (t, J = 5.7, 1H), 4.33 (d, J = 5.7, 2H), 3.84 (s, 3H), 3.69 (s, 2H), 2.51-2.27 (m, 8H), 2.19 (s, 3H)<br>HPLC: 94%; MS: 581 (M + 1) |

Example E

Synthesis of 5-{2-methyl-5-[3-amido]-benzoylamino}-1H-pyrrolo[2,3-b]pyridine-2-carboxylic methyl esters in 3 stages starting from the commercial reagent from the company OriBase Pharma Scheme 22 represents a general method of synthesis of 5-{2-methyl-5-[3-amido]-benzoylamino}-1H-pyrrolo[2,3-b]pyridine-2-carboxylic methyl ester.

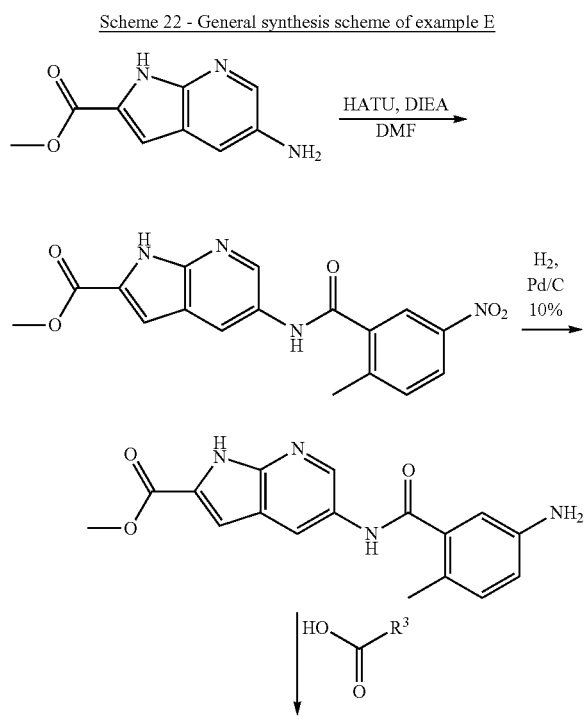

Scheme 22 - General synthesis scheme of example E

Step 1: General protocol for the preparation of 5-(2-methyl-5-nitro-benzoylamino)-1H-pyrrolo[2,3-b]pyridine-2-carboxylic acid methyl ester 5-Amino-1H-pyrrolo[2,3-b]pyridine-2-carboxylic acid methyl ester (5.74 g, 30 mmol), 2-methyl-5-nitrobenzylic acid (5.44 g, 30 mmol), HATU (11.42 g, 30 mmol), DIEA (26 mL, 150 mmol) are dissolved in anhydrous DMF (300 mL) and stirred 48 h at RT. DMF is evaporated, NaHCO₃(aq) is added, a precipitate occurred and filtered, washed with water and petroleum ether/Et₂O. The expected product is obtained (9.94 g, 28 mmol). Yield=93%. ¹H NMR (300 MHz, DMSO-d6) δ 8.53 (s, 2H), 8.37 (d, J=2.5, 1H), 8.26 (dd, J=2.5, 8.4, 1H), 7.63 (d, J=8.5, 1H), 7.16 (s, 1H), 3.86 (s, 3H), 3.17 (s, 1H), 2.54 (s, 3H). ESI-MS: m/z 355 ([M+H]⁺). HPLC purity: 95%.

Step 2: General protocol for the preparation of 5-(5-amino-2-methyl-benzoylamino)-1H-pyrrolo[2,3-b]pyridine-2-carboxylic acid methyl ester 5-(2-Methyl-5-nitro-benzylamino)-1H-pyrrolo[2,3-b]pyridine-2-carboxylic acid methyl ester (9.8 g, 27.7 mmol), methanol (300 mL) and palladium 10% on charcoal (0.95 g, 10% w/w) are put in an autoclave filled with 30 bar of dihydrogen and stirred for 24 h. Mixture is filtered on celite and washed with methanol. Solvent is evaporated to obtain a brown solid (7.35 g, 22.7 mmoles). Yield=81%. ¹H NMR (300 MHz, DMSO-d6) δ 10.29 (s, 1H), 8.55 (s, 2H), 7.15 (s, 1H), 6.94 (d, J=8.2, 1H), 6.71 (d, J=2.3, 1H), 6.60 (m, 1H), 5.08 (s, 2H), 3.86 (s, 3H), 2.21 (s, 3H). ESI-MS: m/z 325 ([M+H]⁺). HPLC purity: 95%.

Step 3: General protocol for the preparation of 5-{2-methyl-5-[3-amido]-benzoylamino}-1H-pyrrolo[2,3-b]pyridine-2-carboxylic methyl esters Acid derivative is dissolved in anhydrous DMF (0.06 mol/L) with DIEA (5 eq) and HATU (2 eq). After 15 min, 5-{2-methyl-5-[3-amino]-benzoylamino}-1H-pyrrolo[2,3-b]pyridine-2-carboxylic methyl ester is slowly added and mixture is stirred for 12 h at RT. DMF is evaporated and NaHCO₃(aq) is added. Product is extracted with EtOAc, dried, filtered and evaporated to obtain a dark mixture. After purification by washing with MeOH or EtOAc or by silica column, expected product is obtained as a slightly yellow or orange powder. Table 6 shows the compounds synthesized according to the synthesis Scheme 20 described above.

Example F

Synthesis of 5-{2-methyl-5-[5-thiobenzoylamino]-benzylamino}1H-pyrrolo[2,3-b]pyridine-2-carboxylic acid methyl ester General method to synthesize 5-{2-methyl-5-[5-thiobenzoylamino]-benzylamino}-1H-pyrrolo[2,3-b]pyridine-2-carboxylic acid methyl ester is represented by Scheme 23.

Scheme 23 - General synthesis scheme of example F

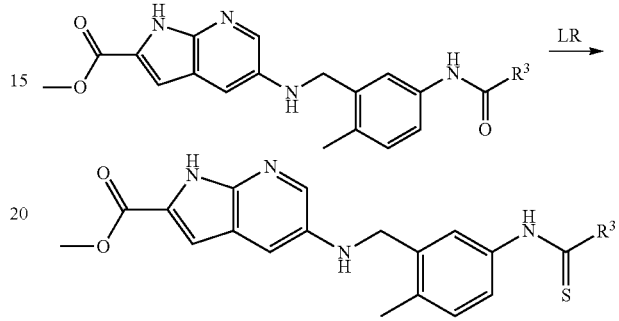

TABLE 6

Compounds obtained by example E

| Example No. | Used reagents | Synthesized inhibitors (mass and analytical data) |
|---|---|---|
| OR0745 | (structure: 5-trifluoromethyl-pyridine-3-carboxylic acid) | 5-{2-Methyl-5-[(5-trifluoromethyl-pyridine-3-carbonyl)-amino]-benzoylamino}-1H-pyrrolo[2,3-b]pyridine-2-carboxylic acid methyl ester<br><br>Yield: 36%<br>¹H NMR (300 MHz, DMSO) δ (ppm) 12.50 (s, 1H), 10.73 (s, 1H), 10.54 (s, 1H), 9.39 (s, 1H), 9.20 (s, 1H), 8.71 (s, 1H), 8.60 (s, 2H), 7.90 (s, 1H), 7.85 (d, J = 8.2, 1H), 7.36 (d, J = 8.2, 1H), 7.21 (d, J = 1.7, 1H), 3.88 (s, 3H), 2.40 (s, 3H).<br>HPLC: 97%; MS: 498.2 (M + 1) |
| OR0744 | (structure: 4-(4-methyl-piperazin-1-ylmethyl)-3-trifluoromethyl-benzoic acid) | 5-{2-Methyl-5-[4-(4-methyl-piperazin-1-ylmethyl)-3-trifluoromethyl-benzoyl-amino]-benzoylamino}-1H-pyrrolo[2,3-b]pyridine-2-carboxylic acid methyl ester<br><br>Yield: 30%<br>¹H NMR (300 MHz, DMSO) δ (ppm) 12.50 (bs, 1H), 10.53 (d, 2H), 8.60 (s, 2H), 8.33-8.18 (m, 2H), 8.04-7.78 (m, 3H), 7.33 (d, J = 7.9 1H), 7.21 (s, 1H), 3.88 (s, 3H), 3.70 (s, 2H), 2.55-2.45 (m, 8H) 2.39 (s, 3H), 2.30 (s, 3H).<br>HPLC: 99%; MS: 609.3 (M + 1) |

General Procedure for the Synthesis of Thioamide Starting from Amide Derivatives:

A suspension of 5-{2-methyl-5-[5-benzoylamino]-benzylamino}1H-pyrrolo[2,3-b]pyridine-2-carboxylic acid methyl ester (100 mg) and Lawesson's reagent ("LR" in Scheme 23) (1.8 eq) in 5 mL of chlorobenzene was heated at 130° C. for 2 hours. The solvent is evaporated and the residue is purified by silica gel chromatography (water+1% TFA/acetonitrile+1% TFA). After evaporation of the solvent, the residue is dissolved in water, basified to pH 7-8 by $NaHCO_3$ and extract by AcOEt. The organic layer is then dried over $Na_2SO_4$ and the solvent removed to give a yellow solid.

TABLE 7

Compounds obtained by example F

| Example No. | Synthesized inhibitors (mass and analytical data) |
|---|---|
| OR0643 | 5-{2-Methyl-5-[5-(4-methyl-imidazol-1-yl)-3-trifluoromethyl-thiobenzoyl-amino]-benzylamino}-1H-pyrrolo[2,3-b]pyridine-2-carboxylic acid methyl ester<br><br>Yield: 19%<br>$^1$H NMR (300 MHz, DMSO) δ 12.04 (s, 1H), 11.98 (s, 1H), 8.56 (bs, 1H), 8.25 (s, 1H), 8.16 (s, 1H), 8.10 (s, 1H), 8.03 (s, 1H), 7.82-7.64 (m, 3H), 7.31 (d, J = 8.1, 1H), 6.99 (d, J = 2.4, 1H), 6.89 (d, J = 1.9, 1H), 6.16 (bs, 1H), 4.30 (s, 2H), 3.83 (s, 3H), 2.40 (s, 3H), 2.20 (s, 3H).<br>HPLC: 96%; MS: 579 (M + 1) |
| OR0626 | 5-{2-Methyl-5-[4-(4-methyl-piperazin-1-ylmethyl)-3-trifluoromethyl-thio-benzoylamino]-benzylamino}-1H-pyrrolo[2,3-b]pyridine-2-carboxylic acid methyl ester<br><br>Yield: 22%<br>$^1$H NMR (300 MHz, DMSO) δ (ppm) 12.02 (s, 1H), 11.84 (s, 1H), 8.08 (s, 1H), 8.05 (m, 2H), 7.83-7.76 (m, 1H), 7.68 (m, 2H), 7.28 (d, J = 8.0, 1H), 7.00 (s, 1H), 6.89 (s, 1H), 6.48-5.57 (m, 1H), 4.27 (s, 2H), 3.82 (s, 3H), 3.64 (s, 2H), 2.47-2.40 (m, 4H), 2.37 (s, 3H), 2.34-2.17 (m, 4H).<br>HPLC: 96%; MS: 611 (M + 1) |
| OR0815 | 5-{5-[4-(3-Dimethylamino-pyrrolidin-1-ylmethyl)-3-trifluoromethyl-thiobenzoyl-amino]-2-methyl-benzylamino}-1H-pyrrolo[2,3-b]pyridine-2-carboxylic acid methyl ester<br><br>Yield: 32%<br>$^1$H NMR (300 MHz, DMSO) δ (ppm) 12.12 (s, 1H), 11.96 (s, 1H), 8.20-8.11 (m, 3H), 8.03 (s, 1H), 7.86 (d, J = 7.7, 1H), 7.78-7.70 (m, 2H), 7.35 (d, J = 7.7, 1H), 7.08 (d, J = 2.0, 1H), 6.96 (d, J = 2.0, 1H), 4.35 (s, 3H), 3.50-3.41 (m, 3H), 2.97 (s, 2H), 2.83 (s, 6H), 2.45 (s, 1H), 2.07 (s, 2H), 1.31-1.17 (m, 6H).<br>HPLC: 94%; MS: 571 (M + 1) |

Example G

Synthesis of 5-{2-methyl-5-[4-(4-methyl-piperazin-1-ylmethyl)-3-trifluoromethyl-benzoylamino]-benzylamino}1H-pyrrolo[2,3-b]pyridine-2-carboxylic acid propyl ester General method to synthesize 5-{2-methyl-5-[4-(4-methyl-piperazin-1-ylmethyl)-3-trifluoromethyl-benzoylamino]-benzylamino}1H-pyrrolo[2,3-b]pyridine-2-carboxylic acid propyl or ethyl ester is represented by Scheme 24 in 2 steps.

Scheme 24 - General synthesis scheme of example G

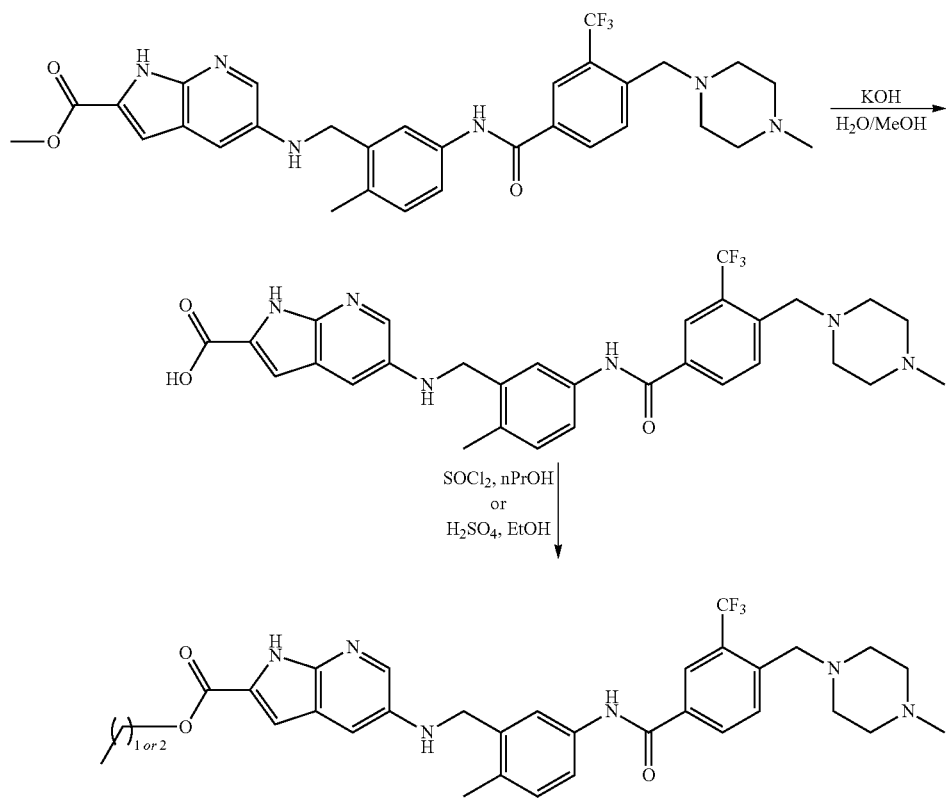

Step 1: Synthesis of 5-{2-methyl-5-[4-(4-methyl-piperazin-1-ylmethyl)-3-trifluoromethyl-benzoylamino]-benzylamino}1H-pyrrolo[2,3-b]pyridine-2-carboxylic acid (OR0623)

A suspension of 5-{2-methyl-5-[4-(4-methyl-piperazin-1-ylmethyl)-3-trifluoromethyl-benzoylamino]-benzylamino}1H-pyrrolo[2,3-b]pyridine-2-carboxylic acid methyl ester (580 mg) and potassium hydroxide (5 eq) in water (3 mL) and methanol (3 mL) was heated at 65° C. for 18 hours. Methanol was evaporated and the pH neutralized to pH 7 by HCl 6N. After evaporation of the solvent, the crude residue was purified by silica gel chromatography (water/acetonitrile) to give a brown solid.

Yield: 54% (305 mg)

$^1$H NMR (300 MHz, DMSO) δ 11.24 (s, 1H), 10.39 (s, 1H), 8.22-8.15 (m, 2H), 7.94 (d, J=2.5, 1H), 7.87 (d, J=8.0, 1H), 7.71-7.64 (m, 2H), 7.18 (d, J=8.8, 1H), 6.95 (d, J=2.3, 1H), 6.54 (s, 1H), 5.94-5.73 (m, 1H), 4.21 (s, 2H), 3.65 (s, 2H), 2.46-2.24 (m, 11H), 2.16 (s, 3H).

HPLC: 100%; MS: 581 (M+1)

Step 2 (Option 1): Synthesis of 5-{2-methyl-5-[4-(4-methyl-piperazin-1-ylmethyl)-3-trifluoromethyl-benzoylamino]-benzylamino}-1H-pyrrolo[2,3-b]pyridine-2-carboxylic acid propyl ester (OR0697)

To a suspension of 5-{2-methyl-5-[4-(4-methyl-piperazin-1-ylmethyl)-3-trifluoromethyl-benzoylamino]-benzylamino}-1H-pyrrolo[2,3-b]pyridine-2-carboxylic acid (80 mg) in 3.5 mL of propanol, was added thionyl chloride (3 eq). The mixture was heated at 100° C. overnight. After evaporation of the solvent, the crude residue was purified by silica gel chromatography (acetonitrile+1% TFA). After evaporation of the solvent, the residue was dissolved in water, basified until pH 9 by NaHCO$_3$ and extracted by AcOEt. The organic layer was then dried over Na$_2$SO$_4$ and the solvent removed to give a brown solid.

Yield: 44% (32 mg)

$^1$H NMR (400 MHz, DMSO) δ(ppm) 11.98 (s, 1H), 10.33 (s, 1H), 8.20 (s, 1H), 8.20 (s, 1H), 8.15 (d, J=8.1, 1H), 8.10 (d, J=2.5, 1H), 7.88 (d, J=8.1, 1H), 7.71-7.63 (m, 2H), 7.01 (d, J=2.5, 1H), 6.90 (d, J=2.1, 1H), 6.03 (t, J=5.4, 1H), 4.26-4.18 (m, 4H), 3.66 (s, 2H), 2.48-2.38 (m, 8H), 2.34 (s, 3H), 2.18 (s, 3H), 0.97 (t, 3H)

HPLC: 96%; MS: 623.3 (M+1)

Step 2 (Option 2): Synthesis of 5-{2-methyl-5-[4-(4-methyl-piperazin-1-ylmethyl)-3-trifluoromethyl-benzoylamino]-benzylamino}-1H-pyrrolo[2,3-b]pyridine-2-carboxylic acid ethyl ester (OR1082)

To a suspension of 5-{2-methyl-5-[4-(4-methyl-piperazin-1-ylmethyl)-3-trifluoromethyl-benzoylamino]-benzylamino}-1H-pyrrolo[2,3-b]pyridine-2-carboxylic acid (90 mg) in 4 mL of ethanol was added sulfuric acid 95% (0.5 eq). The mixture was heated at refluxing for 6 h. After evaporation of the solvent, the crude residue was purified by silica gel chromatography (acetonitrile+1% TFA). After evaporation of the solvent, the residue was dissolved in water, basified until pH 9 by NaHCO$_3$ and extracted by AcOEt. The organic layer was then dried over Na$_2$SO$_4$ and the solvent removed to give a yellow solid.

Yield: 37% (35 mg)

$^1$H NMR (400 MHz, DMSO) δ(ppm) $^1$H NMR (400 MHz, DMSO) δ 11.99 (s, 1H), 10.34 (s, 1H), 8.20-8.14 (m, 2H), 8.09 (d, J=2.6, 1H), 7.87 (d, J=8.1, 1H), 7.66 (d, J=9.5, 2H), 7.19 (d, J=8.1, 1H), 6.99 (d, J=2.5, 1H), 6.88 (d, J=2.0, 1H), 6.05 (t, J=5.4, 1H), 4.29 (q, J=7.1, 2H), 4.23 (d, J=5.4, 2H), 3.65 (s, 2H), 2.46-2.33 (m, 3H), 2.30 (s, 3H), 2.15 (s, 3H), 1.30 (t, J=7.1, 3H).

HPLC: 96%; MS: 609 (M+1)

Example H

Synthesis of 5-[3-(benzoylamino-methyl)-benzylamino]-1H-pyrrolo[2,3-b]pyridine-2-carboxylic acid methyl ester and 5-[3-(thiobenzoylamino-methyl)-benzylamino]-1H-pyrrolo[2,3-b]pyridine-2-carboxylic acid methyl ester General method to synthesize 5-[3-(benzoylamino-methyl)-benzylamino]-1H-pyrrolo[2,3-b]pyridine-2-carboxylic acid methyl ester and 5-[3-(thiobenzoylamino-methyl)-benzylamino]-1H-pyrrolo[2,3-b]pyridine-2-carboxylic acid methyl ester is represented by Scheme 25 in 3 or 4 steps.

Step 1. General protocol for the preparation of 3-(benzoylamino-methyl)-benzoic acid methyl ester 3-Aminomethyl-benzoic acid methyl ester hydrochloride (1 eq), HOBt (1.2 eq), DIEA (1.2 eq) and EDCl.HCl (1.2 eq) were dissolved in dry DMF (0.17 M) and stirred for 30 min at RT under argon. The amine derivative (1 eq) was added and the mixture was stirred at RT overnight. DMF was evaporated and saturated NaHCO$_3$ solution was added. Product was extracted with EtOAc, dried over Na$_2$SO$_4$, filtered and evaporated. The crude was purified on silicagel chromatography to give the expected product after evaporation of solvents.

3-[(3-Trifluoromethyl-benzoylamino)-methyl]-benzoic acid methyl ester white powder. Yield: 45% (528 mg). HPLC: 93%. MS: 338 (M+1).

3-{[4-(4-Methyl-piperazin-1-ylmethyl)-3-trifluoromethyl-benzoylamino]-methyl}-benzoic acid methyl ester black powder. Yield: quantitative (1.55 g). HPLC: 91%. MS: 450 (M+1).

Step 2. Synthesis of 3-[(3-Trifluoromethyl-thiobenzoylamino)-methyl]-benzoic acid methyl ester A suspension of 3-[(3-trifluoromethyl-benzoylamino)-methyl]-benzoic acid methyl ester (528 mg) and Lawesson's reagent ("LR" in Scheme 23) (1.8 eq) in 26 mL of toluene was heated at 110° C. for 3 hours. The solvent was evaporated and saturated NaHCO$_3$ solution was added to the crude. Product was extracted with EtOAc, dried over Na$_2$SO$_4$, filtered and evaporated. The crude oil was purified on silicagel chromatography to give the expected product after evaporation of solvents.

Scheme 25 - General synthesis scheme of example H

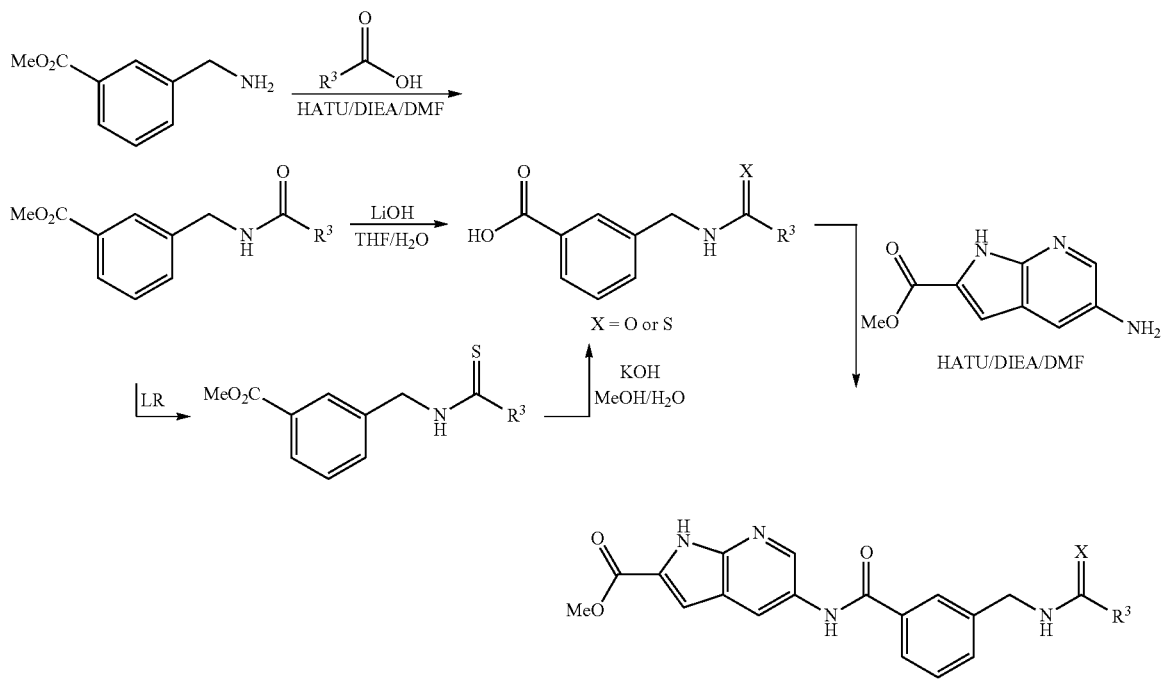

yellow oil. Yield: 94% (518 mg). HPLC: >99%. MS: 354 (M+1).

Step 3. General Protocol for the Saponification of Methyl Ester

The methyl ester (1 eq) was suspended in a mixture of solvents (THF/Water or MeOH/Water_1/1). Alcaline base (LiOH or KOH, 3 eq) was added and the mixture was heated at reflux until complete reaction (TLC control). Organic solvent was evaporated, the mixture was neutralized and the product was extracted with organic solvents.

3-[(3-Trifluoromethyl-thiobenzoylamino)-methyl]-benzoic acid yellow powder. Yield: 88% (438 mg). HPLC: 98%. MS: 340 (M+1).

3-{[4-(4-Methyl-piperazin-1-ylmethyl)-3-trifluoromethyl-benzoylamino]-methyl}-benzoic acid Yield: 54% (792 mg). HPLC: 93%. MS: 436 (M+1).

Step 4. General Protocol for Peptide Like Coupling Reaction

Acid derivative and HATU (2 eq) were dissolved in anhydrous DMF (0.1-0.2 mol/L). After 30 min, 5-Amino-1H-pyrrolo[2,3-b]pyridine-2-carboxylic acid methyl ester (1 eq) and DIEA (3-4 eq) were added and mixture was stirred overnight at RT. DMF is evaporated and saturated NaHCO$_3$ solution was added. Product was extracted with EtOAc, dried over Na2SO4, filtered and evaporated. The crude was purified on reverse phase (H2O 1% TFA/MeCN 1% TFA 100/0, 0/100). MeCN was evaporated. The product was suspended in H$_2$O and basified with saturated NaHCO$_3$ solution until pH=8-9. The aqueous layer was extracted three times with AcOEt. The organic layer was evaporated to give the final compound.

TABLE 8

Compounds obtained by example H

| Example No. | Synthesized inhibitors (mass and analytical data) |
|---|---|
| OR1011 | 5-{3-[(3-Trifluoromethyl-thiobenzoylamino)-methyl]-benzoylamino}-1H-pyrrolo[2,3-b]pyridine-2-carboxylic acid methyl ester 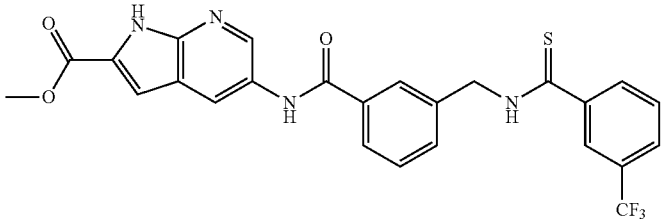 Yield: 18% $^1$H NMR (300 MHz, DMSO) δ (ppm) 12.46 (s, 1H), 11.06 (s, 1H), 10.41 (s, 1H), 8.65 (s, 1H), 8.53 (s, 1H), 8.11 (m, 2H), 8.00 (s, 1H), 7.93 (d, J = 7.7, 1H), 7.88 (d, J = 8.1, 1H), 7.71 (t, J = 7.6, 1H), 7.62 (d, J = 7.6, 1H), 7.54 (t, J = 7.6, 1H), 7.20 (d, J = 2.0, 1H), 5.08 (d, J = 5.7, 2H), 3.89 (s, 3H). HPLC: 96%; MS: 499 (M + 1) |
| OR0983 | 5-(3-{[4-(4-Methyl-piperazin-1-ylmethyl)-3-trifluoromethyl-benzoylamino]-methyl}-benzoylamino)-1H-pyrrolo[2,3-b]pyridine-2-carboxylic acid methyl ester 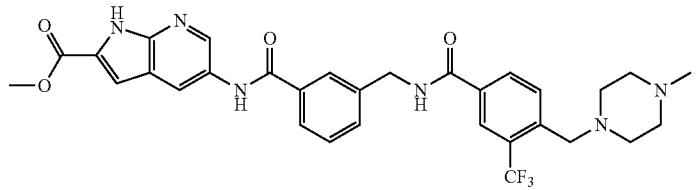 Yield: 28% $^1$H NMR (300 MHz, DMSO) δ 12.20 (s, 1H), 10.46 (s, 1H), 9.40 (t, J = 5.2, 1H), 8.63 (d, J = 2.3, 1H), 8.50 (d, J = 2.3, 1H), 8.23 (s, 1H), 8.19 (d, J = 8.2, 1H), 7.96 (s, 1H), 7.92 (d, J = 7.8, 1H), 7.89 (d, J = 7.8, 1H), 7.55 (d, J = 8.2, 1H), 7.51 (t, J = 7.8, 1H), 7.16 (s, 1H), 4.60 (d, J = 5.2, 2H), 3.87 (s, 3H), 3.65 (s, 2H), 2.45-2.25 (m, 8H), 2.15 (s, 3H). HPLC: >99%; MS: 609 (M + 1) |

Example I

Synthesis of 5-{3-(phenylcarbamoyl)-benzylamino}-1H-pyrrolo[2,3-b]pyridine-2-carboxylic acid methyl ester in 3 stages starting from 3-cyano-benzoic acid Scheme 26 represents a general method of synthesis of 5-{3-(phenylcarbamoyl)-benzylamino}-1H-pyrrolo[2,3-b]pyridine-2-carboxylic acid methyl ester Scheme 26 - General synthesis scheme of example I

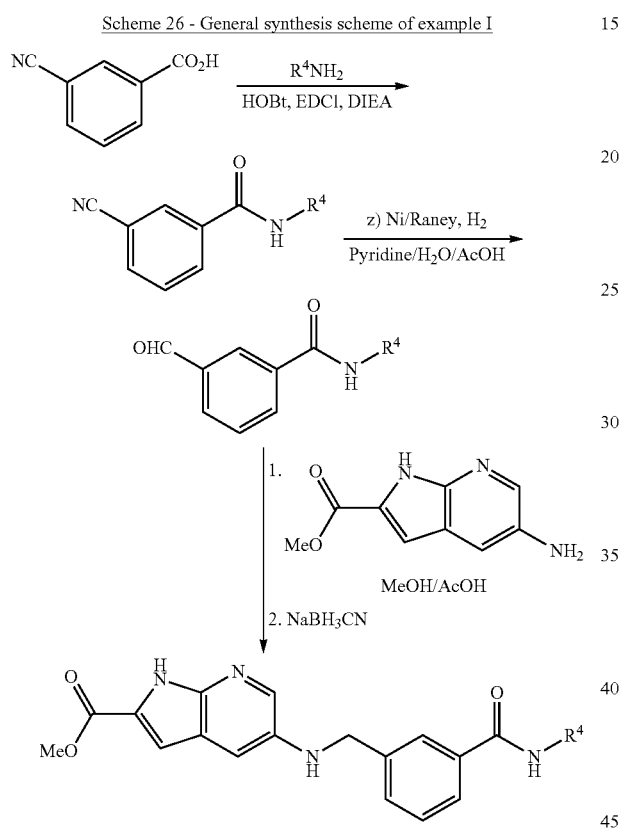

Step 1: General protocol for the preparation of 3-cyano-benzamide compounds

3-Cyano-benzoic acid (1.2 eq), the amine derivative (1 eq), HOBt (1.2 eq), DIEA (1.2 eq) and EDCI.HCl (1.2 eq) were dissolved in dry DMF (0.15 M), under argon. The mixture was stirred at room temperature overnight. DMF is evaporated and saturated NaHCO$_3$ solution was added. Product was extracted with EtOAc, dried over Na$_2$SO$_4$, filtered and evaporated. The crude was purified on reverse phase (H2O 1% TFA/MeCN 1% TFA 100/0, 0/100). MeCN was evaporated. The product was suspended in H$_2$O and basified with saturated NaHCO$_3$ solution until pH=8-9. The aqueous layer was extracted three times with AcOEt. The organic layer was evaporated to give the final compound.

3-Cyano-N-(3-trifluoromethyl-benzyl)-benzamide

White powder. Yield: 76% (334 mg). HPLC: >99%. MS: 305 (M+1).

3-Cyano-N-pyridin-3-yl-benzamide

Brown powder. Yield: 47% (563 mg). HPLC: >99%. MS: 224 (M+1).

3-Cyano-N-[4-(4-methyl-piperazin-1-ylmethyl)-3-trifluoromethyl-phenyl]-benzamide Yellow oil. Yield: 22% (52 mg). HPLC: 92%. MS: 403 (M+1).

Step 2: General protocol for the preparation of 3-formyl-benzamide compounds Under argon, 3-cyano-benzamide intermediate (1 eq) was dissolved in a mixture of pyridine/water/acetic acid (2/1/1; 0.01M). Ni Raney in water (~0.03 vol) was added and the mixture was stirred at room temperature overnight under hydrogen at atmospheric pressure. Then, the mixture was filtered over celite bed and washed with methanol. Solvents were evaporated. Saturated NaHCO$_3$ solution was added. Product was extracted with EtOAc, dried over Na$_2$SO$_4$, filtered and evaporated to give the final compound.

3-Formyl-N-(3-trifluoromethyl-benzyl)-benzamide

Yellow oil. Yield: 79% (40 mg). HPLC: 89%. MS: 308 (M+1).

3-Formyl-N-pyridin-3-yl-benzamide

Yellow oil. Yield: 66% (166 mg). HPLC: >99%. MS: 227 (M+1).

3-Formyl-N-[4-(4-methyl-piperazin-1-ylmethyl)-3-trifluoromethyl-phenyl]-benzamide Yellow oil. Yield: 57% (30 mg). HPLC: 75%. MS: 406 (M+1).

Step 3: General protocol for the preparation of 5-{3-(phenylcarbamoyl)-benzylamino}-1H-pyrrolo[2,3-b]pyridine-2-carboxylic acid methyl ester 5-amino-1H-pyrrolo[2,3-b]pyridine-2-carboxylic acid methyl ester (1 eq) and 3-formyl-benzamide compound (1.1 eq) were stirred in a mixture of MeOH/AcOH (10/1; 0.06M) for 2 h. Then NaBH$_3$CN (1.2 eq) was slowly added and the mixture was stirred under argon at RT overnight. The reaction was quenched by addition of saturated NaHCO$_3$ solution until neutrality. MeOH and acetic acid were evaporated. The crude was filtered and washed with water and Et2O before being purified on reverse phase (H$_2$O 1% TFA/MeCN 1% TFA 100/0, 0/100). MeCN was evaporated. The product was suspended in H$_2$O and basified with saturated NaHCO$_3$ solution until pH=8-9. The aqueous layer was extracted three times with AcOEt. The organic layer was dried over Na2SO4, filtered and concentrated to give the expected product.

TABLE 9

Compounds obtained by example I

| Example No. | Used reagents | Synthesized inhibitors (mass and analytical data) |
|---|---|---|
| OR0635 | 4-(4-methylpiperazin-1-ylmethyl)-3-trifluoromethyl-aniline | 5-{3-[4-(4-Methyl-piperazin-1-ylmethyl)-3-trifluoromethyl-phenylcarbamoyl]-benzylamino}-1H-pyrrolo[2,3-b]pyridine-2-carboxylic acid methyl ester<br><br>Yield: 10%<br>$^1$H NMR (400 MHz, DMSO) δ (ppm) 12.07 (s, 1H), 10.53 (s, 1H), 8.23 (d, J = 2.3, 1H), 8.12 (d, J = 2.3, 1H), 8.10-8.03 (m, 2H), 7.89 (d, J = 8.2, 1H), 7.74 (d, J = 8.2, 1H), 7.67 (d, J = 7.6, 1H), 7.54 (t, J = 7.6, 1H), 7.07 (d, J = 2.4, 1H), 6.92 (d, J = 2.4, 1H), 6.32 (t, J = 6.0, 1H), 4.44 (d, J = 6.0, 2H), 3.86 (s, 3H), 3.61 (s, 2H), 2.49-2.30 (m, 8H), 2.23 (s, 3H).<br>HPLC: 95%; MS: 581 (M + 1) |
| OR0916 | 3-aminopyridine | 5-[3-(Pyridin-3-ylcarbamoyl)-benzylamino]-1H-pyrrolo[2,3-b]pyridine-2-carboxylic acid methyl ester<br><br>Yield: quantitative<br>$^1$H NMR (300 MHz, DMSO) δ (ppm) δ 12.04 (s, 1H), 10.44 (s, 1H), 8.91 (s, 1H), 8.31 (d, J = 4.8, 1H), 8.17 (d, J = 7.9, 1H), 8.08 (d, J = 2.2, 1H), 8.01 (s, 1H), 7.86 (d, J = 7.3, 1H), 7.64 (d, J = 7.3, 1H), 7.50 (t, J = 7.3, 1H), 7.39 (dd, J = 4.8, 7.9, 1H), 7.05-7.00 (m, 1H), 6.88 (d, J = 1.8, 1H), 6.30 (t, J = 5.3, 1H), 4.40 (d, J = 5.3, 2H), 3.82 (s, 3H).<br>HPLC: 97%; MS: 402 (M + 1) |
| OR1004 | 3-(trifluoromethyl)benzylamine | 5-[3-(3-Trifluoromethyl-benzylcarbamoyl)-benzylamino]-1H-pyrrolo[2,3-b]pyridine-2-carboxylic acid methyl ester<br><br>Yield: 30%<br>$^1$H NMR (300 MHz, DMSO) δ (ppm) 12.06 (s, 1H), 9.16 (t, J = 6.0, 1H), 8.10 (d, J = 2.6, 1H), 7.98 (s, 1H), 7.80 (d, J = 7.7, 1H), 7.70 (s, 1H), 7.66-7.52 (m, 4H), 7.47 (t, J = 7.7, 1H), 7.04 (d, J = 2.1, 1H), 6.90 (d, J = 2.1, 1H), 6.28 (t, J = 5.8, 1H), 4.58 (d, J = 5.8, 2H), 4.38 (d, J = 5.8, 2H), 3.86 (s, 3H).<br>HPLC: 92%; MS: 483 (M + 1) |

BIOLOGICAL TESTS

Material and Methods:

1) In Vitro Kinase Assays (Tables B1 to B13)

The inhibitory activity of the compounds on several kinases including BRAF, EGFR (ErbB1), EGFR (ErbB1) T790M L858R, FGFR2, KDR (VEGFR2), PDGFRA (PDGFR alpha), SRC and other was evaluated by Invitrogen using the Z'-LYTE® technology. Briefly, the Z'-LYTE® biochemical assay employs a fluorescence-based, coupled-enzyme format and is based on the differential sensitivity of phosphorylated and non-phosphorylated peptides to proteolytic cleavage. The peptide substrate is labeled with two fluorophores—one at each end—that make up a FRET pair. A ratiometric method, which calculates the ratio (the Emission Ratio) of donor emission to acceptor emission after excitation of the donor fluorophore at 400 nm, is used to quantitate reaction progress.

The compounds are screened in 1% DMSO (final) in the well. For 10 point titrations, 3-fold serial dilutions are conducted from the starting concentration. All Peptide/Kinase Mixtures are diluted to a 2× working concentration in the appropriate Kinase Buffer. All ATP Solutions are diluted to a 4× working concentration in Kinase Buffer (50 mM HEPES pH 7.5, 0.01% BRIJ-35, 10 mM MgCl2, 1 mM EGTA). ATP Km apparent is previously determined using a Z'-LYTE® assay.

Each compound was incubated at a concentration of 100 nM (excepted to test the activity against ABL and ABL T315I for which the compounds were incubated at a concentration of 10 µM) and the tables B1 to B12 summarize the results obtained showing the inhibitory power of a compound. The inhibitory activity of OR0512 was also investigated using the same assays and the kinases for which activity was inhibited at more than 50% at the concentration of 100 nM of OR0512 are listed in the table B13.

2) In Vitro Cell Proliferation Assays (Table B14 to B33)

Cancer cell lines ($5\times10^3$ cells per well) or HUVEC ($1\times10^4$ cells per well) or HRMEC ($1\times10^4$ cells per well) were distributed in 96-well plates and incubating in duplicate with escalating concentrations (10 nM to 3 µM) of compounds for 72 hr. Cell proliferation was measured using MTT (3 [4,5-dimethylthiazol-2-yl]-2,5-diphenyltetrazolium bromide). The EC50 values were calculated from sigmoidal dose-response curves utilizing Prism 5.0 from Graph-Pad Software (GraphPad Software, La Jolla, Calif., USA), with values normalized to those of DMSO-treated control wells (0%) and 1% SDS control wells (100%).

3) In Vivo Studies (Table B34)

Several xenograft mouse models were prepared:
1) imatinib-resistant leukemia by subcutaneously implanting Ba/F3 T315I cells ($1\times10^8$ cell/mL in sterile PBS), into the right flank of athymic nude male mice (HSD, 6-7 weeks old). When the tumor volume reached approximately 50 mm³, mice were assigned randomly to either vehicle alone or OR0512 treatment groups (five mice per group). Mice were treated with either vehicle (DMSO) or OR0512 (40 mg/kg q.d.; per os for 11 consecutive days).
2) human pancreatic adenocarcinoma model by subcutaneously implanting BxPC-3 cells ($1\times10^7$ cell/mL in sterile PBS), into the right flank of athymic nude male mice (HSD, 6-7 weeks old). When the tumor volume reached approximately 100 mm³, mice were assigned randomly to either vehicle alone or OR0512 treatment groups (five mice per group). Mice were treated with either vehicle (DMSO) or OR0512 (20 mg/kg q.d.; per os for 32 consecutive days).
3) human hepatocellular carcinoma model by subcutaneously implanting HepG2 cells ($1\times10^7$ cell/mL in sterile PBS), into the right flank of athymic nude male mice (HSD, 6-7 weeks old). When the tumor volume reached approximately 100 mm³, mice were assigned randomly to either vehicle alone or OR0512 treatment groups (five mice per group). Mice were treated with either vehicle (DMSO) or OR0512 (20 mg/kg q.d.; per os for 15 consecutive days).
4) human NSCLC with EGFR mutations by subcutaneously implanting H1975 cells ($1\times10^7$ cell/mL in sterile PBS), into the right flank of athymic nude male mice (HSD, 6-7 weeks old). When the tumor volume reached approximately 100 mm³, mice were assigned randomly to either vehicle alone or OR0512 treatment groups (five mice per group). Mice were treated with either vehicle (DMSO) or OR0512 (20 mg/kg q.d.; per os for 22 consecutive days).

Tumor volumes in mm³ were determined three times a week with a digital caliper and calculated using the following formula: Tumor Volume (mm³)=length (mm)×width (mm)×width (mm)×½. Body weight was measured three times a week, and mice were observed daily for monitoring signs of stress to detect possible toxicities. One-way ANOVA was used for statistical comparisons. Data were analyzed with Prism 5.0b (GraphPad Software) by one-way ANOVA with Bonferroni post hoc. Tumor Growth Inibition (TGI) is calculated as the percent decrease of tumor growth at the end of the study in the OR0512 treatment group in comparison to the vehicle alone treatment group.

Biological Results:

The in vitro kinase assays reveal several kinase-inhibiting molecular structures. More than 20 compounds are able to inhibit at least 4 of the kinases tested (IC50 expected to be less than 100 nM on each of these kinases as the inhibition percent is better than 50% at the concentration of 100 nM, excepted for ABL and ABL T315I for which IC50 are expected to be less than 10 µM). It should be noted that these compounds display inhibitory activity on kinases that represent different and distant kinase families (serine/threonine or tyrosine kinases) involved in multiple pathways in tumor progression as developed in the introduction part (angiogesesis, migration, metastatis, tumor growth . . . ). These compounds are multi-targeted kinase inhibitors with large spectrum.

The anti-proliferative potency of compounds was evaluated either on malignant cancer cell lines or on primary endothelial cells mimicking the angiogenesis process. The EC50 corresponding to the concentration of compound inhibiting cell growth at a level of 50% were determined. The results obtained are presented in Tables B14 to B233.

We consider in those experiments that compounds presenting an EC50 superior than 3 µM are inactive on the tested cell type. Compounds with an EC50 between 1 µM and 3 µM are considered active, as Sorafenib, which is currently marketed to treat hepatocellular carcinoma, presents here an EC50 between 1 µM and 3 µM on 4 liver cancer cell lines (HepG2, HuH7, HuCCT1 and HuH6 Clone 5).

Several compounds are highly potent inhibitors of the cellular growth in each cell types tested. All compounds tested excepted OR0616 present anti-angiogenic properties on HUVEC. The growth of hepatoblastoma and cholangiocarcinoma cancer cell lines (HuCCT1 and HuH6 clone 5) is less diminished when treated with the compounds than all the other cell types. For all the other cancer cell lines, several compounds highly inhibit the cell growth. Taken together, these results indicate that the compounds of the invention are able to block at least two pathways of the tumor growth (epithelial cell proliferation and angiogenesis).

In vivo, in xenografted mice bearing tumors, OR0512 significantly induced a decrease of tumor growth in human pancreatic adenocarcinoma, human NSCLC (with a mutated form of EGFR), human hepatocellular carcinoma models, and a slight decrease of tumor growth in imatinib-resistant CML model expressing the mutated Bcr-Abl T315I protein.

TABLE B1

In vitro kinase assays. Each compound was incubated at 100 nM using an ATP 100 µM concentration. The activity is represented by the % of inhibition of the kinase compared to the control.

BRAF

| <50% | ≥50% |
|---|---|
| OR0595, OR0597, OR0598, OR0603, OR0605, OR0606, OR0610, OR0611, OR0612, OR0618, OR0620, OR0621, OR0622, OR0623, OR0636, OR0642, | OR0512, OR0599, OR0601, OR0604, OR0607, OR0608, OR0613, OR0615, OR0616, OR0617, OR0637, OR0639, |

TABLE B1-continued

In vitro kinase assays. Each compound was incubated at 100 nM using an ATP 100 μM concentration. The activity is represented by the % of inhibition of the kinase compared to the control.
BRAF

| <50% | ≥50% |
|---|---|
| OR0643, OR0697, OR0698, OR0626, OR0635, OR0816, OR0866, OR0869, OR0871, OR0882, OR0916, OR0952, OR0983, OR1004, OR1011, OR1016, OR1067 | OR0699, OR0744, OR0745, OR0864, OR0865, OR0867, OR0868, OR0896, OR0974, OR0975, OR1062 |

TABLE B2

In vitro kinase assays. Each compound was incubated at 100 nM using an ATP Km apparent concentration. The activity is represented by the % of inhibition of the kinase compared to the control.
EGFR (ErbB1)

| <50% | ≥50% |
|---|---|
| OR0595, OR0597, OR0599, OR0601, OR0603, OR0607, OR0608, OR0611, OR0612, OR0615, OR0616, OR0617, OR0618, OR0621, OR0622, OR0643, OR0745, OR0635, OR0866, OR0868, OR0882, OR0916, OR0952, OR0975, OR0983, OR1004, OR1011, OR1016, OR1062 | OR0512, OR0598, OR0604, OR0605, OR0610, OR0613, OR0620, OR0636, OR0637, OR0639, OR0642, OR0697, OR0698, OR0699, OR0744, OR0623, OR0626, OR0816, OR0864, OR0865, OR0867, OR0869, OR0871, OR0896, OR0974, OR1067 |

TABLE B3

In vitro kinase assays. Each compound was incubated at 100 nM using an ATP Km apparent concentration. The activity is represented by the % of inhibition of the kinase compared to the control.
EGFR (ErbB1) T790M L858R

| <50% | ≥50% |
|---|---|
| OR0512, OR0595, OR0597, OR0598, OR0599, OR0601, OR0603, OR0604, OR0605, OR0606, OR0607, OR0608, OR0610, OR0611, OR0612, OR0615, OR0616, OR0617, OR0618, OR0620, OR0621, OR0622, OR0636, OR0639, OR0642, OR0643, OR0697, OR0698, OR0699, OR0745 | OR0613, OR0637, OR0744 |

TABLE B4

In vitro kinase assays. Each compound was incubated at 100 nM using an ATP Km apparent concentration. The activity is represented by the % of inhibition of the kinase compared to the control.
FGFR2

| <50% | ≥50% |
|---|---|
| OR0595, OR0597, OR0598, OR0599, OR0601, OR0603, OR0604, OR0605, OR0606, OR0607, OR0608, OR0610, OR0611, OR0612, OR0615, OR0616, OR0617, OR0618, OR0620, OR0621, OR0636, OR0637, OR0639, OR0642, OR0643, OR0697, OR0698, OR0699, OR0745, OR0865, OR0866, OR0867, OR0868, OR0869, OR0871, OR0882, OR0896, OR0916, OR0952, OR0974, OR0975, OR0983, OR1004, OR1011, OR1062 | OR0512, OR0613, OR0622, OR0744, OR0623, OR0626, OR0635, OR0816, OR0864, OR1067 |

TABLE B5

In vitro kinase assays. Each compound was incubated at 100 nM using an ATP Km apparent concentration. The activity is represented by the % of inhibition of the kinase compared to the control.
KDR (VEGFR2)

| <50% | ≥50% |
|---|---|
| OR0595, OR0597, OR0598, OR0599, OR0601, OR0603, OR0605, OR0606, OR0610, OR0611, OR0612, OR0616, OR0618, OR0620, OR0621, OR0636, OR0642, OR0643, OR0697, OR0698, OR0745, OR0626, OR0865, OR0866, OR0868, OR0869, OR0871, OR0882, OR0896, OR0916, OR0952, OR0975, OR0983, OR1004, OR1011, OR1016, OR1062 | OR0512, OR0604, OR0607, OR0608, OR0613, OR0615, OR0617, OR0622, OR0637, OR0639, OR0699, OR0744, OR0623, OR0635, OR0816, OR0864, OR0867, OR0974, OR1067 |

TABLE B6

In vitro kinase assays. Each compound was incubated at 100 nM using an ATP Km apparent concentration. The activity is represented by the % of inhibition of the kinase compared to the control.
PDGFRA (PDGFR alpha)

| <50% | ≥50% |
|---|---|
| OR0595, OR0597, OR0621, OR0642, OR0643, OR0697, OR069,, OR0866, OR0869, OR0882, OR0916, OR0952, OR0983, OR1004, OR1011 | OR0512, OR0598, OR0599, OR0601, OR0603, OR0604, OR0605, OR0606, OR0607, OR0608, OR0610, OR0611, OR0612, OR0613, OR0615, OR0616, OR0617, OR0618, OR0620, OR0622, OR0636, OR0637, OR0639, OR0699, OR0744, OR0745, OR0623, OR0816, OR0871, OR0975, OR1062, OR1067 |

TABLE B7

In vitro kinase assays. Each compound was incubated at 100 nM using an ATP Km apparent concentration. The activity is represented by the % of inhibition of the kinase compared to the control.
SRC

| <50% | ≥50% |
|---|---|
| OR0595, OR0616, OR0621, OR0639, OR0643 | OR0512, OR0597, OR0598, OR0599, OR0601, OR0603, OR0604, OR0605, OR0606, OR0607, OR0608, OR0610, OR0611, OR0612, OR0613, OR0615, OR0617, OR0618, OR0620, OR0622, OR0636, OR0637, OR0642, OR0697, OR0698, OR0699, OR0744, OR0745, OR0623, OR0816, OR0869, OR0871, OR1062, OR1067 |

TABLE B8

In vitro kinase assays. Each compound was incubated at 10 μM using an ATP Km apparent concentration. The activity is represented by the % of inhibition of the kinase compared to the control.
ABL

| <50% | ≥50% |
|---|---|
| | OR0512, OR0580, OR0595, OR0597, OR0598, OR0599, OR0601, OR0603, OR0604, OR0605, OR0606, OR0607, OR0608, OR0610, OR0611, OR0612, OR0613, OR0615, OR0616, OR0617, OR0618, OR0620, OR0621, OR0622, OR0636, OR0637, OR0639, OR0642, OR0643 |

TABLE B9

In vitro kinase assays. Each compound was incubated at 10 μM using an ATP Km apparent concentration. The activity is represented by the % of inhibition of the kinase compared to the control.
ABL T315I

| <50% | ≥50% |
|---|---|
| OR0580, OR0595, OR0599, OR0601, OR0603, OR0604, OR0605, OR0607, OR0608, OR0612, OR0615, OR0616, OR0617, OR0618, OR0620, OR0636, OR0643 | OR0512, OR0597, OR0598, OR0606, OR0610, OR0611, OR0613, OR0621, OR0622, OR0637, OR0639, OR0642 |

TABLE B10

In vitro kinase assays. Each compound was incubated at 100 nM using an ATP Km apparent concentration. The activity is represented by the % of inhibition of the kinase compared to the control.
FGFR1

| <50% | ≥50% |
|---|---|
| OR0580, OR0595, OR0597, OR0598, OR0599, OR0601, OR0603, OR0604, OR0605, OR0606, OR0607, OR0608, OR0610, OR0611, OR0612, OR0615, OR0616, OR0617, OR0618, OR0620, OR0621, OR0636, OR0637, OR0639, OR0642, OR0643 | OR0512, OR0613, OR0622 |

TABLE B11

In vitro kinase assays. Each compound was incubated at 100 nM using an ATP Km apparent concentration. The activity is represented by the % of inhibition of the kinase compared to the control.
VEGFR1

| <50% | ≥50% |
|---|---|
| OR0512, OR0580, OR0595, OR0597, OR0598, OR0599, OR0601, OR0603, OR0604, OR0605, OR0606, OR0607, OR0608, OR0610, OR0611, OR0612, OR0613, OR0615, OR0616, OR0617, OR0618, OR0620, OR0621, OR0622, OR0636, OR0637, OR0639, OR0642, OR0643 | |

TABLE B12

In vitro kinase assays. Each compound was incubated at 100 nM using an ATP Km apparent concentration. The activity is represented by the % of inhibition of the kinase compared to the control.
PDGFRB

| <50% | ≥50% |
|---|---|
| OR0580, OR0595, OR0597, OR0598, OR0601, OR0603, OR0605, OR0606, OR0608, OR0610, OR0611, OR0612, OR0613, OR0617, OR0618, OR0620, OR0621, OR0622, OR0636, OR0639, OR0642, OR0643 | OR0512, OR0599, OR0604, OR0607, OR0615, OR0616, OR0637, |

TABLE B13

List of inhibited kinases by OR0512 obtained by in vitro kinase assays. OR0512 was incubated at 100 nM using an ATP Km apparent concentration. The kinases listed in the table are the kinases inhibited by OR0512 (% of inhibition of the kinase >50% compared to the control).
OR0512 (100 nM)
Kinases for which percent inhibition is >50%

ABL E255K; ABL G250E; ABL Y253F; ABL2; BLK; BMX; BRAF V600E; BTK; CSK; EPHA1; EPHA2; EPHA4; EPHB2; EPHB4; HER2; ERBB4; FES; FGR; FLT3; FMS; FRK; FYN; HCK; LCK; LYN A; MAPK14; ERK2; PKC theta; RET; VEGFR3; YES

TABLE B14

Anti-proliferative activity of the compounds of the invention on several cancer cell lines and primary endothelial cells.
A549

| $EC_{50}$ ≤ 100 nM | 100 nM < EC50 < 1 μM | $EC_{50}$ ≥ 1 μM |
|---|---|---|
| OR0512, OR0699 | OR0597, OR0598, OR0599, OR0601, OR0604, OR0606, OR0607, OR0608, OR0610, OR0611, OR0612, OR0613, OR0636, OR0637, OR0639, OR0642, OR0697, OR0744, OR0745, OR1067 | OR0615, OR0616, OR0617, OR0622, OR0623, Erlotinib, OR0626, OR0952, OR1011, OR1016, OR1062 |

TABLE B15

Anti-proliferative activity of the compounds of the invention on several cancer cell lines and primary endothelial cells.
HepG2

| $EC_{50}$ ≤ 100 nM | 100 nM < EC50 < 1 μM | $EC_{50}$ ≥ 1 μM |
|---|---|---|
| OR0512, OR0597, OR0601, OR0604, OR0606, OR0611, OR0613, OR0642 | OR0598, OR0599, OR0607, OR0608, OR0610, OR0612, OR0617, OR0636, OR0637, OR0639, OR0697, OR0699, OR0744, OR0745, OR0816, OR0865, OR0866, OR0867, OR0871, OR1016 | OR0615, OR0616, OR0622, Sorafenib, OR0635, OR0864, OR0868, OR0869, OR0882, OR0896, OR0916, OR0952, OR0974, OR0975, OR0983, OR1004, OR0626, OR0952, OR1011, OR1062, OR1067 |

TABLE B16

Anti-proliferative activity of the compounds of the invention on several cancer cell lines and primary endothelial cells.
HuCCT1

| $EC_{50}$ ≤ 100 nM | 100 nM < EC50 < 1 μM | $EC_{50}$ ≥ 1 μM |
|---|---|---|
| | OR0512, OR0607, OR0699 | OR0599, OR0604, OR0613, OR0615, OR0617, OR0636, OR0639, OR0744, OR0745, Sorafenib |

TABLE B17

Anti-proliferative activity of the compounds of the invention on several cancer cell lines and primary endothelial cells.
HuH6 Clone 5

| $EC_{50} \leq$ 100 nM | 100 nM < $EC_{50}$ < 1 μM | $EC_{50} \geq$ 1 μM |
|---|---|---|
| | | OR0512, OR0604, OR0613, OR0699, OR0744, OR0745, Sorafenib |

TABLE B18

Anti-proliferative activity of the compounds of the invention on several cancer cell lines and primary endothelial cells.
HuH7

| $EC_{50} \leq$ 100 nM | 100 nM < $EC_{50}$ < 1 μM | $EC_{50} \geq$ 1 μM |
|---|---|---|
| OR0512 | OR0604, OR0613, OR0699, OR0744, OR0745, OR0605, OR0816, OR0869, OR0871 | Sorafenib, OR0865, OR0866, OR0867, OR0868, OR0882 |

TABLE B19

Anti-proliferative activity of the compounds of the invention on several cancer cell lines and primary endothelial cells.
PC-3

| $EC_{50} \leq$ 100 nM | 100 nM < $EC_{50}$ < 1 μM | $EC_{50} \geq$ 1 μM |
|---|---|---|
| | OR0512 | OR0597, OR0604, OR0606, OR0610, OR0611, OR0613, OR0636, OR0639, OR0642 |

TABLE B20

Anti-proliferative activity of the compounds of the invention on several cancer cell lines and primary endothelial cells.
Caki-2

| $EC_{50} \leq$ 100 nM | 100 nM < $EC_{50}$ < 1 μM | $EC_{50} \geq$ 1 μM |
|---|---|---|
| OR0512 | | Sunitinib |

TABLE B21

Anti-proliferative activity of the compounds of the invention on several cancer cell lines and primary endothelial cells.
MDA-MB-231

| $EC_{50} \leq$ 100 nM | 100 nM < $EC_{50}$ < 1 μM | $EC_{50} \geq$ 1 μM |
|---|---|---|
| OR0512, OR0597, OR0604, OR0606, OR0610, OR0611, OR0613, OR0642 | OR0636, OR0639, OR0699, OR0744, OR0745, OR0626, OR1016, OR1062 | OR0952, OR1011 |

TABLE B22

Anti-proliferative activity of the compounds of the invention on several cancer cell lines and primary endothelial cells.
HT29

| $EC_{50} \leq$ 100 nM | 100 nM < $EC_{50}$ < 1 μM | $EC_{50} \geq$ 1 μM |
|---|---|---|
| OR0613, OR0699 | OR0512, OR0597, OR0598, OR0601, OR0606, OR0607, OR0610, OR0611, OR0636, OR0637, OR0639, OR0642, OR0697, OR0744, OR0745 | OR0599, OR0604, OR0608, OR0612, OR0615, OR0616, OR0617, OR0622 |

TABLE B23

Anti-proliferative activity of the compounds of the invention on several cancer cell lines and primary endothelial cells.
BxPC-3

| $EC_{50} \leq$ 100 nM | 100 nM < $EC_{50}$ < 1 μM | $EC_{50} \geq$ 1 μM |
|---|---|---|
| OR0512, OR0611, OR0699 | OR0597, OR0598, OR0603, OR0604, OR0606, OR0607, OR0608, OR0610, OR0612, OR0613, OR0618, OR0636, OR0639, OR0642, OR0697 | OR0595, OR0599, OR0601, OR0605, OR0615, OR0616, OR0617, OR0620, OR0622, OR0637, OR0643, Sunitinib, Erlotinib |

TABLE B24

Anti-proliferative activity of the compounds of the invention on several cancer cell lines and primary endothelial cells.
H1975

| $EC_{50} \leq$ 100 nM | 100 nM < $EC_{50}$ < 1 μM | $EC_{50} \geq$ 1 μM |
|---|---|---|
| | OR0512, OR0597, OR0598, OR0599, OR0606, OR0607, OR0610, OR0611, OR0613, OR0699 | OR0601, OR0604, OR0608, OR0612, OR0615, OR0616, OR0617, OR0622, OR0636, OR0637, OR0639, OR0642, OR0697, OR0744, OR0745, Erlotinib |

TABLE B25

Anti-proliferative activity of the compounds of the invention on several cancer cell lines and primary endothelial cells.
BaF3 WT

| $EC_{50} \leq$ 100 nM | 100 nM < $EC_{50}$ < 1 μM | $EC_{50} \geq$ 1 μM |
|---|---|---|
| OR0512, Imatinib, Dasatinib | | |

TABLE B26

Anti-proliferative activity of the compounds of the invention on several cancer cell lines and primary endothelial cells.
BaF3 T315I

| $EC_{50} \leq$ 100 nM | 100 nM < $EC_{50}$ < 1 μM | $EC_{50} \geq$ 1 μM |
|---|---|---|
| OR0512 | | Imatinib, Dasatinib |

TABLE B27

Anti-proliferative activity of the compounds of the invention on several cancer cell lines and primary endothelial cells.
BaF3 G250A

| $EC_{50} \leq 100$ nM | 100 nM < EC50 < 1 µM | $EC_{50} \geq 1$ µM |
|---|---|---|
| OR0512, Dasatinib | Imatinib | |

TABLE B28

Anti-proliferative activity of the compounds of the invention on several cancer cell lines and primary endothelial cells.
BaF3 G250E

| $EC_{50} \leq 100$ nM | 100 nM < EC50 < 1 µM | $EC_{50} \geq 1$ µM |
|---|---|---|
| OR0512 | | Imatinib, Dasatinib |

TABLE B29

Anti-proliferative activity of the compounds of the invention on several cancer cell lines and primary endothelial cells.
BaF3 G250A + E279N

| $EC_{50} \leq 100$ nM | 100 nM < EC50 < 1 µM | $EC_{50} \geq 1$ µM |
|---|---|---|
| OR0512, Imatinib, Dasatinib | | |

TABLE B30

Anti-proliferative activity of the compounds of the invention on several cancer cell lines and primary endothelial cells.
BaF3 E255K + M351T

| $EC_{50} \leq 100$ nM | 100 nM < EC50 < 1 µM | $EC_{50} \geq 1$ µM |
|---|---|---|
| OR0512, Dasatinib | | Imatinib |

TABLE B31

Anti-proliferative activity of the compounds of the invention on several cancer cell lines and primary endothelial cells.
HUVEC

| $EC_{50} \leq 100$ nM | 100 nM < EC50 < 1 µM | $EC_{50} \geq 1$ µM |
|---|---|---|
| OR0512, OR0598, OR0601, OR0606, OR0607, OR0610, OR0613, OR0642, OR0816, OR1067 | OR0597, OR0599, OR0604, OR0608, OR0611, OR0612, OR0615, OR0617, OR0622, OR0636, OR0637, OR0639, OR0697, OR0699, OR0744, OR0745, Dasatinib, Sunitinib, Sorafenib OR0635, OR0865, OR0866, OR0868, OR0869, OR0871, OR0896, OR1062 | OR0616, Erlotinib, OR0623, OR0626, OR0867, OR0882, OR0916, OR0952, OR0974, OR0975, OR0983, OR1004, OR1011, OR1016 |

TABLE B32

Anti-proliferative activity of the compounds of the invention on several cancer cell lines and primary endothelial cells.
HRMEC

| $EC_{50} \leq 100$ nM | 100 nM < EC50 < 1 µM | $EC_{50} \geq 1$ µM |
|---|---|---|
| OR0512 | OR0744 | OR0616, OR0617 |

TABLE B33

Anti-proliferative activity of the compounds of the invention on several cancer cell lines and primary endothelial cells.
HeLa

| $EC_{50} \leq 100$ nM | 100 nM < EC50 < 1 µM | $EC_{50} \geq 1$ µM |
|---|---|---|
| | OR0512, OR0699, OR0744, OR1067 | OR0606, OR0611, OR0745, OR0626, OR0952, OR1011, OR1016, OR1062 |

TABLE B34

Anti-tumor activity (Tumor Growth Inhibition - TGI) of OR0512 in four mice models of cancers. Mice groups (n = 5) were orally and daily dosed with either vehicle alone (DMSO) or compound OR0512. **P < 0.05 versus vehicle-treated group.

| Cancer type | Imatinib-resistant CML | Pancreatic adeno-carcinoma | NSCLC (EGFR mutated) | Hepato-cellular carcinoma |
|---|---|---|---|---|
| Implanted cells | Ba/F3 T315I | BxPC-3 | H1975 | HepG2 |
| OR0512 | 37% | 85%** | 73%** | 69%** |

The invention claimed is:
1. Compound of the following formula (I):

(I)

characterized in that,
R1 is a $C_1$-$C_6$ alkyl group,
X is $CH_2$ or C=O,
R2 is hydrogen atom, an alkyl group or a halogen atom,
Y is chosen from a group consisting of HNC(O), HNC(S), $HNSO_2$, $HNC(O)CH_2$, HNC(O)NH, HNC(S)NH, C(O)NH, $C(O)NHCH_2$, $CH_2NHC(O)$ and $CH_2NHC(S)$, and
R3 is chosen from a group consisting of:
  a phenyl group mono or polysubstituted with:
    a hydroxyl,
    a halogen,
    a $C_1$-$C_6$ alkyl-amine,
    a $C_1$-$C_6$ alkoxy,
    a $C_1$-$C_6$ trifluoroalkoxy,
    a $C_1$-$C_6$ alkyl,
    a $C_1$-$C_6$ trifluoroalkyl, a heteroaryl fragment optionally substituted with a C$_1$-C$_6$ alkyl, a C$_1$-C$_6$ trifluoroalkyl, a halogen and/or a hydroxyl, wherein said heteroaryl fragment is chosen from a group consisting of dihydrobenzofuran, indol, benzodioxol, benzotriazol, pyridine or a thiazol, an imidazole, with the proviso that Y is HNC(S), HNSO$_2$, HNC(O)CH$_2$, HNC(O)NH, HNC(S)NH, C(O)NHCH$_2$, CH$_2$NHC(O), CH$_2$NHC(S) or C(O)NH wherein NH is directly linked to R3, a heteroaryl group, non aromatic monosubstituted cyclic group, and a fragment chosen from a group consisting of:

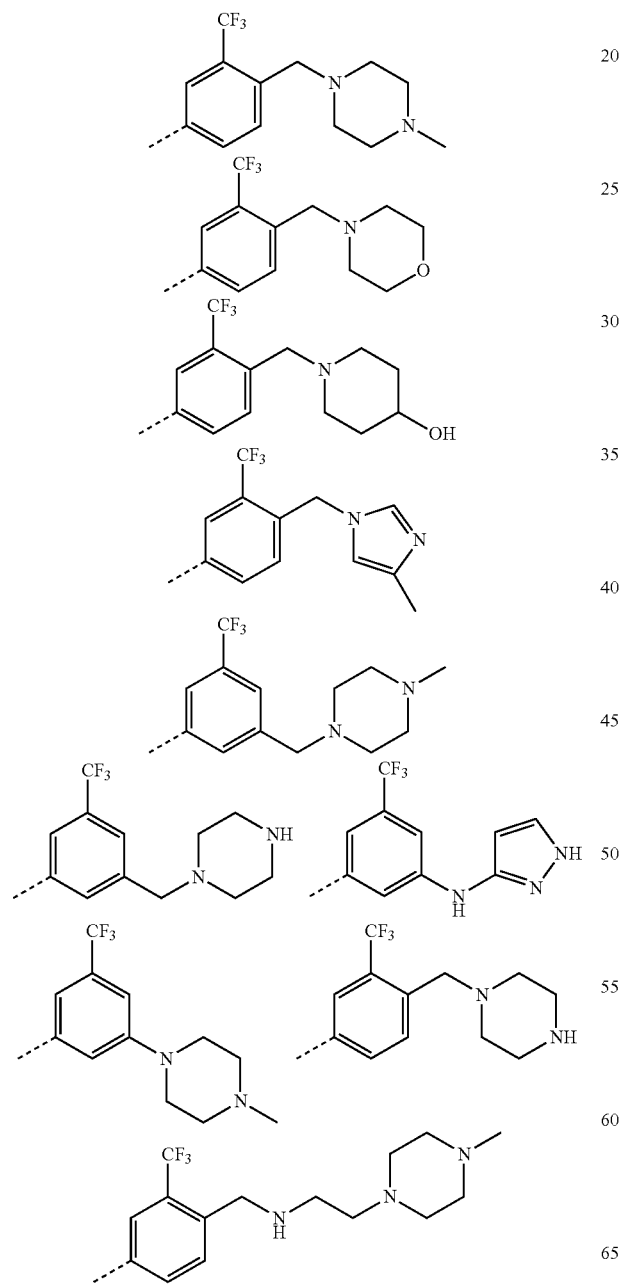

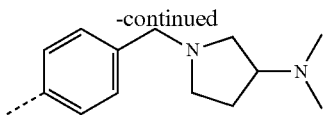

and/or the pharmaceutically acceptable addition salts, solvates, enantiomers, diastereoisomers thereof, as well as mixtures thereof.

2. Compound according to claim 1, characterized in that, X is CH$_2$, and R2 is an alkyl or a halogen.

3. Compound according to claim 1, characterized in that,

R1 is C$_1$-C$_6$ alkyl,

X is CH$_2$,

R2 is a methyl or a chloride atom,

Y is chosen from a group consisting of HNC(O), HNC(O)CH$_2$, HNC(O)NH, HNC(S)NH, C(O)NH, C(O)NHCH$_2$, and CH$_2$NHC(O), R3 is chosen from a group consisting of:
  a phenyl group mono substituted with a C$_1$-C$_6$ trifluoroalkyl group, a C$_1$-C$_6$ trifluoroalkoxy group, a C$_1$-C$_6$ alkyl group, a halogen, or a thiazol group optionally monosubstituted by a CF$_3$ and/or a methyl group,
  a phenyl group polysubstituted with a C$_1$-C$_6$ trifluoroalkyl, a C$_1$-C$_6$ alkyl-amine, and/or a hydroxyl group,
  a pyridine group, optionally substituted with a C$_1$-C$_6$ alkyl or a C$_1$-C$_6$ trifluoroalkyl,
  non aromatic cyclic group chosen between a cyclic C$_3$-C$_{10}$ alkyl, monosubstituted with a C$_1$-C$_6$ alkyl and/or a C$_1$-C$_6$ trifluoroalkyl, and
  a fragment chosen from a group consisting of:

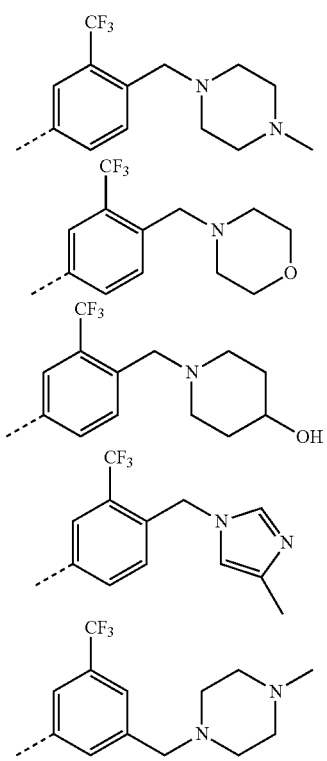

-continued

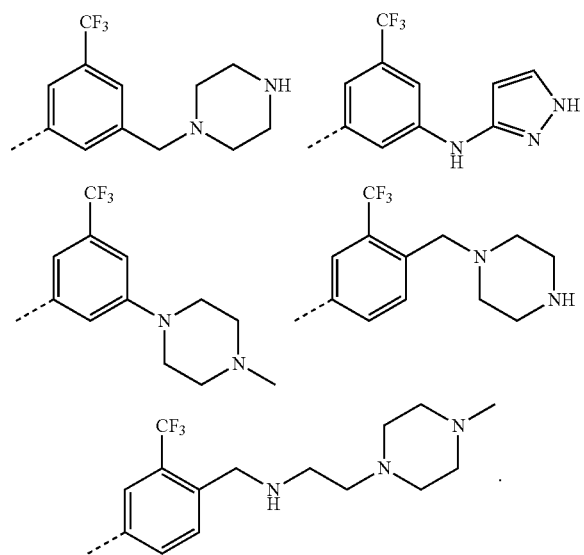

4. Compound according to claim 1, characterized in that,
R1 is a $C_1$-$C_6$ alkyl group,
X is a $CH_2$,
R2 is methyl,
Y is HNC*(O), wherein C* is linked to R3 and
R3 is chosen from a group consisting of:

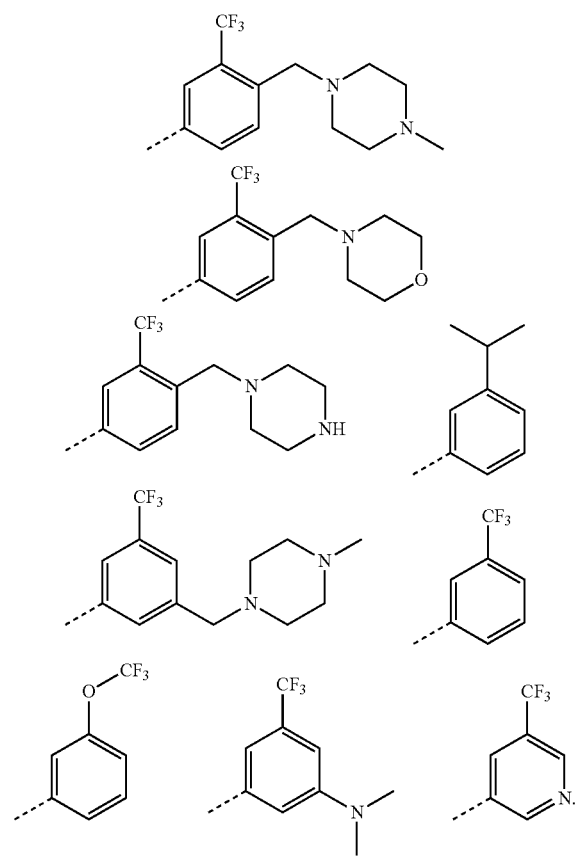

5. Compound according to claim 1 of general formula (II):

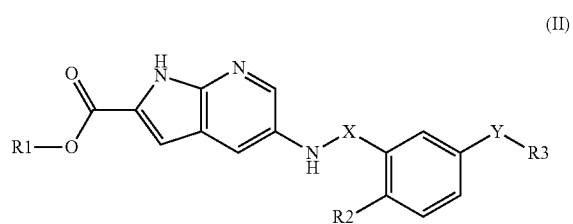

(II)

characterized in that,
R1 is a methyl,
X is a $CH_2$,
R2 is methyl,
Y is HNC*(O), wherein C* is linked to R3 and
R3 is chosen from a group consisting of:

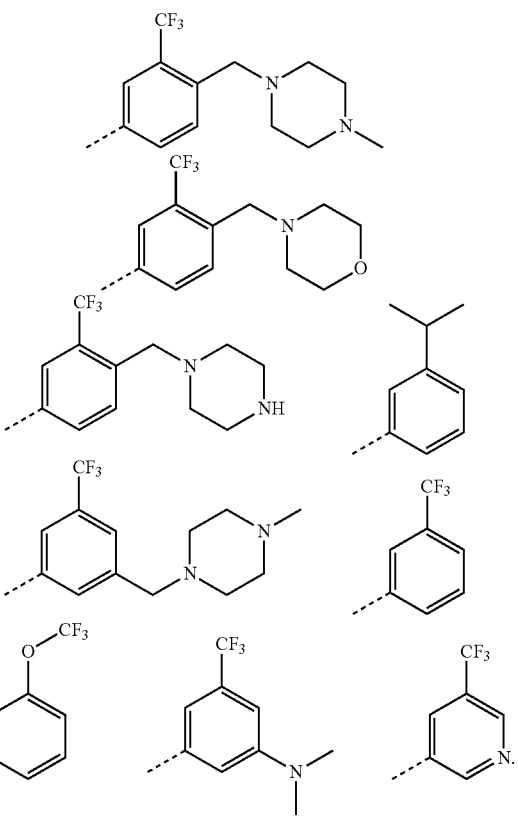

6. Compound according to claim 1, characterized in that X is C=O and R2 is an alkyl or a halogen.

7. Method of preparation of the compounds according to claim 1, characterized in that it comprises at least one of the following steps:
   a. in the case of X being CO, forming the NH—CO bond by means of peptide coupling techniques with an aromatic carboxylic acid substituted with an $NO_2$ group, or if X is $CH_2$, forming the NH—$CH_2$ bond by a reductive amination with an aromatic aldehyde substituted with an $NO_2$ group, and
   b. reducing the $NO_2$ group into $NH_2$.

8. Method of preparation according to claim 7, characterized in that the method comprises one of the following steps:

c₁) forming a urea in the case of Y being HNC(O)NH, by reacting the compound obtained after step b) with an isocyanate, c₂) forming a thiourea in the case of Y being HNC(S)NH, by reacting the compound obtained after step b) with an isothiocyanate, c₃) forming a sulfonamide in the case of Y being HNSO₂, by reacting the compound obtained after step b) with a halogen sulfonyl c₄) forming an amide in the case of Y being HNCO, by reacting the compound obtained after step b) with an activated carboxylic acid, or c₅) forming a thioamide in the case of Y being HNCS, by reacting the compound obtained after step c4) with the Lawesson's reagent, and d) optionally saponifying the obtained product.

9. Pharmaceutical composition, characterized in that it contains, as active principle, a compound according to claim 1 and a pharmaceutical acceptable excipient.

10. Method for treating a human or animal disease selected from the group consisting of liver cancer, pancreatic cancer, lung cancer, breast cancer, prostate cancer, leukemias, renal cancer, endometrial cancer, colorectal cancer, chemoresistant cancers, and macular degeneration comprising administering a compound according to claim 1 to a patient in need thereof.

11. Method for inhibiting protein kinases selected from the group consisting of BRAF, EGFR, FGFR2, KDR, PDGFRA, SRC, ABL, FGFR1, VEGFR1, PDGFRB, ABL2, BLK, BMX, BTK, CSK, EPHA1, EPHA2, EPHA4, EPHB2, EPHB4, HER2, ERBB4, FES, FGR, FLT3, FMS, FRK, FYN, HCK, LCK, LYN, MAPK14, ERK2, PKC theta, RET, VEGFR3 and YES in diseases comprising administering a compound according to claim 1 to a patient in need thereof.

12. An in vitro method for predicting whether a patient in need thereof is likely to respond to at least one of the compounds according to claim 1, which method comprises determining the expression levels, gene modifications, activation state or appearance of a mutated form of the protein kinase in a sample of said patient, wherein said protein kinase is selected from the following list of kinases BRAF, EGFR, FGFR2, KDR, PDGFRA, SRC, ABL, FGFR1, VEGFR1, PDGFRB, ABL2, BLK, BMX, BTK, CSK, EPHA1, EPHA2, EPHA4, EPHB2, EPHB4, HER2, ERBB4, FES, FGR, FLT3, FMS, FRK, FYN, HCK, LCK, LYN, MAPK14, ERK2, PKC theta, RET, VEGFR3 and YES.

13. An In vitro method for predicting whether a patient in need thereof is likely to respond to at least one of the compounds according to claim 1, which method comprises the following steps:

a) putting into contact said compound(s) with a sample of human tissue or cells, b) determination of the activity of the compound(s) on the sample via for example IC50 and/or via a compared activity of the protein kinases present, which can for example be chosen from the following list of kinases BRAF, EGFR, EGFR T790M L858R, FGFR2, KDR PDGFRA, SRC, ABL, ABL T3151, FGFR1, VEGFR1, PDGFRB, ABL E255K, ABL G250E, ABL Y253F, ABL2, BLK, BMX, BRAF V600E, BTK, CSK, EPHA1, EPHA2, EPHA4, EPHB2, EPHB4, HER2, ERBB4, FES, FGR, FLT3, FMS, FRK, FYN, HCK, LCK, LYN, MAPK14, ERK2, PKC theta, RET, VEGFR3 and YES;

c) optionally conducting the same test as step e) with healthy cells of said patient to determine the toxicity of the compound according to claim 1 to healthy cells;

d) selecting the compound according to claim 1 presenting the best activity, and/or eventually lowest toxicity, to be administered to the patient in need thereof.

14. Compound according to claim 1, characterized in that, R1 is a $C_1$-$C_6$ alkyl group,
X is a C=O,
R2 is methyl,
Y is HNC*(O), wherein C* is linked to R3 and
R3 is chosen from a group consisting of:

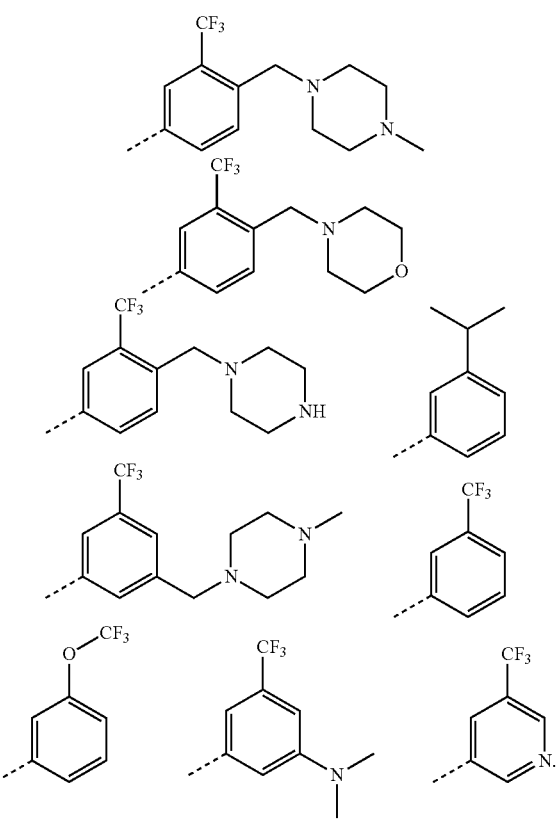

15. Method for inhibiting protein kinases in diseases according to claim 11, wherein the disease is selected from the group consisting of cancers, immune disorders, inflammatory diseases, thrombotic diseases, neurodegenerative diseases, bone diseases, macular degeneration, fibrosis, cystogenesis, hyperproliferative diseases.

16. Method for inhibiting cellular proliferation and/or angiogenesis involved in treating a human or animal disease selected from the group consisting of liver cancer, pancreatic cancer, lung cancer, breast cancer, prostate cancer, leukemias, renal cancer, endometrial cancer, colorectal cancer, chemoresistant cancers, and macular degeneration comprising administering a composition according to claim 9 to a patient in need thereof.

17. Method for inhibiting protein kinases selected from the group consisting of BRAF, EGFR, FGFR2, KDR, PDGFRA, SRC, ABL, FGFR1, VEGFR1, PDGFRB, ABL2, BLK, BMX, BTK, CSK, EPHA1, EPHA2, EPHA4, EPHB2, EPHB4, HER2, ERBB4, FES, FGR, FLT3, FMS, FRK, FYN, HCK, LCK, LYN, MAPK14, ERK2, PKC theta, RET, VEGFR3 and YES in diseases comprising administering a composition according to claim 9 to a patient in need thereof.

18. Method for inhibiting protein kinases in diseases according to claim 17, wherein the disease is selected from the group consisting of cancers, immune disorders, inflammatory diseases, thrombotic diseases, neurodegenerative diseases, bone diseases, macular degeneration, fibrosis, cystogenesis, hyperproliferative diseases.

* * * * *